United States Patent [19]
Goldberg et al.

[11] Patent Number: 5,430,045
[45] Date of Patent: Jul. 4, 1995

[54] METHOD OF REDUCING OR PREVENTING BONE MARROW HYPOPLASIA

[75] Inventors: Dennis I. Goldberg, Hawthorn Woods; Gary Pace, Northfield; Randy D. White, Crystal Lake; Daniel M. Wilson, Woodstock, all of Ill.

[73] Assignee: Free Radical Sciences, Inc., Cambridge, Mass.

[21] Appl. No.: 68,385

[22] Filed: May 28, 1993

Related U.S. Application Data

[63] Continuation-in-part of Ser. No. 872,549, Apr. 23, 1992.

[51] Int. Cl.⁶ .......................................... A61K 31/425
[52] U.S. Cl. ........................................ 514/369; 514/50
[58] Field of Search ................................ 514/50, 369

[56] References Cited

U.S. PATENT DOCUMENTS

| | | | |
|---|---|---|---|
| 2,712,202 | 7/1955 | Hosler et al. | 47/57.5 |
| 3,737,536 | 6/1973 | Sagner et al. | 424/246 |
| 3,755,578 | 8/1973 | McFarland et al. | 424/246 |
| 4,175,130 | 11/1979 | Yamanaka et al. | 424/270 |
| 4,335,210 | 7/1982 | Meister et al. | 435/113 |
| 4,338,315 | 7/1982 | Paget et al. | 424/246 |
| 4,398,026 | 8/1983 | Takano | 544/133 |
| 4,420,479 | 12/1983 | Morwick et al. | 424/246 |
| 4,434,158 | 2/1984 | Meister | 424/94 |
| 4,438,124 | 3/1984 | Meister | 424/270 |
| 4,563,471 | 1/1986 | Satzinger et al. | 514/369 |
| 4,647,453 | 3/1987 | Meisner | 424/54 |
| 4,647,571 | 3/1987 | Meister | 514/369 |
| 4,665,082 | 5/1987 | Meister et al. | 514/365 |
| 4,710,489 | 12/1987 | Meister | 514/18 |
| 4,752,618 | 7/1988 | Mascioli et al. | 514/549 |
| 4,775,675 | 10/1988 | Gyorgydeak et al. | 514/307 |
| 4,780,475 | 10/1988 | Cerra et al. | 514/408 |
| 4,784,685 | 11/1988 | Meister | 71/106 |
| 4,791,125 | 12/1988 | Clark | 514/369 |
| 4,798,835 | 1/1989 | Krupp et al. | 514/369 |
| 4,839,387 | 7/1989 | Poli | 514/19 |
| 4,868,114 | 9/1989 | Nagasawa et al. | 435/112 |
| 4,879,370 | 11/1989 | Meister | 530/331 |
| 4,963,577 | 10/1990 | Schorlemmer et al. | 514/369 |
| 5,002,953 | 3/1991 | Hindley | 514/275 |
| 5,028,627 | 7/1991 | Kilbourn et al. | 514/565 |
| 5,039,609 | 8/1991 | Klein | 435/68.1 |
| 5,053,387 | 10/1991 | Alexander | 514/2 |
| 5,055,446 | 10/1991 | Alexander et al. | 514/2 |
| 5,089,268 | 2/1992 | Katz | 424/450 |
| 5,095,027 | 3/1992 | Goldberg et al. | 514/369 |
| 5,158,883 | 10/1992 | Griffith | 435/240.2 |
| 5,208,249 | 5/1993 | Rowe et al. | 514/369 |
| 5,214,062 | 5/1993 | Mark et al. | 514/369 |

FOREIGN PATENT DOCUMENTS

| | | |
|---|---|---|
| 0002978 | 7/1979 | European Pat. Off. . |
| 0257992 | 3/1988 | European Pat. Off. . |
| 0318330 | 5/1989 | European Pat. Off. . |
| 0327263A1 | 8/1989 | European Pat. Off. . |
| 0338459A2 | 10/1989 | European Pat. Off. . |
| 0373002 | 6/1990 | European Pat. Off. . |
| 0374390 | 6/1990 | European Pat. Off. . |
| 0415598A1 | 3/1991 | European Pat. Off. . |
| 02296428 | 9/1976 | France . |
| 2141765 | 3/1973 | Germany . |
| 47-8537 | 11/1972 | Japan . |
| 8403625 | 9/1984 | WIPO . |
| 91/14424 | 10/1991 | WIPO . |
| 93/11104 | 6/1993 | WIPO . |

OTHER PUBLICATIONS

Bounous, et al., *Immunoenhancing Property of Dietary Whey Protein in Mice: Role of Glutathoine*, Clinical Investigative Medicine, vol. 12, No. 4, pp. 154–161 (1989).

(List continued on next page.)

*Primary Examiner*—Richard L. Raymond
*Attorney, Agent, or Firm*—Pennie & Edmonds

[57] ABSTRACT

The present invention provides a method for reducing, or preventing, bone marrow hypoplasia in a patient at risk of, or having, same. To this end, when a glutathione intracellular stimulator is administered to such a patient, the risk of bone marrow hypoplasia is reduced or prevented. In an embodiment, the composition for stimulating the intracellular glutathione levels comprises L-2-oxothiazolidine-4-carboxylate.

20 Claims, 7 Drawing Sheets

OTHER PUBLICATIONS

Bone, et al., *Definitions for Sepsis and Organ Failure*, Critical Care Medicine, 1992, vol. 20, No. 6, pp. 724–725.

American College of Chest Physicians/Society of Critical Care Medicine Consensus Conference Committee, *American College of Chest Physicians/Society of Critical Care Medicine Consensus Conference: Definitions for Sepsis and Organ Failure and Guidelines for the Use of Innovative Therapies in Sepsis*, Critical Care Medicine, Jun. 1992, vol. 20, No. 6, pp. 864–874.

Kilbourn, et al., *Inhibition of Interleukin-1-α-Induced nitric Oxide Synthase in Vascular Smooth Muscle and Full Reversal of Interleukin-1-α Induced Hypotension by $N^\omega$-Amino-L-Arginine*, Journal of the National Cancer Institute, Jul. 1, 1992, vol. 84, No. 13, pp. 1008–1016.

Osol, et al., EDs., *Remington's Pharmaceutical Sciences*, 1980, Sixteenth Edition.

W. Lucht et al, *Prevention of Release of Granulocyte Aggregants into Sheep Lung Lymph Following Endotoxemia by N-Acetylcysteine*, The American Journal of the Medical Sciences, vol. 294, No. 3, Sep. 1987, pp. 161–167.

G. Bernard et al, *Effect of N-Acetylcysteine on the Pulmonary Response to Endotoxin in the Awake Sheep and Upon In Vitro Granulocyte Function*, J. Clin. Invest., vol. 73, Jun. 1984, pp. 1772–1784.

A. Cantin et al, *Normal Alveolar Epithelial Lining Fluid Contains High Levels of Glutathione*, pp. 152–157. (1987).

L. Smith et al, *Effect of Fasting on Hyperoxic Lung Injury in Mice*, Am. Rev. Respir. Dis. 1990; 141:141–149.

J. Strausz et al, *Oxygen Radical Production by Alveolar Inflammatory Cells in Idiopathic Pulmonary Fibrosis*, Am. Rev. Respir. Dis. 1990; 141:124–128.

A. Cantin et al, *Glutathione Deficiency in the Epithelial Lining Fluid of the Lower Respiratory Tract in Idiopathic Pulmonary Fibrosis*, Am. Rev. Respir. Dis. 1989; 139:370–372.

*Guarding Against Cellular Glutathione Deficiency*, Nutrition Reviews, vol. 48, No. 9, Sep. 1990, pp. 346–348.

A. Cantin et al, *Oxidants, Antioxidants and the Pathogenesis of Emphysema*, Eur. J. Respir. Dis (1985) 66, Suppl. 139, pp. 7–17.

I. Cotgreave et al, *Lung and Systemic Thiol Homeostasis During an Acute Lung Inflammation in the Rat*, Toxicology, 50 (1988), pp. 331–343.

J. Sun et al, *Effects of Buthionine Sulfoximine on the Development of Ozone-Induced Pulmonary Fibrosis*, Experimental and Molecular Pathology 49 (1988), pp. 254–266.

S. Baldwin et al, *Oxidant Activity in Expired Breath of Patients with Adult Respiratory Distress Syndrome*, The Lancet, Jan. 4, 1986, pp. 11–14.

M. F. Tsan et al, *Enhancement of Intracellular Glutathione Protects Endothelial Cells Against Oxidant Damage*, Biochemical and Biophysical Research Communications, vol. 127, No. 1, Feb. 28, 1985, pp. 270–276.

M. F. Tsan et al, *L-2—Oxothiazolidine-4-Carboxylate Protects Endothelial Cells Against Hyperocia-Induced Injury*, Inflammation, vol. 12, No. 2, 1988, pp. 113–121.

P. H. S. Sporn et al, *Complex Effects of In Vitro Hyperoxia on Alveolar Macrophage Arachidonic Acid Metabolism*, American Journal of Respiratory Cell and Molecular Biology, vol. 2, No. 1, Jan. 1990, pp. 81–90.

M. A. Passero et al, *L-2-Oxothiazolidine-4-Carboxylic Acid Increases Glutathione in Mouse Lung*, A. Rev. Respir. Dis., vol. 133, 1986, p. A395.

Uhlig, et al., *Glutathione Enhancement in Various Mouse Organs and Protection by Glutathione Isopropyl Ester Against liver Injury*, Jun. 15, 1990, p. 1877–.

Bellin, et al., *Purification of Glycosaminoglycens from Bovine Follicular Fluid*, J. Dairy Sci., Nov. 9, 1987, vol. 70, pp. 1913–1919.

Calvin, et al., *Estimation and Manipulation of Glutathione Levels in Prepuberal Mouse Ovaries and Ova: Relevance to Sperm Nucleus Transformation in the Fertilized Egg*, Gamete Research, 1986, vol. 14, pp. 165–275.

Gordon, et al., *Applications of Micromanipulation to Human in Vitro Fertilization*, Journal of In Vitro Fertilization and Embryo Transfer, 1988, vol. 5, No. 2, pp. 57–60.

Perreault, et al., *Importance of Glutathione in the Acquisition and Maintenance of Sprem Nuclear Decondensing Activity in Maturing Hamster Oocytes*, Developmental Biology, 1988, vol. 125, pp. 181–186.

Perreault, et al., *The Timing of Hamster Sperm Nuclear Decondensation and Male Pronucleus Formation is Related to Sperm Nuclear Disulfide Bond Content*, Biology of Reproduction, 1987, vol. 36, pp. 239–244.

Perreault, et al., *The Role of Disulfide Bond Reduction During Mammalian Sperm Nuclear Decondensation in Vivo*, Developmental Biology, 1984, vol. 101, pp. 160–167.

(List continued on next page.)

OTHER PUBLICATIONS

Reyes, et al., *Heparin and Glutathione: Physiological Decondensing Agents of Human Sperm Nuclei*, Gamete Research, 1989, vol. 23, pp. 39–47.

Zirkin, et al., *In Vitro and In Vivo Studies of Mammalian Sperm Nuclear Decondensation*, Gamete Research, 1985, vol. 11, pp. 349–365.

Shapiro, *The Control of Oxidant Stress at Fertilization*, Science, Apr. 26, 1991, pp. 533–536.

Oeriu, et al., *4-Thiazolidinecarboxylic Acids for Live-Stock Raising*, Ger. Offen, Oct. 22, 1970, 17 pages.

Slaweta, et al., *The Effect of Glutathione on the Motility and Fertility of Frozen Bull Sperm*, Amin. Reprod. Sci., 1987, vol. 13, No. 4, pp. 249–253.

Perreault, et al., *Importance of Glutathione In the Acquisition And Maintenance of Sperm Nuclear Decondensing Activity In Maturing Hamster Oocytes*, Dev. Biol., 1988, vol. 125, No. 1, pp. 181–186.

Lassalle, et al., *Relationship Between Fertilizing Ability of Frozen Human Spermatozoa and Capacity for Heparin Binding and Nuclear Decondensation*, J. Reprod. Fertil, 1992, vol. 95, No. 2, pp. 313–324.

Wellman, et al., *Radioprotection by glutathione ester: Transport of glutathione ester into human lymphoid cells and fibroblasts*, Proc. Natl. Acad. Sci. USA, 1984, vol. 81, pp. 4732–4735.

Martenson, et al., *Glutathione metabolism in the lung: Inhibition of its synthesis leads to lamellar body and mitochondrial defects*, Proc. Natl. Acad. Sci. USA, 1989, vol. 86, pp. 5296–5300.

Roberts, et al., *Prodrugs of L-Cysteine as Protective Agents against Acetaminophen-Induced Hepatotoxicity. 2-(Polyhydroxyalkyl)- and 2-(Polyacetoxyalkyl)-thiazolidine-4(R)-carboxylic Acids*, J. Med. Chem. 1987, vol. 30, No. 10, pp. 1891–1896.

Astor, et al., *Relationship Between Intracellular 'GSH Levels and Hypoxic Cell Radiosensitivity*, Pharmac. Ther., 1988, pp. 115–121.

Martenson, et al., *Mitochondrial damage in muscle occurs after marked depletion of glutathione and is prevented by giving glutathione monoester*, Proc. Natl. Acad. Sci. USA, 1989, vol. 86, pp. 471–475.

Meister, *Glutathione Esters Increase Cellular Glutathione Levels and Are Thus Protective Against Oxidants and Other Compounds*, Cornell University, New York (1989).

Bounous et al., *The influence of dietary whey protein on ... glutathione and the diseases of aging*, American Chemical Society, CA 112 (1989).

Kuzuya, et al., *Protective role of intracellular glutathione against oxidized low density lipoprotein in cultured endothelial cells*, Biochem. Biophys. Res. Commun 163 (3) 1989.

Roseneld et al., *Macrophage-derived Foam Cells Freshly Isolated from Rabbit Atherosclerotic Lesions Degrade Modified Lipoproteins, Promote Oxidation of Low-Density Lipoproteins, and Contain Oxidation-specific Lip--Protein Adducts*, The American Society for Clinical Investigation, Inc., 1991, vol. 87, pp. 90–99.

Heinecke, et al., *The Role of Sulfur-containing Amino Acids in Superoxide Production and Modification of Low Density Lipoprotein by Arterial Smooth Muscle Cells*, The Journal of Biologicla Chemistry, 1987, vol. 262, No. 21, pp. 10098–10103.

Parthasarathy, *Oxidation of low-density lipoprotein by thiol compounds leads to its recognition by the acetyl LDL receptor*, Biochimica et Biophysica Acta, 917, 1987, pp. 337–340.

Roederer, et al., *Cytokine-stimulated human immunodeficiency virus replication is inhibited by N-acetyl-L-cystein*, Proc. Natl. Acad. Sci. USA, 1990, vol. 87, pp. 4884–4888.

Kalebic, et al., *Suppression of human immunodeficiency virus expression in chroniclaly infected monocytic cells by glutathione, glutathione ester, and N-acetylcysteine*, Proc. Natl. Acad. Sci. USA, 1991.

Gustafson, et al., *Aids–Antiviral Sulfolipids from Cyanobacteria (Blue-Green Algae)*, J. Natl. Cancer Inst., 1989, vol. 81, No. 16, pp. 1254–1258.

Prendergast, et al., *Arachidonic Acid-Biding Peptides, Antibodies Produced to these Peptides, and unsaturated Fatty Acid Compounds Having Affinity for the Peptides for Therapy, Pharmaceuticsl, and Product Sterilization*, Chemical Abstracts, 1992, vol. 116, p. 84.

Frankova, *The Effects of Amino Acids with Sulfhydryl Groups on Herpest Viruses in Vitro*, Acla Virol, Engl. Ed., (1967), vol. 11, No. 6, pp. 559–561.

Abate, et al. *Redox Regulation of Fos and Jun DNA--Finding Activity in Vitro*, Science, Sep. 1990, vol. 249, pp. 1157–1161.

(List continued on next page.)

OTHER PUBLICATIONS

Duh, et al. *Tumor Necrosis Factor α Activates Human Immunodeficiency Virus Type 1 through Induction of Nuclear Factor Binding to the NF-kB Sites int he Long Terminal Repeat*, Proc. Natl. Acad. Sci. USA, Aug. 1989, vol. 86, pp. 5974–5978.

Staal, et al., *Intracellular Thiols Regulate Activation of Nuclear Factor kB and Transcription of Human Immunodeficiency Virus*, Proc. Natl. Acad. Sci. USA, Dec. 1990, vol. 87, pp. 9943–9947.

Mihm, et al., *Inhibition of HIV-1 Replication and NF-xB activity by Cysteine and Cysteine Derivatives*, Aids 1991, vol. V. No. 5, pp. 497–503.

Stevens, *Human Herpesviruses, a Consideration of Latent State*, Microbiological Reviews, Sep. 1989, pp. 318–332.

Schnittman, et al., *The Reservoir for HIV-1 in Human Peripheral Blood is a T Cell that Maintains Expression of CD4, Science, Jul. 21, 1989, vol. 245, pp. 305–308.*

Peristeris, et al., *N-Acetylcystein and Glutathione as Inhibitors of Tumor Necrosis Factor Production*, Cell. Immunol., 1992, vol. 140, No. 2, pp. 390–399.

Keller, et al., *Decreased Hepatic Gluthatione Levesl in Septic Shock. Predisposition of Hepatocytes to Oxidative Stress: an Experimental Approach*, Arch. Surg. (Chicago), 1985, vol. 120, No. 8, pp. 941–945.

Pacht, et al., *Deficiency of Alveolar Fluid Glutathione in Patients with Sepsis and the Adult Respiratory Distress Syndrome*, Chest, 1991, vol. 100, No. 5, pp. 1397–1403.

Flaherty, et al., *Reperfusion Injury*, Free Radical Biology & Medicine, 1988, vol. 5, pp. 409–419.

Darley-Usmar, et al., *Oxygen and Reperfusion Damage: an Overview*, Free Radi. Res. Comms., vol. 7, No. 3–6, pp. 247–254 (1989).

Lachman, et al., The Theory and Practice of Industrial Pharmacy, 1976, 2nd Ed., pp. 513–524.

Bjelton, et al., *Availability of Cysteine and of L-2-Oxo-Thiazolidine-4-Carboxylic Acid as a Source of Cysteine in Intravenous Nutrition*, J. Parenter Enteral Nutr., Mar.-Apr. 1990, vol. 14, No. 2, pp. 177–182.

Nappe, et al., *Electrophoretic Analysis of Alkylated Proteins of Human Hair from Various Ethnic Groups*, J. Soc. Cosmet, Chem., Mar./Apr. 1989, vol. 40, pp. 91–99.

Pruche, et al., *Changes in Glutathione Content in Human Hair Follicle Keratinocytes as a Function of Age of Donor: Relation with Glutathione Dependent Enzymes*, International Journal of Cosmetic Science, 1991, vol. 13, pp. 117–124.

Kermici, et al., *Evidence for an Age-Correlated Change in Glutathione Metabolism Enzyme Activities in Human Hair Follicle*, Mechanisms of Ageing and Development, 1990, vol. 53, pp. 73–84.

Rao, et al., *Synthesis and Characterization of Defensin NP-1*, Int. J. Peptide Protein Res. 1992, vol. 40, pp. 507–514.

Angier, *From the body Itself, Hope for a New Breed of Potent Antibiotics*, New York Times, Feb. 26, 1991, pp. 26–27.

Levy, et al., *Transport of Glutathione Diethyl Ester into Human Cells*, Proc. Natl. Acad. Sci, USA, Oct. 1993, vol. 19, pp. 9171–9175.

Jimenez, et al., *Treatment with ImuVert/N-Acetylcysteine Protects Rats from Cyclophosphamide/Cytarabine-Induced Alopecia*, Cancer Investigation, 1992, vol. 10, No. 4, pp. 271–276.

Thompson, et al, *Hematologic Toxicity of AZT and ddC Administered as Single Agent, and in Combination to Rats and Mice*, Fundamental and Applied Toxicology, 17, 159–176 (1991).

Cretton, *Catabolism of 3'-Azido-3'-deoxythymidine in Hepatocytes in Liver Microsomes, with Evidence of Formation of 3'-Amino-3'-deoxythymidine, a Highly Toxic Catabolite for Human Bone Marrow Cells*, Molecular Pharmacology, 39:258–266 (1991).

Handlon et al, *Thiol Reduction of 3'-Azidothymidine to 3'-Aminothymidine; Kinetics and Biomedical Implications*, Pharmaceutical Research, vol. 5, No. 5 (1988).

Lamperty et al, *Abnormal Skeletal and Cardiac Muscle Mitochrondria Induced by Zidovudine AZT in Human Muscles in Vitro and in Animal Model*, Laboratory Investigation, 65:742 (1991).

Suthanthiran et al, *Glutathione regulates activation-dependent DNA synthesis in highly purified normal T lymphocytes stimulated via the CD2 and CD3 antigens*, Proc. Natl. Acad. Sci USA vol. 87, pp. 3343–3347 (1990).

Mandel et al, Chemical Abstracts, vol. 112, No. 214704n (1990).

Chung et al, Chemical Abstracts, vol. 112, No. 177373f (1990).

Moslen et al, Chemical Abstracts, vol. 110, 109660f (1989).

Roederer et al, Chemical Abstracts, vol. 113 (1990) 57237p.

Mitchell et al, Br. J. Cancer Suppl. VIII (Jun. 1987) pp. 96–104.

Chang et al, Chemical Abstracts, vol. 115, No. 272877u (1991).

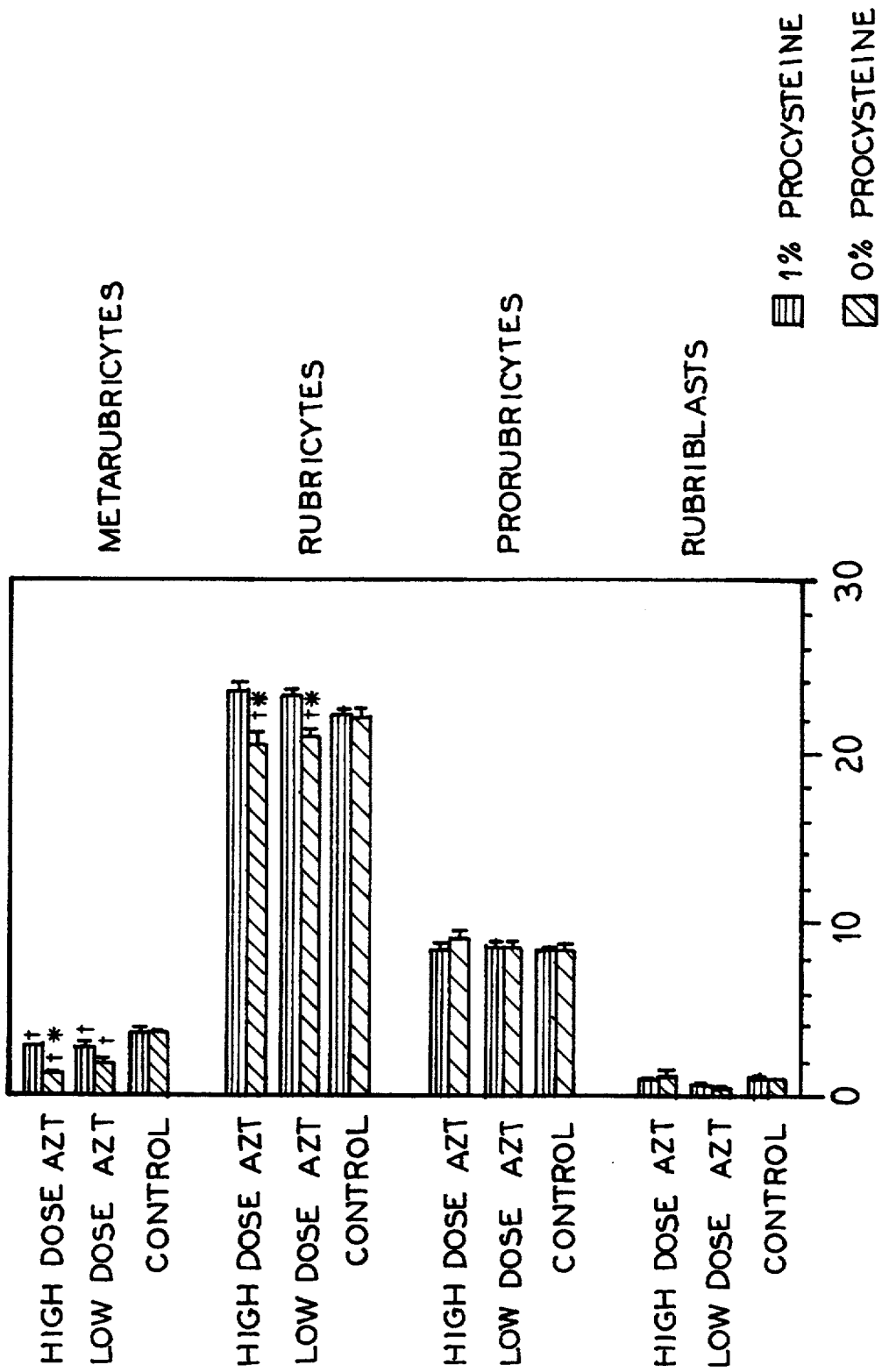

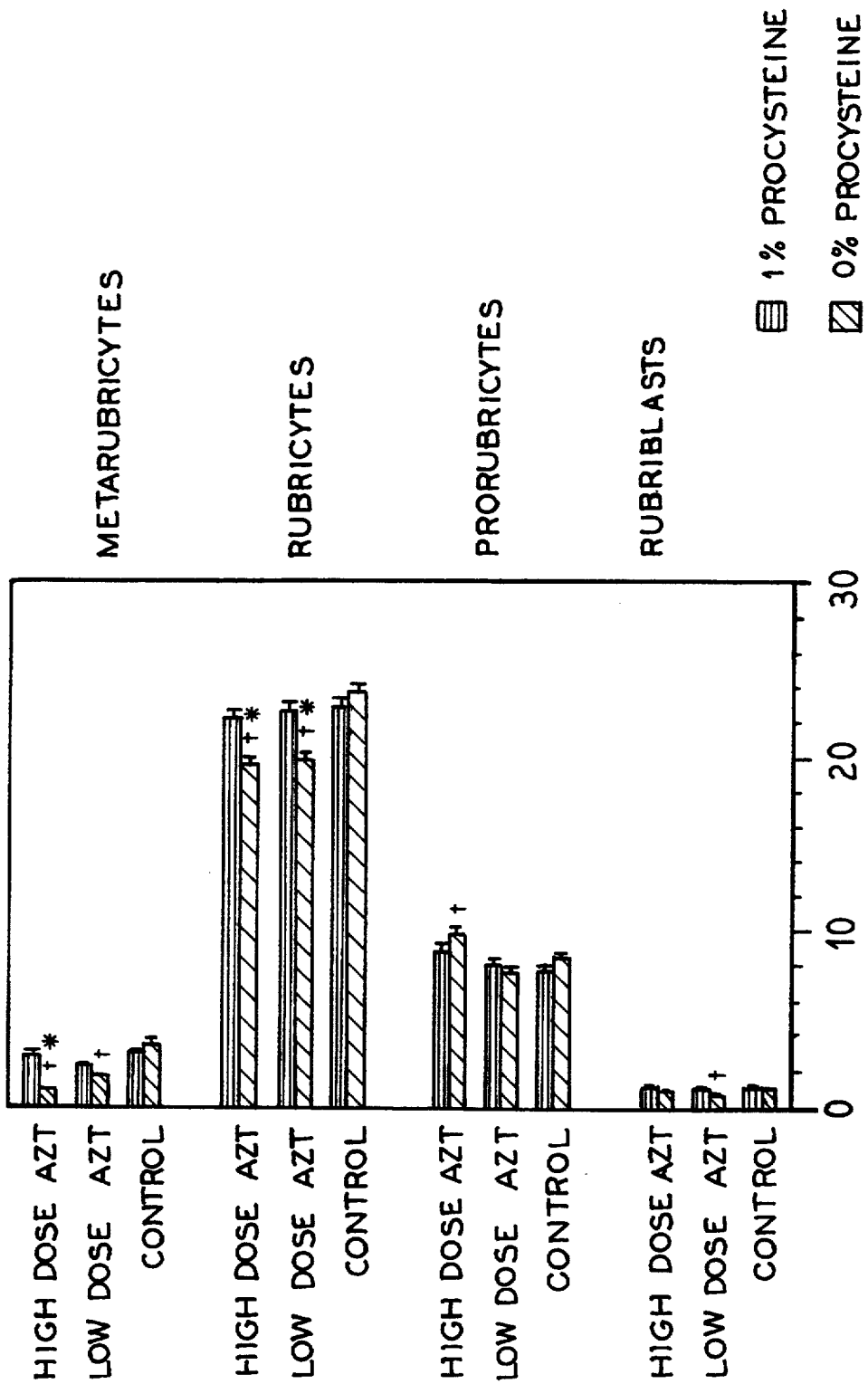

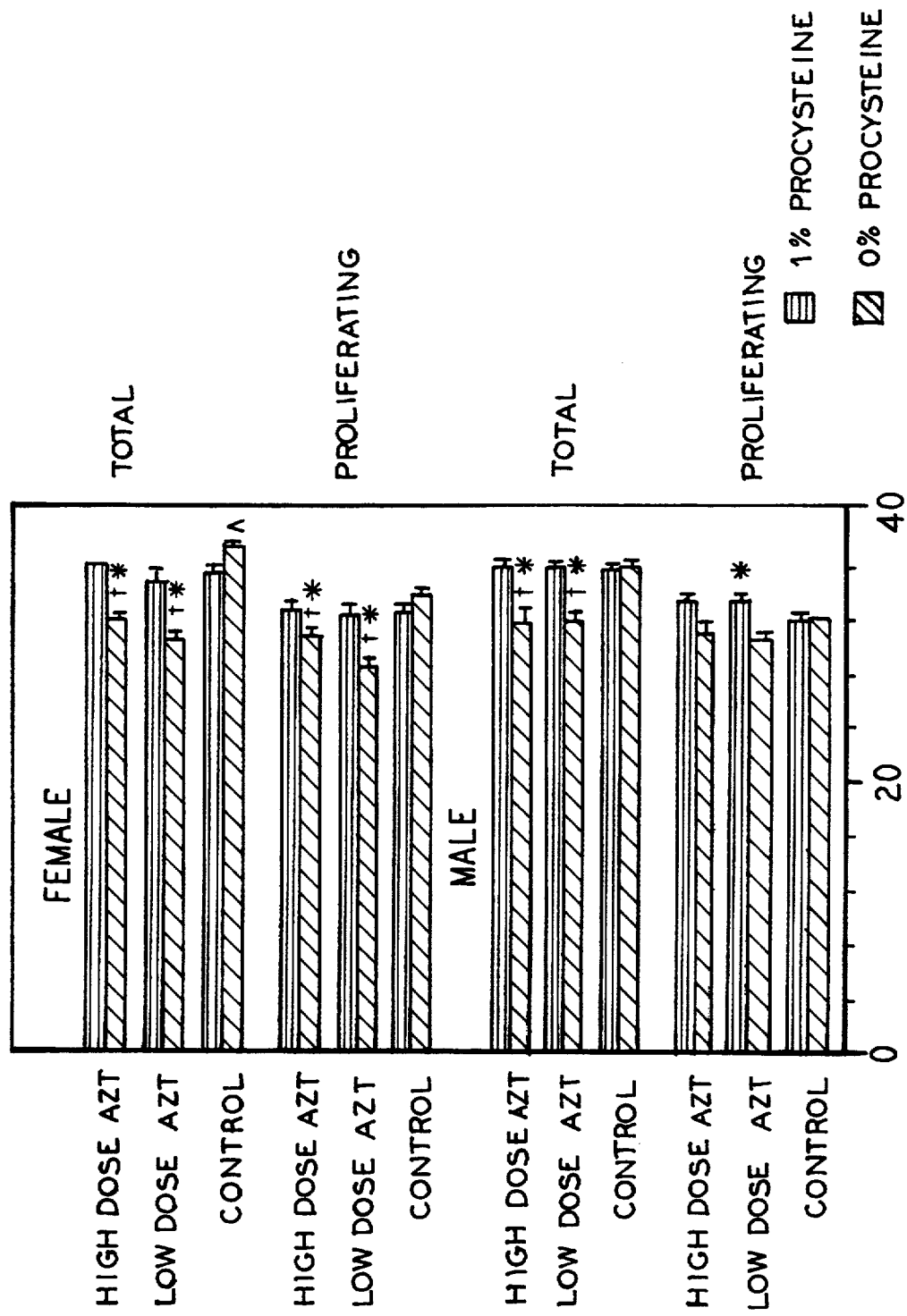

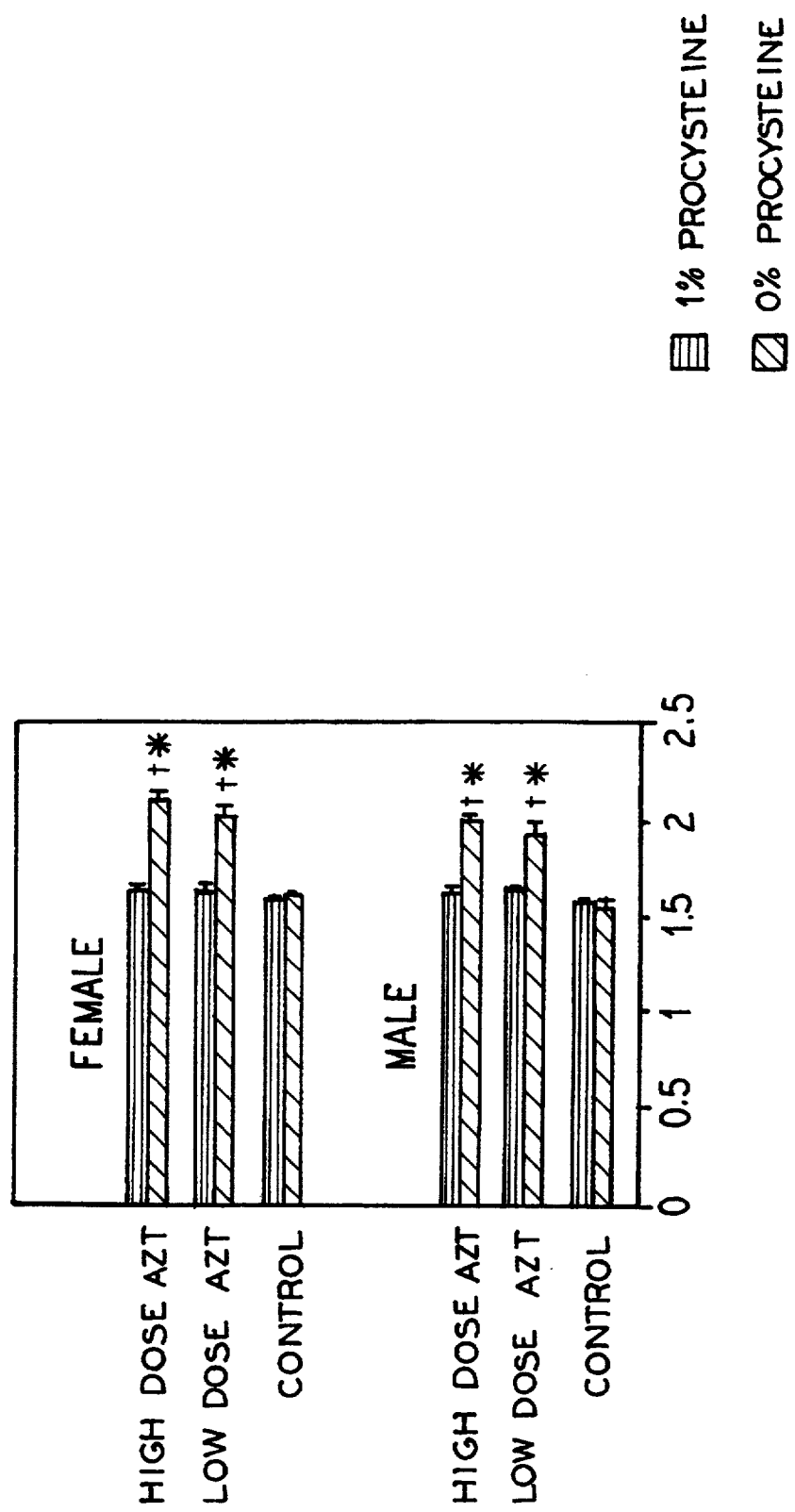

METHOD OF REDUCING OR PREVENTING BONE MARROW HYPOPLASIA

This is a continuation-in-part of U.S. patent application Ser. No. 07/872,549, filed Apr. 23, 1992, entitled: "METHOD FOR REDUCING OR PREVENTING TOXICITY ASSOCIATED WITH ANTIRETROVIRAL THERAPY."

BACKGROUND OF THE INVENTION

The present invention relates generally to the treatment of patients. More specifically, the present invention relates to reducing or preventing bone marrow hypoplasia.

Presently, 3'-Azidothymidine (AZT) is the primary therapy for the treatment of AIDS. AZT is an antiretroviral drug that is active against human immunodeficiency virus (HIV). In this regard, AZT is an inhibitor of the in vitro replication of some retroviruses, including HIV. AZT is marketed by the Burroughs Wellcome Company under the name Retrovir. Retrovir is the brand name for Zidovudine (formerly called azidothymidine (AZT)). See Physician Desk Reference, 44th Edition, 1990, pg. 799.

Recently, attention has been focussed on another potential treatment for AIDS using DDI. DDI is also an antiretroviral drug.

Unfortunately, AZT has a significant dose dependent toxicity. In fact, the 1990 PDR bears the following statement:

Warning Therapy with Retrovoir (Zidovudine) is often associated with hematologic toxicity including granulocytopenia and severe anemia requiring transfusions (see warnings).

AZT related bone marrow toxicity limits the utility of the drug. See, Thompson et al, "Hematologic Toxicity of AZT and ddC Administered as Single Agent and in Combination to Rats and Mice", Fundamental and Applied Toxicity, 17,159–176 (1991). Although the basis of the toxicity is not completely understood, some evidence suggests a metabolite of AZT, 3'-amino-3'-deoxythymidine (AMT), may be at least partially responsible. See, Cretton, "Catabolism of 3'-Azido-3'-deoxythymidine in Hepatocytes in Liver Microsomes, with Evidence of Formation of 3'-Amino-3'-deoxythymidine, a Highly Toxic Catabolite for Human Bone Marrow Cells", Molecular Pharmacology, 39:258–266. It has been reported that some thiols, including reduced glutathione, can reduce AZT to AMT in vivo. See, Handlon et al, "Thiol Reduction of 3'-Azidothymidine to 3'-Aminothymidine: Kinetics and Biomedical Implications", Pharmaceutical Research, Vol. 5, No. 5, 1988.

Additionally, long term administration of AZT can cause mitochondrial mycotoxicity. See, Lamperth et al, "Abnormal Skeletal and Cardiac Muscle Mitochondria Induced by Zidovudine (AZT) in Human Muscles In Vitro and in Animal Model" Laboratory Investigation, 1991, 65:742 This results in a myopathy that develops after a mean period of 12 months of therapy. Id.

Further adverse reactions have been reported with AZT. Additionally, DDI has been reported to also cause a variety of severe adverse reactions.

Due to the dose dependent toxicity of AZT and DDI the effectiveness of these drugs as therapies in treating AIDS has been limited.

Bone marrow hypoplasia can occur due to a number of reasons in addition to antiretroviral therapy. Although rare, aplastic or hypoplastic anemia is characterized by anemia with decrease of marrow mass. See, Merck Manual, page 1153.

Additionally, many insults or treatments can result in bone marrow hypoplasia. Chemotherapy, as well as radiation therapy, can cause bone marrow hypoplasia. Even non-chemotherapy and non-antiretroviral therapies have been implicated in individual cases of bone marrow hypoplasia (for example: antibiotics; anti-inflammatory drugs; and anti-convulsants). See, Merck Manual, page 1153.

Likewise, a number of chemical entities (e.g., benzene and inorganic arsenic) have been linked to bone marrow hypoplasia. Id. Still further, bone marrow hypoplasia may be found in the elderly. Id.

SUMMARY OF THE INVENTION

The present invention provides a method for reducing, or preventing, bone marrow hypoplasia. In this regard, the inventors have surprisingly found that when an intracellular glutathione stimulator is administered to a patient, who for example may be receiving an agent known to cause bone marrow hypoplasia, e.g., is receiving antiretroviral therapy, the incidence of bone marrow hypoplasia is reduced.

The present invention thereby provides a method for reducing or preventing bone marrow hypoplasia comprising the step of administering to a patient at risk of bone marrow hypoplasia, a therapeutically effective amount of a composition that stimulates the intracellular synthesis of glutathione. Additionally, it is believed the method can be used to treat a patient suffering from bone marrow hypoplasia.

In a preferred embodiment, the composition for stimulating the intracellular glutathione levels comprises L-2-oxothiazolidine-4-carboxylate.

In an embodiment, the patent is at risk of bone marrow hypoplasia due to antiretroviral therapy the patient is receiving.

In an embodiment, the patient is at risk of bone marrow hypoplasia due to anti-cancer therapy.

The present invention also provides a method for treating a patient who has bone marrow hypoplasia comprising the steps of administering to the patient an intracellular glutathione stimulator in a therapeutically sufficient amount.

An advantage of the present invention is that it reduces, or prevents, bone marrow hypoplasia associated with antiretroviral therapy. This allows compounds such as AZT to be more effectively used in the treatment of AIDS.

Moreover, an advantage of the present invention is that it provides a method that prevents or reduces bone marrow hypoplasia associated with chemotherapy.

Furthermore, an advantage of the present invention is that it prevents or reduces bone marrow hypoplasia associated with radiation therapy.

Still further, an advantage of the present invention is to provide a method for treating bone marrow hypoplasia.

Additional features and advantages of the present invention are described in, and will be apparent from, the detailed description of the presently preferred embodiments and from the drawings.

BRIEF DESCRIPTION OF THE DRAWINGS

FIGS. 1–7 illustrate, graphically, the results of experiments conducted in Example No. 2.

DETAILED DESCRIPTION OF THE PRESENTLY PREFERRED EMBODIMENTS

Figure 1:
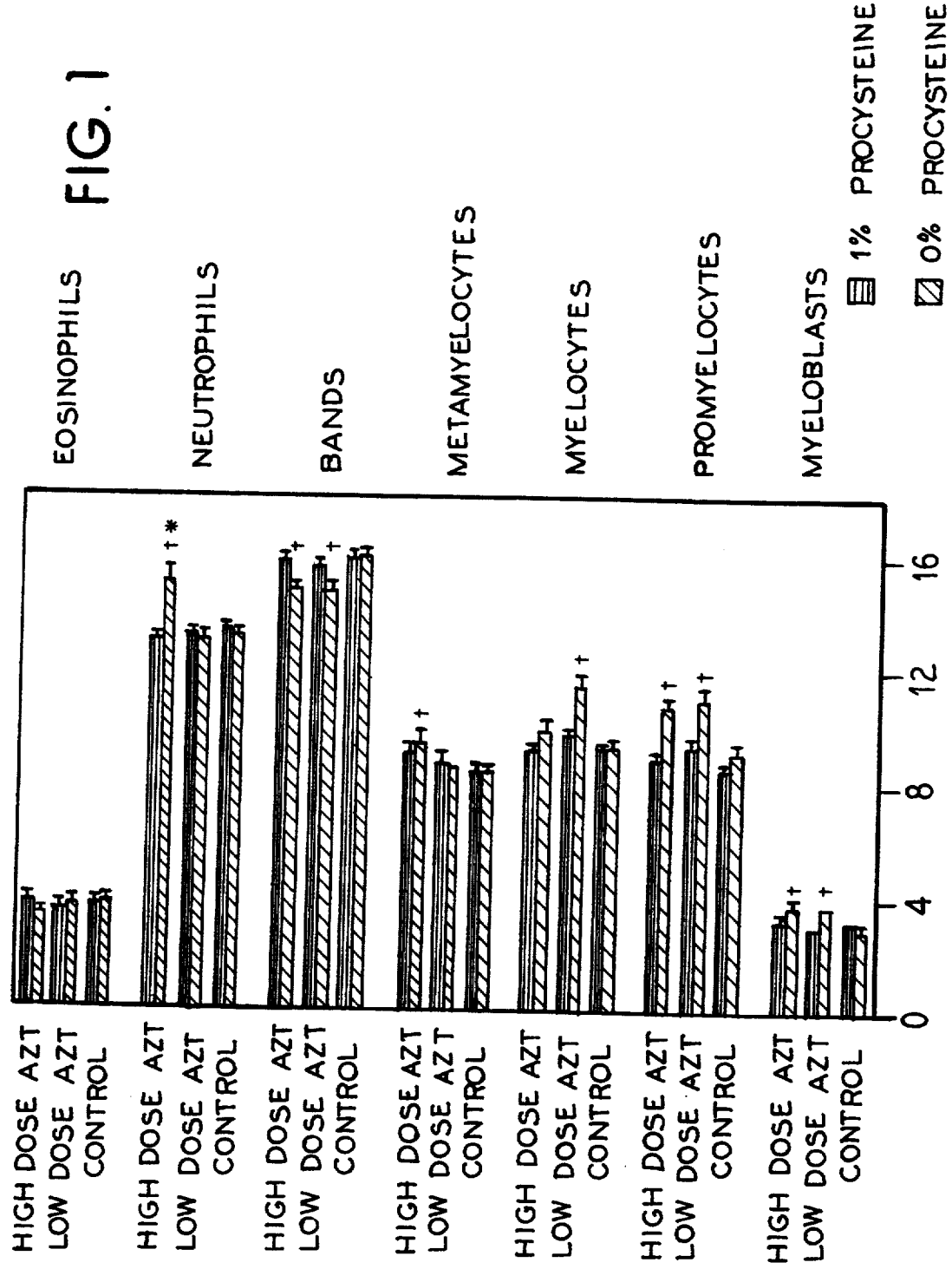

Bone marrow hypoplasia can occur due to a number of possible causes and insults. For example, the treatment of HIV and/or AIDS infection with antiretroviral therapy is limited due to the severe toxicity associated with such agents which includes bone marrow hypoplasia. AZT causes a dose dependent hematoxicity. DDI also induces severe life threatening adverse side effects. The toxicity of such antiretroviral agents is dose dependent thereby limiting the therapeutic approaches that can be taken with such compounds.

The inventors have also surprisingly found that an intracellular glutathione stimulator when administered to a patient at risk of bone marrow hypoplasia will reduce or prevent bone marrow hypoplasia. This will reduce or prevent the toxicity associated with antiretroviral therapy, such as AZT. This is a surprising result in view of the fact that it had been reported that reduced glutathione, and other thiols, may reduce AZT to AMT. See, Handlon et al, supra.

This belief, coupled with the evidence suggesting that AMT may be at least partially responsible for the bone marrow toxicity of AZT (see, Cretton, supra) would lead one away from such a combination. Surprisingly, the inventors have found that an intracellular glutathione stimulator will reduce the toxicity of AZT. As set forth in detail below in the experiment described in Example No. 1, the inventors have specifically found that L-2-oxothiazolidine-4-carboxylate will reduce the toxicity of AZT. Additionally, as illustrated in Example No. 2, the inventors have found that AZT-induced bone marrow hypoplasia is markedly improved by L-2-oxothiazolidine-4-carboxylate.

L-2-oxothiazolidine-4-carboxylate is subjected to the action of 5-oxo-L-prolinase in the presence of adenosine triphosphate to produce S-carboxyl cysteine. S-carboxyl cysteine is then decarboxylated to produce cysteine. Cysteine is then metabolized to provide glutathione. See, U.S. Pat. Nos.: 4,335,210; 4,434,158; 4,438,124; 4,665,082; and 4,647,571, the disclosures of which are incorporated herein by reference.

Likewise, esters of L-2-oxothiazolidine-4-carboxylate can be used. The ester can be saturated straight or branched, alkyl groups of 1 to 10 carbon atoms. Preferably, the ester is chosen from a saturated straight alkyl group such as methyl, ethyl, propyl, butyl, pentyl, hexyl, heptyl, octyl, nonyl, or decyl and a saturated branched alkyl group such as isopropyl, isobutyl, sec-butyl, tert-butyl, or isopenyl. Such esters are disclosed in U.S. Pat. No. 5,208,249, the disclosure of which is hereby incorporated herein by reference.

The inventors also believe that other substrates that stimulate intracellular glutathione synthesis can also be utilized to reduce, or prevent, bone marrow hypoplasia. To this end, the inventors believe that glutathione esters, as well as other thiazolidine-4-carboxylate analogs, that are converted intracellularly the glutathione can be utilized.

Such a glutathione ester, for example, can have the structure:

wherein: R is an alkyl group containing 1 to 10 carbon atoms. Preferably, the methyl and ethyl glutathione esters are used. Glutathione esters are disclosed in U.S. Pat. No. 4,710,489, the disclosure of which is incorporated herein by reference.

Further, the inventors postulate that proteins enriched in cysteine, that will also stimulate intracellular glutathione synthesis, can be utilized. Such proteins, if they have sufficiently high cysteine levels and are administered in sufficiently great quantities, it is believed, can provide the necessary intracellular glutathione stimulation. For example, the following proteins have a high cysteine content: whey (2%); egg white (2.5%); serum albumin (5.5%); and lactalbumin (5.8%).

Pursuant to the present invention, the composition of the present invention can either be administered parenterally or enterally. Enterally, the composition can comprise a pill including, for example, L-2-oxothiazolidine-4-carboxylate that is administered to a patient. If the treatment is to prevent or reduce bone marrow hypoplasia caused by a therapy, e.g., AZT, the composition can be administered either contemporaneously with the agent, e.g., antiretroviral drug, or on the same days. In a similar vein, if the patient is at risk of bone marrow hypoplasia due to radiation therapy or chemotherapy, the composition can be administered on the same day as the therapy, before, and/or after the therapy.

Of course, if the composition is being used to treat or prevent bone marrow hypoplasia due to, for example, aplastic anemia, the composition can be administered alone. Likewise, the composition in such cases can be administered enterally or parenterally. It is even envisioned that the composition can be part of the patients' diet.

Parenterally, the composition can, for example, include approximately 3% to about 6%, by weight, L-2-oxothiazolidine-4-carboxylate in a buffer solution such as phosphate buffer. Of course, parenterally, the composition can be administered as a bolus or as an additive to an IV solution. Again, a variety of treatment regimens are possible depending on the basis of the risk for the bone marrow hypoplasia.

By way of example, and not limitation, examples of the present invention will now be given.

EXAMPLE NO. 1

To evaluate the hematologic response (peripheral blood and bone marrow), mice were treated by gavage twice daily for 13.5 days with 3'-azido-3'-deoxythymidine (AZT) while being administered L-2-oxothiazolidine-4-carboxylate (Procysteine ®) orally with the feed.

L-2-oxothiazolidine-4-carboxylate (Procysteine ®), was provided by Clintec Nutrition Company, Deerfield, Ill. Diet (MEAL) containing 1.0% (wt/wt) Procysteine ® was formulated. The control diet consisted of MEAL containing no Procysteine ®.

3'-azido-3'-deoxythymidine (AZT) was provided by Sigma Chemical Company, St. Louis, Mo. AZT was formulated as a suspension at 2.5 and 25 mg/mL in sterile water containing 0.5% (wt/vol) methylcellulose. AZT formulations were dispensed into amber glass bottles.

0.5% (wt/vol) methylcellulose in sterile water was used as the vehicle control. The vehicle control was dispensed and handled in a similar fashion as the positive control article.

The control diet and diet containing Procysteine ® were stored at room temperature in sealed containers in the study room. While in a fume hood, the diet containing Procysteine ® was weighed and dispensed. In a fume hood, AZT was weighed, formulated into a suspension and dispensed into bottles.

The vehicle control and AZT formulations were stored refrigerated at 5°±3° C. At each gavage dosing period, one bottle of each of the formulations was removed from the refrigerator approximately 30-60 minutes before dosing and maintained with continual stirring using a magnetic stir bar until the completion of dosing. While in a fume hood, mice were treated by gavage twice a day, starting on study day 3.

Sixty male and sixty female mice from Charles River Laboratories, Portage, Mich., were studied. Mice were approximately 7-8 weeks old at the start of AZT dosing. On study day 0, the weight of the mice was as follows: males: 17-30 g; and females: 14-25 g. Only mice showing no signs of clinical illness were used in this study. The mice were from a colony which was raised and certified by the vendor to be free of adventitious pathogens as indicated upon receipt.

The experimental design for treating the animals was as shown in Table 1. Three days prior to the initiation of AZT treatment (i.e., on study days 0, 1, and 2), mice in groups 2, 5, and 6 were fed the diet containing 1.0% (wt/wt) Procysteine ®. Mice in groups 1, 3, and 4 were fed the control diet.

Treatment with these diets was continued on study days 3-16.

Starting on study day 3, mice in groups 1 and 2 were treated by oral gavage with a vehicle control (0.5% methyl-cellulose in distilled water) or, in groups 3, 4, 5, and 6, with a positive control article (AZT at 50 or 500 mg/kg body weight/day), as appropriate. Mice were weighed before the first treatment every day to calculate dosage. Mice were treated by gavage twice daily, starting at approximately 9 a.m. and 3 p.m., receiving ½ of the daily dose at each treatment. At each time point, mice were treated using a volume of approximately 10 mL/kg body weight.

Animals were weighed (not fasted) and sacrificed on study day 17. At this time, blood was collected for hematology evaluation, and bone marrow was collected for bone marrow and hematopoietic progenitor cell assays.

TABLE 1

Scheme for Treating Mice with AZT and Procysteine ®

| Group No. | AZT Daily Dosage[1] (mg/kg) (starting day 3) | Procysteine ® (% of Diet) (starting day 0) | No. Mice/Group (male/female) |
|---|---|---|---|
| 1 | 0 | 0 | 10/10 |
| 2 | 0 | 1.0 | 10/10 |
| 3 | 50 | 0 | 10/10 |
| 4 | 500 | 0 | 10/10 |
| 5 | 50 | 1.0 | 10/10 |
| 6 | 500 | 1.0 | 10/10 |

[1] AZT was given by gavage at ½ the daily dosage, twice daily for 14 days in a volume of 10 mL/kg body weight. AZT was formulated at 2.5 amd 25 mg/mL for the 50 and 500 mg/kg body weight treatments, respectively.

Mice received Certified Rodent Diet—MEAL (Ralston Purina Co., St. Louis, Mo.). Three days prior to the initiation of AZT, mice in groups 2, 5, and 6 were placed on diet containing 1.0% (wt/wt) Procysteine ®. The diet was put into dishes placed in each cage. Food consumption was monitored on a daily basis for all animals within a block upon the initiation of Procysteine ® feeding to animals within that block.

Deionized drinking water was provided and libitum through demand-controlled valves in each cage.

To accommodate the necropsy procedure, animals were assigned to 1 of 5 blocks (24 mice/block) with initiation of treatment occurring on 5 consecutive days (i.e., study day 0 for block 2 is one day after study day 0 for block 1, and so on) (see Table 2). Male mice were numbered from 1 through 60, female mice from 61 through 120, according to their body weight on study day 0 for block 1. For a given sex of animal, the heavier the animal, the smaller the number assigned. The assignment kept constant the sum of the numbers (ranks) across the 2 animals in each group of a block for a given sex. Those sums differed from block to block by an increment of 4. Such a small difference due to blocks was controlled in the statistical analysis. The main goal of this systematic assignment was to maintain equal weights across groups. The assignment of animals to treatment groups (5 blocks) is given in Table 2.

Mice were treated and necropsied according to block, in ascending group order; per block, males were treated first, followed by females. For example, Procysteine ®treatment started for block 1 on study day 0; the next day was study day 1 for block 1 and study day 0 for block 2, and so on. At any given gavage period (a.m. or p.m.), all males and females of a given block were treated before mice from the next block were started.

TABLE 2

| Group | Sex | Systematic Assignment of Animals | | | | |
|---|---|---|---|---|---|---|
| | | 1 | 2 | 3 | 4 | 5 |
| 1 | M | 01, 52 | 13, 44 | 25, 36 | 07, 58 | 19, 50 |
| | F | 61, 112 | 72, 104 | 85, 96 | 67, 118 | 79, 110 |
| 2 | M | 12, 41 | 24, 33 | 06, 55 | 18, 47 | 30, 39 |
| | F | 72, 101 | 84, 93 | 66, 115 | 78, 107 | 90, 99 |
| 3 | M | 21, 32 | 03, 54 | 15, 46 | 27, 38 | 09, 60 |
| | F | 81, 92 | 63, 114 | 75, 106 | 87, 98 | 69, 120 |
| 4 | M | 02, 51 | 14, 43 | 26, 35 | 08, 57 | 20, 49 |
| | F | 62, 111 | 74, 103 | 86, 95 | 68, 117 | 80, 109 |
| 5 | M | 11, 42 | 23, 34 | 05, 56 | 17, 48 | 29, 40 |
| | F | 71, 102 | 83, 94 | 65, 116 | 77, 108 | 89, 100 |
| 6 | M | 22, 31 | 04, 53 | 15, 45 | 28, 37 | 10, 50 |
| | F | 82, 91 | 64, 113 | 76, 105 | 88, 97 | 70, 119 |
| Sum of Ranks | M | 53 | 57 | 61 | 65 | 65 |
| | F | 173 | 117 | 181 | 185 | 189 |

At approximately 3:00 p.m. on study day 0, animals were placed on a measured amount of diet (at least approximately 11 g/day) containing 0 or 1% Procysteine ®, as appropriate. Feed was administered in stainless steel dishes placed in each cage. At approximately 7:00 a.m. on each of the succeeding days, the feed containers were removed, weighed, cleaned, and fresh diet added; containers were returned to the cages at approximately 3:00 p.m. each day except study day 17. On study days 3-16, each animal was treated by gavage twice daily, starting at approximately 9:00 a.m. and 3:00 p.m., with approximately 10 mL/kg body weight of the vehicle control, or the positive control (AZT) at 50 or 500 mg/kg body weight.

Starting on study day 0, body weights were recorded daily.

Each animal was observed approximately 1 hour after being treated by gavage.

On study day 17, the animals were anesthetized with methoxyflurane (in a bell jar). When deeply anesthetized, blood was obtained by cardiac puncture and transferred for hematological analysis into tubes containing an EDTA suspension.

Bone marrow smear slides were prepared by extracting a small quantity of bone marrow from a femur using a small brush previously dipped in mouse serum and then brushing the marrow onto the slides. The bone marrow slides were dipped (five times for approximately one second each time) into Diff-Quik ®fixative and allowed to air dry. Prepared slides were stained and evaluated microscopically.

The following hematologic assays were conducted.
Leukocyte count
Erythrocyte count
Total hemoglobin concentration
Hematocrit
Mean corpuscular volume (MCV)
Mean corpuscular hemoglobin (MCH)
Mean corpuscular hemoglobin concentration (MCHC)
Platelet count
Reticulocyte count
Differential leukocyte count Populations of bone marrow colony forming cells were evaluated. Bone marrow was collected and the stem cell assay conducted, as follows: one femur per mouse was cut at the distal and proximal ends. Using a syringe and 25 gauge needle, 5 mL of IMDM media was flushed through the femur into a collection tube (2.5 mL flushed into one end, then 2.5 ml into the other end). The tube was washed using Iscove's Modified Dulbecco's Media containing 20% fetal bovine serum and the cell concentration was adjusted to the desired count for the colony assay.

In triplicate, the marrow cells were put into a mixture of methylcellulose and plated into 35 mm diameter dishes. The dishes were incubated approximately 2 weeks (37° C., 5% $CO_2$, 100% relative humidity) then manually scored under a microscope for myeloid, erythroid, and mixed colonies.

Data generated included the following:
Body weights: Initial and daily
Hematology: Blood collected prior to necropsy
Bone marrow: Bone marrow count, Myeloid/Erythroid ratio, hematopoietic progenitor population
Food consumption: Daily Statistical tests were performed at the $\alpha$ level of 0.01. Listing of the individual data and summary statistics (mean, standard error and sample size) was provided. The average body weight changes from study day 3 for study days 4-10 and 11-17 and average food consumption for study days 4-10 and 11-17 was analyzed. Since the groups consist of various dosages of AZT and procysteine ®, appropriate dosage response models were established. Specifically, the interaction of AZT and procysteine ® was evaluated.

TABLE 3

Body Weight Changes
Listing of Means and Standard Errors: Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AXT | 0 mg/kg | 0 mg/kg | 50 mg/kg | 500 mg/kg | 50 mg/kg | 500 mg/kg | AZT DR at % Procyst. | | | mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| Weight Change Week 1 (g) | | | | | | | | | | | | | |
| Male | | | | | | | | | | | | | |
| Mean | 1.1 | 1.4 | 1.1 | 0.8 | 1.3 | 1.0 | | | | | | | |
| Std. Err. | 0.2 | 0.3 | 0.3 | 0.2 | 0.3 | 0.2 | | | | | | | |
| N | 10 | 10 | 10 | 10 | 10 | 10 | | | | | | | |
| Female | | | | | | | | | | | | | |
| Mean | 1.0 | 1.1 | 1.0 | 0.6 | 1.0 | 0.9 | | | | | | | |
| Std. Err. | 0.2 | 0.1 | 0.1 | 0.2 | 0.2 | 0.2 | | | | | | | |
| N | 10 | 10 | 10 | 10 | 10 | 10 | | | | | | | |
| Combined | | | | | | | | | | | | | |
| Mean | 1.1 | 1.3— | 1.1—— | 0.7—# | 1.1—— | 1.0—— | — | — | — | — | — | — | — |
| Std. Err. | 0.1 | 0.2 | 0.2 | 0.1 | 0.2 | 0.1 | | | | | | | |
| N | 20 | 20 | 20 | 20 | 20 | 20 | | | | | | | |
| Weight Change Week 2 (g) | | | | | | | | | | | | | |
| Male | | | | | | | | | | | | | |
| Mean | 2.4 | 2.5 | 2.5 | 2.1 | 2.3 | 1.9 | | | | | | | |
| Std. Err. | 0.2 | 0.3 | 0.4 | 0.3 | 0.3 | 0.2 | | | | | | | |
| N | 10 | 10 | 10 | 10 | 10 | 10 | | | | | | | |
| Female | | | | | | | | | | | | | |
| Mean | 1.8 | 1.8 | 1.8 | 1.5 | 1.8 | 1.8 | | | | | | | |
| Std. Err. | 0.2 | 0.2 | 0.2 | 0.2 | 0.2 | 0.2 | | | | | | | |
| N | 10 | 10 | 10 | 10 | 9 | 10 | | | | | | | |
| Combined | | | | | | | | | | | | | |
| Mean | 2.1 | 2.2— | 2.2—— | 1.8—— | 2.1—— | 1.9—— | — | — | — | — | — | — | — |
| Std. Err. | 0.1 | 0.2 | 0.2 | 0.2 | 0.2 | 0.1 | | | | | | | |

TABLE 3-continued

Body Weight Changes
Listing of Means and Standard Errors: Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AXT | 0 mg/kg | 0 mg/kg | 50 mg/kg | 500 mg/kg | 50 mg/kg | 500 mg/kg | AZT DR at % Procyst. | | | mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| N | 20 | 20 | 20 | 20 | 19 | 20 | | | | | | | |

@ Indicates Difference From Group 1: 0 mg/kg AZT, 0.0% Procysteine
Indicates Difference From Group 2: 0 mg/kg AZT, 1.0% Procysteine
— Indicates Not Significant DR, DIF or Comparison to Group 1 or 2
D Indicates Decreasing DR
I Indicates Increasing DR
* Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 Indicate Sexes Did Not Differ Therefore Tests Are Performed Across Sex

TABLE 4

Blood Assays
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| WBC ($\times 10^{}3/uL$)** | | | | | | | | | | | | | |
| Male | | | | | | | | | | | | | |
| Mean | 1.7 | 1.9 | 1.6 | 2.3 | 1.6 | 2.1 | | | | | | | |
| Std. Err. | 0.3 | 0.2 | 0.2 | 0.3 | 0.1 | 0.2 | | | | | | | |
| N | 10 | 10 | 10 | 10 | 10 | 10 | | | | | | | |
| Female | | | | | | | | | | | | | |
| Mean | 2.1 | 1.6 | 1.7 | 2.3 | 2.0 | 1.6 | | | | | | | |
| Std. Err. | 0.2 | 0.1 | 0.2 | 0.2 | 0.2 | 0.2 | | | | | | | |
| N | 10 | 9 | 10 | 10 | 9 | 10 | | | | | | | |
| Combined | | | | | | | | | | | | | |
| Mean | 1.9 | 1.7- | 1.7-- | 2.3-# | 1.8-- | 1.9-- | - | - | - | - | - | - | - |
| Std. Err. | 0.2 | 0.1 | 0.1 | 0.2 | 0.1 | 0.1 | | | | | | | |
| N | 20 | 19 | 20 | 20 | 19 | 20 | | | | | | | |
| RBC ($\times 10^{}6/uL$)** | | | | | | | | | | | | | |
| Male | | | | | | | | | | | | | |
| Mean | 7.46 | 7.46 | 6.95 | 6.18 | 7.13 | 6.19 | | | | | | | |
| Std. Err. | 0.06 | 0.03 | 0.05 | 0.08 | 0.08 | 0.11 | | | | | | | |
| N | 10 | 10 | 10 | 10 | 10 | 10 | | | | | | | |
| Female | | | | | | | | | | | | | |
| Mean | 7.25 | 7.36 | 6.77 | 6.22 | 6.99 | 6.29 | | | | | | | |
| Std. Err. | 0.07 | 0.06 | 0.04 | 0.10 | 0.10 | 0.05 | | | | | | | |
| N | 10 | 9 | 10 | 10 | 9 | 10 | | | | | | | |
| Combined | | | | | | | | | | | | | |
| Mean | 7.36 | 7.41- | 6.86@# | 6.20@# | 7.07@# | 6.24@# | D | D | - | - | I | - | - |
| Std. Err. | 0.05 | 0.04 | 0.04 | 0.07 | 0.06 | 0.06 | | | | | | | |
| N | 20 | 19 | 20 | 20 | 19 | 20 | | | | | | | |
| NGB (g/L) | | | | | | | | | | | | | |
| Male | | | | | | | | | | | | | |
| Mean | 13.2 | 13.2 | 12.6 | 11.5 | 13.0 | 11.5 | | | | | | | |
| Std. Err. | 0.1 | 0.1 | 0.1 | 0.2 | 0.1 | 0.2 | | | | | | | |
| N | 10 | 10 | 10 | 10 | 10 | 10 | | | | | | | |
| Female | | | | | | | | | | | | | |
| Mean | 13.0 | 13.0 | 12.5 | 11.7 | 12.9 | 11.7 | | | | | | | |
| Std. Err. | 0.1 | 0.1 | 0.1 | 0.2 | 0.2 | 0.2 | | | | | | | |
| N | 10 | 9 | 10 | 10 | 9 | 10 | | | | | | | |
| Combined | | | | | | | | | | | | | |
| Mean | 13.1 | 13.1- | 12.5@# | 11.6@# | 12.9-- | 11.6@# | D | D | - | - | I | - | - |
| Std. Err. | 0.1 | 0.1 | 0.1 | 0.1 | 0.1 | 0.1 | | | | | | | |
| N | 20 | 19 | 20 | 20 | 19 | 20 | | | | | | | |
| NCT (%) | | | | | | | | | | | | | |
| Male | | | | | | | | | | | | | |
| Mean | 37.4 | 37.0 | 36.0 | 33.0 | 36.8 | 33.2 | | | | | | | |
| Std. Err. | 0.4 | 0.3 | 0.3 | 0.5 | 0.5 | 0.7 | | | | | | | |
| N | 10 | 10 | 10 | 10 | 10 | 10 | | | | | | | |
| Female | | | | | | | | | | | | | |
| Mean | 36.1 | 35.9 | 34.4 | 32.1 | 35.2 | 32.5 | | | | | | | |
| Std. Err. | 0.4 | 0.4 | 0.3 | 0.5 | 0.5 | 0.5 | | | | | | | |
| N | 10 | 9 | 10 | 10 | 9 | 10 | | | | | | | |
| Combined | | | | | | | | | | | | | |

TABLE 4-continued

Blood Assays
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| Mean | 36.8 | 36.5- | 35.2@# | 32.5@# | 36.0-- | 32.8@# | D | D | - | - | - | - | - |
| Std. Err. | 0.3 | 0.2 | 0.3 | 0.4 | 0.4 | 0.4 | | | | | | | |
| N | 20 | 19 | 20 | 20 | 19 | 20 | | | | | | | |
| | | | | MCV (fL) | | | | | | | | | |
| *Male* | | | | | | | | | | | | | |
| Mean | 51 | 51 | 52 | 54 | 52 | 54 | | | | | | | |
| Std. Err. | 0 | 0 | 0 | 0 | 0 | 0 | | | | | | | |
| N | 10 | 10 | 10 | 10 | 10 | 10 | | | | | | | |
| *Female* | | | | | | | | | | | | | |
| Mean | 50 | 49 | 51 | 52 | 51 | 52 | | | | | | | |
| Std. Err. | 0 | 0 | 0 | 0 | 0 | 1 | | | | | | | |
| N | 10 | 9 | 10 | 10 | 9 | 10 | | | | | | | |
| *Combined* | | | | | | | | | | | | | |
| Mean | 51 | 50- | 52@# | 53@# | 52@# | 53@# | I | I | - | - | - | - | - |
| Std. Err. | 0 | 0 | 0 | 0 | 0 | 0 | | | | | | | |
| N | 20 | 19 | 20 | 20 | 19 | 20 | | | | | | | |
| | | | | MCH (pg) | | | | | | | | | |
| *Male* | | | | | | | | | | | | | |
| Mean | 17.6 | 17.7 | 18.2 | 18.6 | 18.3 | 18.6 | | | | | | | |
| Std. Err. | 0.1 | 0.1 | 0.1 | 0.2 | 0.1 | 0.1 | | | | | | | |
| N | 10 | 10 | 10 | 10 | 10 | 10 | | | | | | | |
| *Female* | | | | | | | | | | | | | |
| Mean | 18.0 | 17.6 | 18.4 | 18.8 | 18.4 | 18.6 | | | | | | | |
| Std. Err. | 0.2 | 0.1 | 0.1 | 0.2 | 0.2 | 0.2 | | | | | | | |
| N | 10 | 9 | 10 | 10 | 9 | 10 | | | | | | | |
| *Combined* | | | | | | | | | | | | | |
| Mean | 17.8 | 17.7- | 18.3@# | 18.7@# | 18.3@# | 18.6@# | I | I | - | - | - | - | - |
| Std. Err. | 0.1 | 0.1 | 0.1 | 0.1 | 0.1 | 0.1 | | | | | | | |
| N | 20 | 19 | 20 | 20 | 19 | 20 | | | | | | | |
| | | | | MCHC (g/dL) | | | | | | | | | |
| *Male* | | | | | | | | | | | | | |
| Mean | 35.2 | 35.7 | 35.1 | 34.8 | 35.5 | 34.7 | | | | | | | |
| Std. Err. | 0.4 | 0.3 | 0.2 | 0.3 | 0.2 | 0.3 | | | | | | | |
| N | 10 | 10 | 10 | 10 | 10 | 10 | | | | | | | |
| *Female* | | | | | | | | | | | | | |
| Mean | 36.1 | 36.2 | 36.3 | 36.4 | 36.5 | 36.1 | | | | | | | |
| Std. Err. | 0.3 | 0.2 | 0.3 | 0.3 | 0.3 | 0.3 | | | | | | | |
| N | 10 | 9 | 10 | 10 | 9 | 10 | | | | | | | |
| *Combined* | | | | | | | | | | | | | |
| Mean | 35.7 | 35.9- | 35.7-- | 35.6-- | 35.9-- | 35.4-- | - | - | - | - | - | - | - |
| Std. Err. | 0.3 | 0.2 | 0.2 | 0.3 | 0.2 | 0.3 | | | | | | | |
| N | 20 | 19 | 20 | 20 | 19 | 20 | | | | | | | |
| | | | | Platelets ($\times 10^{**}3$/UL) | | | | | | | | | |
| *Male* | | | | | | | | | | | | | |
| Mean | 969 | 1045 | 949 | 1119 | 999 | 1205 | | | | | | | |
| Std. Err. | 68 | 85 | 34 | 63 | 59 | 44 | | | | | | | |
| N | 9 | 10 | 10 | 10 | 10 | 10 | | | | | | | |
| *Female* | | | | | | | | | | | | | |
| Mean | 935 | 878 | 972 | 1082 | 836 | 934 | | | | | | | |
| Std. Err. | 59 | 79 | 67 | 79 | 68 | 60 | | | | | | | |
| N | 10 | 9 | 10 | 10 | 9 | 9 | | | | | | | |
| *Combined* | | | | | | | | | | | | | |
| Mean | 951 | 966- | 961-- | 1101@# | 922-- | 1077-- | - | - | - | - | - | - | - |
| Std. Err. | 60 | 37 | 49 | 47 | 48 | 19 | | | | | | | |
| N | 19 | 19 | 20 | 20 | 19 | 19 | | | | | | | |
| | | | | Lymphocytes (%) | | | | | | | | | |
| *Male* | | | | | | | | | | | | | |
| Mean | 62 | 62 | 65 | 63 | 66 | 58 | | | | | | | |
| Std. Err. | 4 | 3 | 5 | 2 | 2 | 4 | | | | | | | |
| N | 10 | 10 | 10 | 10 | 10 | 10 | | | | | | | |
| *Female* | | | | | | | | | | | | | |
| Mean | 77 | 72 | 76 | 72 | 74 | 76 | | | | | | | |
| Std. Err. | 1 | 2 | 2 | 2 | 3 | 2 | | | | | | | |
| N | 10 | 9 | 10 | 10 | 9 | 10 | | | | | | | |
| *Combined* | | | | | | | | | | | | | |
| Mean | 69 | 67- | 70-- | 67-- | 70-- | 67-- | - | - | - | - | - | - | - |
| Std. Err. | 3 | 2 | 3 | 2 | 2 | 3 | | | | | | | |
| N | 20 | 19 | 20 | 20 | 19 | 20 | | | | | | | |
| | | | | Neutrophils (%) | | | | | | | | | |

TABLE 4-continued

Blood Assays
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT<br>Procysteine | 0 mg/kg<br>0.0% | 0 mg/kg<br>1.0% | 50 mg/kg<br>0.0% | 500 mg/kg<br>0.0% | 50 mg/kg<br>1.0% | 500 mg/kg<br>1.0% | AZT DR at<br>% Procyst. | | | Procysteine DR at<br>mg/kg AZT | | | |
|---|---|---|---|---|---|---|---|---|---|---|---|---|---|
| | | | | | | | 0.0 | 1.0 | DIF | 0 | 50 | 500 | DIF |
| Male | | | | | | | | | | | | | |
| Mean | 35 | 34 | 32 | 32 | 31 | 38 | | | | | | | |
| Std. Err. | 4 | 3 | 5 | 2 | 2 | 5 | | | | | | | |
| N | 10 | 10 | 10 | 10 | 10 | 10 | | | | | | | |
| Female | | | | | | | | | | | | | |
| Mean | 20 | 23 | 19 | 24 | 24 | 20 | | | | | | | |
| Std. Err. | 2 | 3 | 2 | 2 | 3 | 2 | | | | | | | |
| N | 10 | 9 | 10 | 10 | 9 | 10 | | | | | | | |
| Combined | | | | | | | | | | | | | |
| Mean | 28 | 29- | 25-- | 28-- | 27-- | 29-- | - | - | - | - | - | - | - |
| Std. Err. | 3 | 2 | 3 | 2 | 2 | 3 | | | | | | | |
| N | 20 | 19 | 20 | 20 | 19 | 20 | | | | | | | |
| | | | | Eosinophils (%) | | | | | | | | | |
| Male | | | | | | | | | | | | | |
| Mean | 2 | 3 | 3 | 3 | 2 | 3 | | | | | | | |
| Std. Err. | 1 | 1 | 1 | 1 | 0 | 1 | | | | | | | |
| N | 10 | 10 | 10 | 10 | 10 | 10 | | | | | | | |
| Female | | | | | | | | | | | | | |
| Mean | 2 | 3 | 4 | 4 | 2 | 4 | | | | | | | |
| Std. Err. | 0 | 1 | 0 | 1 | 0 | 1 | | | | | | | |
| N | 10 | 9 | 10 | 10 | 9 | 10 | | | | | | | |
| Combined | | | | | | | | | | | | | |
| Mean | 2 | 3- | 3-- | 3-- | 2-- | 3-- | - | - | - | - | - | - | - |
| Std. Err. | 0 | 0 | 0 | 0 | 0 | 1 | | | | | | | |
| N | 20 | 19 | 20 | 20 | 19 | 20 | | | | | | | |
| | | | | Monocytes (%) | | | | | | | | | |
| Male | | | | | | | | | | | | | |
| Mean | 1 | 1 | 1 | 2 | 1 | 2 | | | | | | | |
| Std. Err. | 0 | 0 | 0 | 1 | 0 | 0 | | | | | | | |
| N | 10 | 10 | 10 | 10 | 10 | 10 | | | | | | | |
| Female | | | | | | | | | | | | | |
| Mean | 1 | 1 | 1 | 1 | 1 | 1 | | | | | | | |
| Std. Err. | 0 | 0 | 0 | 0 | 0 | 0 | | | | | | | |
| N | 10 | 9 | 10 | 10 | 9 | 10 | | | | | | | |
| Combined | | | | | | | | | | | | | |
| Mean | 1 | 1- | 1-- | 1-- | 1-- | 1-- | - | - | - | - | - | - | - |
| Std. Err. | 0 | 0 | 0 | 0 | 0 | 0 | | | | | | | |
| N | 20 | 19 | 20 | 20 | 19 | 20 | | | | | | | |
| | | | | Basophils (%) | | | | | | | | | |
| Male | | | | | | | | | | | | | |
| Mean | 0 | 0 | 0 | 0 | 0 | 0 | | | | | | | |
| Std. Err. | 0 | 0 | 0 | 0 | 0 | 0 | | | | | | | |
| N | 10 | 10 | 10 | 10 | 10 | 10 | | | | | | | |
| Female | | | | | | | | | | | | | |
| Mean | 0 | 0 | 0 | 0 | 0 | 0 | | | | | | | |
| Std. Err. | 0 | 0 | 0 | 0 | 0 | 0 | | | | | | | |
| N | 10 | 9 | 10 | 10 | 9 | 10 | | | | | | | |
| Combined | | | | | | | | | | | | | |
| Mean | 0 | 0- | 0-- | 0-- | 0-- | 0-- | - | - | - | - | - | - | - |
| Std. Err. | 0 | 0 | 0 | 0 | 0 | 0 | | | | | | | |
| N | 20 | 19 | 20 | 20 | 19 | 20 | | | | | | | |
| | | | | Bands (%) | | | | | | | | | |
| Male | | | | | | | | | | | | | |
| Mean | 0 | 0 | 0 | 0 | 0 | 0 | | | | | | | |
| Std. Err. | 0 | 0 | 0 | 0 | 0 | 0 | | | | | | | |
| N | 10 | 10 | 10 | 10 | 10 | 10 | | | | | | | |
| Female | | | | | | | | | | | | | |
| Mean | 0 | 0 | 0 | 0 | 0 | 0 | | | | | | | |
| Std. Err. | 0 | 0 | 0 | 0 | 0 | 0 | | | | | | | |
| N | 10 | 9 | 10 | 10 | 9 | 10 | | | | | | | |
| Combined | | | | | | | | | | | | | |
| Mean | 0 | 0- | 0-- | 0-- | 0-- | 0-- | - | - | - | - | - | - | |
| Std. Err. | 0 | 0 | 0 | 0 | 0 | 0 | | | | | | | |
| N | 20 | 19 | 20 | 20 | 19 | 20 | | | | | | | |
| | | | | NRBC (/100 WBC) | | | | | | | | | |
| Male | | | | | | | | | | | | | |
| Mean | 0 | 0 | 0 | 0 | 0 | 0 | | | | | | | |
| Std. Err. | 0 | 0 | 0 | 0 | 0 | 0 | | | | | | | |
| N | 10 | 10 | 10 | 10 | 10 | 10 | | | | | | | |

TABLE 4-continued

Blood Assays
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| Female | | | | | | | | | | | | | |
| Mean | 0 | 0 | 0 | 0 | 0 | 0 | | | | | | | |
| Std. Err. | 0 | 0 | 0 | 0 | 0 | 0 | | | | | | | |
| N | 10 | 9 | 10 | 10 | 9 | 10 | | | | | | | |
| Combined | | | | | | | | | | | | | |
| Mean | 0 | 0-- | 0-- | 0-- | 0-- | 0-- | -- | -- | -- | -- | -- | -- | -- |
| Std. Err. | 0 | 0 | 0 | 0 | 0 | 0 | | | | | | | |
| N | 20 | 19 | 20 | 20 | 19 | 20 | | | | | | | |
| | | | | Aniso (coded) | | | | | | | | | |
| Male | | | | | | | | | | | | | |
| Mean | 0.2 | 0.1 | 0.3 | 0.7 | 0.1 | 0.5 | | | | | | | |
| Std. Err. | 0.1 | 0.1 | 0.1 | 0.1 | 0.1 | 0.1 | | | | | | | |
| N | 10 | 10 | 10 | 10 | 10 | 10 | | | | | | | |
| Female | | | | | | | | | | | | | |
| Mean | 0.1 | 0.1 | 0.2 | 0.7 | 0.1 | 0.5 | | | | | | | |
| Std. Err. | 0.1 | 0.1 | 0.1 | 0.1 | 0.1 | 0.1 | | | | | | | |
| N | 10 | 9 | 10 | 10 | 9 | 10 | | | | | | | |
| Combined | | | | | | | | | | | | | |
| Mean | 0.1 | 0.1- | 0.2-- | 0.7@# | 0.1-- | 0.5@# | I | I | -- | -- | -- | -- | -- |
| Std. Err. | 0.0 | 0.0 | 0.1 | 0.1 | 0.0 | 0.1 | | | | | | | |
| N | 20 | 19 | 20 | 20 | 19 | 20 | | | | | | | |
| | | | | Micro (coded) | | | | | | | | | |
| Male | | | | | | | | | | | | | |
| Mean | 0.0 | 0.0 | 0.1 | 0.0 | 0.0 | 0.1 | | | | | | | |
| Std. Err. | 0.0 | 0.0 | 0.1 | 0.0 | 0.0 | 0.1 | | | | | | | |
| N | 10 | 10 | 10 | 10 | 10 | 10 | | | | | | | |
| Female | | | | | | | | | | | | | |
| Mean | 0.0 | 0.0 | 0.0 | 0.0 | 0.0 | 0.1 | | | | | | | |
| Std. Err. | 0.0 | 0.0 | 0.0 | 0.0 | 0.0 | 0.1 | | | | | | | |
| N | 10 | 9 | 10 | 10 | 9 | 10 | | | | | | | |
| Combined | | | | | | | | | | | | | |
| Mean | 0.0 | 0.0- | 0.0-- | 0.0-- | 0.0-- | 0.1-- | -- | -- | -- | -- | -- | -- | -- |
| Std. Err. | 0.0 | 0.0 | 0.0 | 0.0 | 0.0 | 0.0 | | | | | | | |
| N | 20 | 19 | 20 | 20 | 19 | 20 | | | | | | | |
| | | | | Macro (coded) | | | | | | | | | |
| Male | | | | | | | | | | | | | |
| Mean | 0.0 | 0.0 | 0.0 | 0.2 | 0.0 | 0.2 | | | | | | | |
| Std. Err. | 0.0 | 0.0 | 0.0 | 0.1 | 0.0 | 0.1 | | | | | | | |
| N | 10 | 10 | 10 | 10 | 10 | 10 | | | | | | | |
| Female | | | | | | | | | | | | | |
| Mean | 0.0 | 0.0 | 0.0 | 0.1 | 0.0 | 0.1 | | | | | | | |
| Std. Err. | 0.0 | 0.0 | 0.0 | 0.1 | 0.0 | 0.1 | | | | | | | |
| N | 10 | 9 | 10 | 10 | 9 | 10 | | | | | | | |
| Combined | | | | | | | | | | | | | |
| Mean | 0.0 | 0.0- | 0.0-- | 0.2@# | 0.0-- | 0.1-- | -- | -- | -- | -- | -- | -- | -- |
| Std. Err. | 0.0 | 0.0 | 0.0 | 0.1 | 0.0 | 0.0 | | | | | | | |
| N | 20 | 19 | 20 | 20 | 19 | 20 | | | | | | | |
| | | | | Poly (coded) | | | | | | | | | |
| Male | | | | | | | | | | | | | |
| Mean | 0.7 | 0.8 | 0.9 | 1.0 | 0.7 | 0.8 | | | | | | | |
| Std. Err. | 0.1 | 0.1 | 0.1 | 0.1 | 0.1 | 0.1 | | | | | | | |
| N | 10 | 10 | 10 | 10 | 10 | 10 | | | | | | | |
| Female | | | | | | | | | | | | | |
| Mean | 0.6 | 0.6 | 0.7 | 0.8 | 0.8 | 0.8 | | | | | | | |
| Std. Err. | 0.1 | 0.1 | 0.1 | 0.1 | 0.2 | 0.1 | | | | | | | |
| N | 10 | 9 | 10 | 10 | 9 | 10 | | | | | | | |
| Combined | | | | | | | | | | | | | |
| Mean | 0.6 | 0.7- | 0.8-- | 0.9@- | 0.8-- | 0.8@- | I | -- | -- | -- | -- | -- | -- |
| Std. Err. | 0.0 | 0.1 | 0.1 | 0.0 | 0.1 | 0.1 | | | | | | | |
| N | 20 | 19 | 20 | 20 | 19 | 20 | | | | | | | |
| | | | | Burr Cells (coded) | | | | | | | | | |
| Male | | | | | | | | | | | | | |
| Mean | 0.1 | 0.2 | 0.1 | 0.0 | 0.0 | 0.0 | | | | | | | |
| Std. Err. | 0.1 | 0.1 | 0.1 | 0.0 | 0.0 | 0.0 | | | | | | | |
| N | 10 | 10 | 10 | 10 | 10 | 10 | | | | | | | |
| Female | | | | | | | | | | | | | |
| Mean | 0.1 | 0.0 | 0.1 | 0.1 | 0.1 | 0.2 | | | | | | | |
| Std. Err. | 0.1 | 0.0 | 0.1 | 0.1 | 0.1 | 0.1 | | | | | | | |
| N | 10 | 9 | 10 | 10 | 9 | 10 | | | | | | | |

TABLE 4-continued

Blood Assays
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| Combined | | | | | | | | | | | | | |
| Mean | 0.1 | 0.1- | 0.1-- | 0.0-- | 0.1-- | 0.1-- | - | - | - | - | - | - | - |
| Std. Err. | 0.1 | 0.0 | 0.0 | 0.0 | 0.0 | 0.0 | | | | | | | |
| N | 20 | 19 | 20 | 20 | 19 | 20 | | | | | | | |
| | | | | Howell Jolly Bodies (coded) | | | | | | | | | |
| Male | | | | | | | | | | | | | |
| Mean | 0.1 | 0.1 | 0.1 | 0.5 | 0.1 | 0.3 | | | | | | | |
| Std. Err. | 0.1 | 0.1 | 0.1 | 0.1 | 0.1 | 0.1 | | | | | | | |
| N | 10 | 10 | 10 | 10 | 10 | 10 | | | | | | | |
| Female | | | | | | | | | | | | | |
| Mean | 0.0 | 0.0 | 0.0 | 0.3 | 0.1 | 0.2 | | | | | | | |
| Std. Err. | 0.0 | 0.0 | 0.0 | 0.1 | 0.1 | 0.1 | | | | | | | |
| N | 10 | 9 | 10 | 10 | 9 | 10 | | | | | | | |
| Combined | | | | | | | | | | | | | |
| Mean | 0.1 | 0.0- | 0.0-- | 0.4@# | 0.1-- | 0.22@# | - | I | - | - | - | - | - |
| Std. Err. | 0.0 | 0.0 | 0.0 | 0.1 | 0.0 | 0.1 | | | | | | | |
| N | 20 | 19 | 20 | 20 | 19 | 20 | | | | | | | |
| | | | | Reticulocytes (%) | | | | | | | | | |
| Male | | | | | | | | | | | | | |
| Mean | 1.4 | 1.5 | 1.5 | 1.7 | 1.4 | 1.6 | | | | | | | |
| Std. Err. | 0.1 | 0.2 | 0.1 | 0.1 | 0.2 | 0.1 | | | | | | | |
| N | 10 | 10 | 10 | 10 | 10 | 10 | | | | | | | |
| Female | | | | | | | | | | | | | |
| Mean | 1.3 | 1.4 | 1.4 | 1.3 | 1.5 | 1.3 | | | | | | | |
| Std. Err. | 0.1 | 0.1 | 0.2 | 0.2 | 0.2 | 0.2 | | | | | | | |
| N | 10 | 9 | 10 | 10 | 9 | 9 | | | | | | | |
| Combined | | | | | | | | | | | | | |
| Mean | 1.4 | 1.5- | 1.4-- | 1.5-- | 1.4-- | 1.4-- | - | - | - | - | - | - | - |
| Std. Err. | 0.1 | 0.1 | 0.1 | 0.1 | 0.1 | 0.1 | | | | | | | |
| N | 20 | 19 | 20 | 20 | 19 | 19 | | | | | | | |

@Indicates Difference From Group 1: 0 mg/kg AZT, 0.0% Procysteine
Indicates Difference From Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 indicate Sexes Did Not Differ Therefore Tests Are Performed Across Sex

TABLE 5

Bone Marrow-Myeloid Series %
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| | | | | Myeloblast (%) | | | | | | | | | |
| Male | | | | | | | | | | | | | |
| Mean | 3.0 | 3.3- | 3.8@# | 3.5@- | 3.5@- | 3.6@- | | | | - | - | - | - |
| Std. Err. | 0.2 | 0.2 | 0.1 | 0.1 | 0.2 | 0.1 | | | | | | | |
| N | 10 | 10 | 10 | 10 | 10 | 10 | | | | | | | |
| Female | | | | | | | | | | | | | |
| Mean | 2.4 | 3.2@ | 3.5@- | 3.6@- | 2.7-- | 3.1@- | | | | I | D | D | * |
| Std. Err. | 0.1 | 0.1 | 0.1 | 0.1 | 0.2 | 0.1 | | | | | | | |
| N | 10 | 8 | 10 | 10 | 8 | 9 | | | | | | | |
| Combined | | | | | | | | | | | | | |
| Mean | 2.7 | 3.2 | 3.6 | 3.6 | 3.1 | 3.3 | I | - | * | | | | |
| Std. Err. | 0.1 | 0.1 | 0.1 | 0.1 | 0.2 | 0.1 | | | | | | | |
| N | 20 | 18 | 20 | 20 | 18 | 19 | | | | | | | |
| | | | | Promyelocyte (%) | | | | | | | | | |
| Male | | | | | | | | | | | | | |
| Mean | 9.3 | 8.5 | 13.0 | 12.7 | 9.6 | 9.9 | | | | | | | |
| Std. Err. | 0.2 | 0.2 | 0.2 | 0.3 | 0.1 | 0.1 | | | | | | | |
| N | 10 | 10 | 10 | 10 | 10 | 10 | | | | | | | |
| Female | | | | | | | | | | | | | |
| Mean | 9.0 | 8.4 | 12.1 | 12.5 | 8.9 | 9.1 | | | | | | | |

TABLE 5-continued

Bone Marrow-Myeloid Series %
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| Std. Err. | 0.2 | 0.3 | 0.1 | 0.1 | 0.3 | 0.2 | | | | | | | |
| N | 10 | 8 | 10 | 10 | 8 | 9 | | | | | | | |
| Combined | | | | | | | | | | | | | |
| Mean | 9.1 | 8.4@ | 12.6@# | 12.6@# | 9.3-# | 9.5-# | I | I | * | D | D | D | * |
| Std. Err. | 0.2 | 0.2 | 0.2 | 0.2 | 0.2 | 0.1 | | | | | | | |
| N | 20 | 18 | 20 | 20 | 18 | 19 | | | | | | | |
| | | | | Myelocyte (%) | | | | | | | | | |
| Male | | | | | | | | | | | | | |
| Mean | 9.1 | 9.6 | 12.9 | 12.4 | 9.6 | 10.0 | | | | | | | |
| Std. Err. | 0.3 | 0.3 | 0.2 | 0.3 | 0.2 | 0.3 | | | | | | | |
| N | 10 | 10 | 10 | 10 | 10 | 10 | | | | | | | |
| Female | | | | | | | | | | | | | |
| Mean | 8.8 | 9.4 | 12.5 | 12.7 | 9.6 | 9.8 | | | | | | | |
| Std. Err. | 0.2 | 0.2 | 0.3 | 0.2 | 0.2 | 0.3 | | | | | | | |
| N | 10 | 8 | 10 | 10 | 8 | 9 | | | | | | | |
| Combined | | | | | | | | | | | | | |
| Mean | 9.0 | 9.5- | 12.7@# | 12.6@# | 9.6-- | 9.9@- | I | - | * | - | D | D | * |
| Std. Err. | 0.2 | 0.2 | 0.2 | 0.2 | 0.1 | 0.2 | | | | | | | |
| N | 20 | 18 | 20 | 20 | 18 | 19 | | | | | | | |
| | | | | Total Proliferating (%) | | | | | | | | | |
| Male | | | | | | | | | | | | | |
| Mean | 21.3 | 21.4- | 29.8@# | 28.7@# | 22.79@# | 23.5@# | | | | | | | |
| Std. Err. | 0.3 | 0.2 | 0.3 | 0.4 | 0.3 | 0.3 | | | | | | | |
| N | 10 | 10 | 10 | 10 | 10 | 10 | | | | | | | |
| Female | | | | | | | | | | | | | |
| Mean | 20.2 | 20.9- | 28.0@# | 28.9@# | 21.1-- | 22.0@# | | | | | | | |
| Std. Err. | 0.3 | 0.4 | 0.2 | 0.2 | 0.4 | 0.3 | | | | | | | |
| N | 10 | 8 | 10 | 10 | 8 | 9 | | | | | | | |
| Combined | | | | | | | | | | | | | |
| Mean | 20.7 | 21.2 | 28.9 | 28.8 | 22.0 | 22.8 | I | I | * | - | D | D | * |
| Std. Err. | 0.2 | 0.2 | 0.3 | 0.2 | 0.3 | 0.3 | | | | | | | |
| N | 20 | 18 | 20 | 20 | 18 | 19 | | | | | | | |
| | | | | Metamyelocyte (%) | | | | | | | | | |
| Male | | | | | | | | | | | | | |
| Mean | 8.8 | 8.0- | 8.7-- | 8.6-- | 9.8@# | 9.0-# | | | | | | | |
| Std. Err. | 0.3 | 0.3 | 0.2 | 0.2 | 0.3 | 0.2 | | | | | | | |
| N | 10 | 10 | 10 | 10 | 10 | 10 | | | | | | | |
| Female | | | | | | | | | | | | | |
| Mean | 8.4 | 8.5- | 8.9-- | 9.2-- | 8.8-- | 9.9@# | | | | | | | |
| Std. Err. | 0.1 | 0.4 | 0.2 | 0.2 | 0.4 | 0.2 | | | | | | | |
| N | 10 | 8 | 10 | 10 | 8 | 9 | | | | | | | |
| Combined | | | | | | | | | | | | | |
| Mean | 8.6 | 8.2 | 8.8 | 8.9 | 9.3 | 9.4 | - | I | * | - | - | - | * |
| Std. Err. | 0.1 | 0.2 | 0.1 | 0.2 | 0.2 | 0.2 | | | | | | | |
| N | 20 | 18 | 20 | 20 | 18 | 19 | | | | | | | |
| | | | | Band (%) | | | | | | | | | |
| Male | | | | | | | | | | | | | |
| Mean | 15.2 | 15.8- | 13.6@# | 14.0@# | 15.2-- | 15.5-- | | | | | | | |
| Std. Err. | 0.3 | 0.2 | 0.2 | 0.2 | 0.1 | 0.2 | | | | | | | |
| N | 10 | 10 | 10 | 10 | 10 | 10 | | | | | | | |
| Female | | | | | | | | | | | | | |
| Mean | 15.6 | 15.5- | 14.9-- | 13.7@# | 15.3-- | 15.7-- | | | | | | | |
| Std. Err. | 0.1 | 0.3 | 0.2 | 0.3 | 0.3 | 0.3 | | | | | | | |
| N | 10 | 8 | 10 | 10 | 8 | 9 | | | | | | | |
| Combined | | | | | | | | | | | | | |
| Mean | 15.4 | 15.6 | 14.2 | 13.8 | 15.3 | 15.6 | D | - | * | - | I | I | * |
| Std. Err. | 0.2 | 0.2 | 0.2 | 0.2 | 0.1 | 0.1 | | | | | | | |
| N | 20 | 18 | 20 | 20 | 18 | 19 | | | | | | | |
| | | | | Neutrophil (%) | | | | | | | | | |
| Male | | | | | | | | | | | | | |
| Mean | 13.4 | 13.4- | 12.3@# | 12.9-- | 12.9-- | 13.5-- | | | | | | | |
| Std. Err. | 0.3 | 0.3 | 0.2 | 0.1 | 0.2 | 0.2 | | | | | | | |
| N | 10 | 10 | 10 | 10 | 10 | 10 | | | | | | | |
| Female | | | | | | | | | | | | | |
| Mean | 13.2 | 13.7- | 12.5-# | 12.4@# | 13.6-- | 12.4-# | | | | | | | |
| Std. Err. | 0.1 | 0.3 | 0.2 | 0.3 | 0.3 | 0.2 | | | | | | | |
| N | 10 | 8 | 10 | 10 | 8 | 9 | | | | | | | |
| Combined | | | | | | | | | | | | | |
| Mean | 13.3 | 13.5 | 12.4 | 12.6 | 13.2 | 13.0 | D | - | - | - | I | - | - |

TABLE 5-continued

Bone Marrow-Myeloid Series %
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| Std. Err. | 0.2 | 0.2 | 0.1 | 0.2 | 0.2 | 0.2 | | | | | | | |
| N | 20 | 18 | 20 | 20 | 18 | 19 | | | | | | | |
| *Eosinophil (%)* | | | | | | | | | | | | | |
| Male | | | | | | | | | | | | | |
| Mean | 3.7 | 4.4- | 2.8@# | 2.9@# | 2.9@# | 3.5-# | | | | | | | |
| Std. Err. | 0.2 | 0.2 | 0.1 | 0.2 | 0.2 | 0.2 | | | | | | | |
| N | 10 | 10 | 10 | 10 | 10 | 10 | | | | | | | |
| Female | | | | | | | | | | | | | |
| Mean | 3.4 | 4.3@ | 3.0-# | 2.2@# | 4.2@- | 3.2-# | | | | | | | |
| Std. Err. | 0.2 | 0.1 | 0.2 | 0.1 | 0.2 | 0.3 | | | | | | | |
| N | 10 | 8 | 10 | 10 | 8 | 9 | | | | | | | |
| Combined | | | | | | | | | | | | | |
| Mean | 3.5 | 4.4 | 2.9 | 2.6 | 3.5 | 3.3 | D | D | - | I | I | I | - |
| Std. Err. | 0.2 | 0.1 | 0.1 | 0.1 | 0.2 | 0.2 | | | | | | | |
| N | 20 | 18 | 20 | 20 | 18 | 19 | | | | | | | |
| *Basophil (%)* | | | | | | | | | | | | | |
| Male | | | | | | | | | | | | | |
| Mean | 0.0 | 0.0 | 0.0 | 0.0 | 0.0 | 0.0 | | | | | | | |
| Std. Err. | 0.0 | 0.0 | 0.0 | 0.0 | 0.0 | 0.0 | | | | | | | |
| N | 10 | 10 | 10 | 10 | 10 | 10 | | | | | | | |
| Female | | | | | | | | | | | | | |
| Mean | 0.0 | 0.0 | 0.0 | 0.0 | 0.0 | 0.0 | | | | | | | |
| Std. Err. | 0.0 | 0.0 | 0.0 | 0.0 | 0.0 | 0.0 | | | | | | | |
| N | 10 | 8 | 10 | 10 | 8 | 9 | | | | | | | |
| Combined | | | | | | | | | | | | | |
| Mean | 0.0 | 0.0- | 0.0-- | 0.0-- | 0.0-- | 0.0-- | - | - | - | - | - | - | - |
| Std. Err. | 0.0 | 0.0 | 0.0 | 0.0 | 0.0 | 0.0 | | | | | | | |
| N | 20 | 18 | 20 | 20 | 18 | 19 | | | | | | | |
| *Total Myeloid (%)* | | | | | | | | | | | | | |
| Male | | | | | | | | | | | | | |
| Mean | 62.4 | 62.9- | 67.2@# | 67.0@# | 63.6@- | 64.9@# | | | | | | | |
| Std. Err. | 0.3 | 0.2 | 0.2 | 0.3 | 0.3 | 0.2 | | | | | | | |
| N | 10 | 10 | 10 | 10 | 10 | 10 | | | | | | | |
| Female | | | | | | | | | | | | | |
| Mean | 60.8 | 62.8@ | 67.4@# | 66.3@# | 63.1@- | 63.3@- | | | | | | | |
| Std. Err. | 0.4 | 0.3 | 0.3 | 0.2 | 0.3 | 0.3 | | | | | | | |
| N | 10 | 8 | 10 | 10 | 8 | 9 | | | | | | | |
| Combined | | | | | | | | | | | | | |
| Mean | 61.6 | 62.9 | 67.3 | 66.7 | 63.3 | 64.1 | I | I | * | I | D | D | * |
| Std. Err. | 0.3 | 0.2 | 0.2 | 0.2 | 0.2 | 0.2 | | | | | | | |
| N | 20 | 18 | 20 | 20 | 18 | 19 | | | | | | | |

@Indicates Difference From Group 1: 0 mg/kg AZT, 0.0% Procysteine
Indicates Difference From Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 Indicate Sexes Did Not Differ Therefore Tests Are Performed Across Sex

TABLE 5A

Bone Marrow-Myeloid Series/Femur $\times 10^{**}6$
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.09% | 1.0% | 0.0 | 1.0 | DIF | 0 | 50 | 500 | DIF |
| *Myeloblast (/Femur $\times 10^{**}6$)* | | | | | | | | | | | | | |
| Male | | | | | | | | | | | | | |
| Mean | 0.35 | 0.42 | 0.44 | 0.37 | 0.45 | 0.36 | | | | | | | |
| Std. Err. | 0.02 | 0.02 | 0.02 | 0.02 | 0.03 | 0.01 | | | | | | | |
| N | 10 | 10 | 10 | 10 | 10 | 10 | | | | | | | |
| Female | | | | | | | | | | | | | |
| Mean | 0.27 | 0.38 | 0.35 | 0.32 | 0.27 | 0.28 | | | | | | | |
| Std. Err. | 0.02 | 0.02 | 0.03 | 0.01 | 0.01 | 0.02 | | | | | | | |
| N | 10 | 8 | 10 | 10 | 8 | 9 | | | | | | | |

TABLE 5A-continued

Bone Marrow-Myeloid Series/Femur × 10**6
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.09% | 1.0% | 0.0 | 1.0 | DIF | 0 | 50 | 500 | DIF |
| Combined | | | | | | | | | | | | | |
| Mean | 0.31 | 0.40@ | 0.40@- | 0.34-- | 0.37-- | 0.32-# | - | D | * | I | - | - | * |
| Std. Err. | 0.02 | 0.02 | 0.02 | 0.01 | 0.03 | 0.02 | | | | | | | |
| N | 20 | 18 | 20 | 20 | 18 | 19 | | | | | | | |
| Promyelocyte (/Femur × 10**6) | | | | | | | | | | | | | |
| Male | | | | | | | | | | | | | |
| Mean | 1.10 | 1.08 | 1.53 | 1.34 | 1.21 | 0.99 | | | | | | | |
| Std. Err. | 0.06 | 0.03 | 0.06 | 0.06 | 0.05 | 0.04 | | | | | | | |
| N | 10 | 10 | 10 | 10 | 10 | 10 | | | | | | | |
| Female | | | | | | | | | | | | | |
| Mean | 1.02 | 0.99 | 1.20 | 1.10 | 0.93 | 0.82 | | | | | | | |
| Std. Err. | 0.04 | 0.06 | 0.06 | 0.05 | 0.08 | 0.05 | | | | | | | |
| N | 10 | 8 | 10 | 10 | 8 | 9 | | | | | | | |
| Combined | | | | | | | | | | | | | |
| Mean | 1.06 | 1.04- | 1.36@# | 1.22@# | 1.08-- | 0.91@- | I | - | * | - | D | D | * |
| Std. Err. | 0.04 | 0.03 | 0.06 | 0.05 | 0.06 | 0.04 | | | | | | | |
| N | 20 | 18 | 20 | 20 | 18 | 19 | | | | | | | |
| Myelocyte (/Femur × 10**6) | | | | | | | | | | | | | |
| Male | | | | | | | | | | | | | |
| Mean | 1.08 | 1.23 | 1.51 | 1.31 | 1.21 | 1.00 | | | | | | | |
| Std. Err. | 0.08 | 0.06 | 0.06 | 0.07 | 0.06 | 0.05 | | | | | | | |
| N | 10 | 10 | 10 | 10 | 10 | 10 | | | | | | | |
| Female | | | | | | | | | | | | | |
| Mean | 1.01 | 1.11 | 1.24 | 1.12 | 0.99 | 0.88 | | | | | | | |
| Std. Err. | 0.05 | 0.07 | 0.07 | 0.05 | 0.07 | 0.05 | | | | | | | |
| N | 10 | 8 | 10 | 10 | 8 | 9 | | | | | | | |
| Combined | | | | | | | | | | | | | |
| Mean | 1.04 | 1.18- | 1.37@# | 1.21@- | 1.11-- | 0.95-# | I | D | * | - | D | D | * |
| Std. Err. | 0.05 | 0.05 | 0.05 | 0.05 | 0.05 | 0.04 | | | | | | | |
| N | 20 | 18 | 20 | 20 | 18 | 19 | | | | | | | |
| Total Proliferating (/Femur × 10**6) | | | | | | | | | | | | | |
| Male | | | | | | | | | | | | | |
| Mean | 2.53 | 2.73 | 3.48 | 3.02 | 2.87 | 2.35 | | | | | | | |
| Std. Err. | 0.14 | 0.10 | 0.13 | 0.14 | 0.14 | 0.09 | | | | | | | |
| N | 10 | 10 | 10 | 10 | 10 | 10 | | | | | | | |
| Female | | | | | | | | | | | | | |
| Mean | 2.30 | 2.48 | 2.78 | 2.53 | 2.18 | 1.98 | | | | | | | |
| Std. Err. | 0.10 | 0.13 | 0.14 | 0.11 | 0.15 | 0.10 | | | | | | | |
| N | 10 | 8 | 10 | 10 | 8 | 9 | | | | | | | |
| Combined | | | | | | | | | | | | | |
| Mean | 2.41 | 2.62- | 3.13@# | 2.78@- | 2.56-- | 2.18-# | I | D | * | - | D | D | * |
| Std. Err. | 0.09 | 0.08 | 0.12 | 0.10 | 0.13 | 0.08 | | | | | | | |
| N | 20 | 18 | 20 | 20 | 18 | 19 | | | | | | | |
| Metamyelocyte (/Femur × 10**6) | | | | | | | | | | | | | |
| Male | | | | | | | | | | | | | |
| Mean | 1.04 | 1.01 | 1.02 | 0.90 | 1.23 | 0.90 | | | | | | | |
| Std. Err. | 0.07 | 0.04 | 0.05 | 0.04 | 0.06 | 0.04 | | | | | | | |
| N | 10 | 10 | 10 | 10 | 10 | 10 | | | | | | | |
| Female | | | | | | | | | | | | | |
| Mean | 0.96 | 1.01 | 0.88 | 0.80 | 0.92 | 0.89 | | | | | | | |
| Std. Err. | 0.04 | 0.08 | 0.03 | 0.03 | 0.08 | 0.05 | | | | | | | |
| N | 10 | 8 | 10 | 10 | 8 | 9 | | | | | | | |
| Combined | | | | | | | | | | | | | |
| Mean | 1.00 | 1.01- | 0.95-- | 0.85@# | 1.09-- | 0.90-- | D | - | - | - | - | - | - |
| Std. Err. | 0.04 | 0.04 | 0.03 | 0.03 | 0.06 | 0.03 | | | | | | | |
| N | 20 | 18 | 20 | 20 | 18 | 19 | | | | | | | |
| Band (/Femur × 10**6) | | | | | | | | | | | | | |
| Male | | | | | | | | | | | | | |
| Mean | 1.80 | 2.01 | 1.59 | 1.47 | 1.92 | 1.55 | | | | | | | |
| Std. Err. | 0.10 | 0.06 | 0.06 | 0.06 | 0.08 | 0.05 | | | | | | | |
| N | 10 | 10 | 10 | 10 | 10 | 10 | | | | | | | |
| Female | | | | | | | | | | | | | |
| Mean | 1.78 | 1.84 | 1.48 | 1.20 | 1.58 | 1.41 | | | | | | | |
| Std. Err. | 0.08 | 0.09 | 0.08 | 0.05 | 0.10 | 0.07 | | | | | | | |
| N | 10 | 8 | 10 | 10 | 8 | 9 | | | | | | | |
| Combined | | | | | | | | | | | | | |
| Mean | 1.79 | 1.93- | 1.53@# | 1.33@# | 1.77-- | 1.48@# | D | D | - | - | I | - | - |
| Std. Err. | 0.06 | 0.06 | 0.05 | 0.05 | 0.07 | 0.04 | | | | | | | |
| N | 20 | 18 | 20 | 20 | 18 | 19 | | | | | | | |

TABLE 5A-continued

Bone Marrow-Myeloid Series/Femur × 10**6
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.09% | 1.0% | 0.0 | 1.0 | DIF | 0 | 50 | 500 | DIF |
| *Neutrophil (/Femur × 10**6)* | | | | | | | | | | | | | |
| Male | | | | | | | | | | | | | |
| Mean | 1.59 | 1.70 | 1.43 | 1.36 | 1.63 | 1.35 | | | | | | | |
| Std. Err. | 0.10 | 0.06 | 0.05 | 0.06 | 0.08 | 0.05 | | | | | | | |
| N | 10 | 10 | 10 | 10 | 10 | 10 | | | | | | | |
| Female | | | | | | | | | | | | | |
| Mean | 1.51 | 1.63 | 1.24 | 1.09 | 1.40 | 1.12 | | | | | | | |
| Std. Err. | 0.07 | 0.10 | 0.05 | 0.05 | 0.09 | 0.06 | | | | | | | |
| N | 10 | 8 | 10 | 10 | 8 | 9 | | | | | | | |
| Combined | | | | | | | | | | | | | |
| Mean | 1.55 | 1.67- | 1.34@# | 1.22@# | 1.53-- | 1.24@# | D | D | - | - | I | - | - |
| Std. Err. | 0.06 | 0.06 | 0.04 | 0.05 | 0.06 | 0.05 | | | | | | | |
| N | 20 | 18 | 20 | 20 | 18 | 19 | | | | | | | |
| *Eosinophil (/Femur × 10**6)* | | | | | | | | | | | | | |
| Male | | | | | | | | | | | | | |
| Mean | 0.43 | 0.57 | 0.33 | 0.31 | 0.37 | 0.35 | | | | | | | |
| Std. Err. | 0.03 | 0.04 | 0.02 | 0.03 | 0.02 | 0.02 | | | | | | | |
| N | 10 | 10 | 10 | 10 | 10 | 10 | | | | | | | |
| Female | | | | | | | | | | | | | |
| Mean | 0.39 | 0.51 | 0.29 | 0.19 | 0.44 | 0.28 | | | | | | | |
| Std. Err. | 0.03 | 0.04 | 0.02 | 0.01 | 0.04 | 0.02 | | | | | | | |
| N | 10 | 8 | 10 | 10 | 8 | 9 | | | | | | | |
| Combined | | | | | | | | | | | | | |
| Mean | 0.41 | 0.55@ | 0.31@# | 0.25@# | 0.40-# | 0.32@# | D | D | - | I | I | - | - |
| Std. Err. | 0.02 | 0.03 | 0.01 | 0.02 | 0.02 | 0.02 | | | | | | | |
| N | 20 | 18 | 20 | 20 | 18 | 19 | | | | | | | |
| *Basophil (/Femur × 10**6)* | | | | | | | | | | | | | |
| Male | | | | | | | | | | | | | |
| Mean | 0.000 | 0.002 | 0.002 | 0.000 | 0.005 | 0.000 | | | | | | | |
| Std. Err. | 0.000 | 0.002 | 0.002 | 0.000 | 0.004 | 0.000 | | | | | | | |
| N | 10 | 10 | 10 | 10 | 10 | 10 | | | | | | | |
| Female | | | | | | | | | | | | | |
| Mean | 0.004 | 0.000 | 0.002 | 0.003 | 0.003 | 0.002 | | | | | | | |
| Std. Err. | 0.003 | 0.000 | 0.002 | 0.002 | 0.003 | 0.002 | | | | | | | |
| N | 10 | 8 | 10 | 10 | 8 | 9 | | | | | | | |
| Combined | | | | | | | | | | | | | |
| Mean | 0.002 | 0.001- | 0.002-- | 0.002-- | 0.004-- | 0.001-- | - | - | - | - | - | - | - |
| Std. Err. | 0.002 | 0.001 | 0.001 | 0.001 | 0.002 | 0.001 | | | | | | | |
| N | 20 | 18 | 20 | 20 | 18 | 19 | | | | | | | |
| *Total Myeloid (/Femur × 10**6)* | | | | | | | | | | | | | |
| Male | | | | | | | | | | | | | |
| Mean | 7.39 | 8.03 | 7.85 | 7.05 | 8.02 | 6.50 | | | | | | | |
| Std. Err. | 0.40 | 0.27 | 0.29 | 0.30 | 0.35 | 0.23 | | | | | | | |
| N | 10 | 10 | 10 | 10 | 10 | 10 | | | | | | | |
| Female | | | | | | | | | | | | | |
| Mean | 6.93 | 7.47 | 6.68 | 5.82 | 6.53 | 5.69 | | | | | | | |
| Std. Err. | 0.31 | 0.41 | 0.30 | 0.23 | 0.42 | 0.27 | | | | | | | |
| N | 10 | 8 | 10 | 10 | 8 | 9 | | | | | | | |
| Combined | | | | | | | | | | | | | |
| Mean | 7.16 | 7.78- | 7.27-- | 6.43-# | 7.35-- | 6.12@# | - | D | - | - | - | - | - |
| Std. Err. | 0.25 | 0.24 | 0.24 | 0.23 | 0.32 | 0.20 | | | | | | | |
| N | 20 | 18 | 20 | 20 | 18 | 19 | | | | | | | |

@Indicates Difference From Group 1: 0 mg/kg AZT, 0.0% Procysteine
Indicates Difference From Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 Indicate Sexes Did Not Differ Therefore Tests Are Performed Across Sex

TABLE 6

Bone Marrow-Erythroid Series %
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| *Rubriblast (%)* | | | | | | | | | | | | | |
| Male | | | | | | | | | | | | | |
| Mean | 1.1 | 1.1 | 0.7 | 0.7 | 1.1 | 1.0 | | | | | | | |
| Std. Err. | 0.1 | 0.1 | 0.1 | 0.1 | 0.1 | 0.1 | | | | | | | |
| N | 10 | 10 | 10 | 10 | 10 | 10 | | | | | | | |
| Female | | | | | | | | | | | | | |
| Mean | 1.1 | 1.0 | 0.5 | 0.6 | 1.1 | 1.1 | | | | | | | |
| Std. Err. | 0.1 | 0.1 | 0.0 | 0.0 | 0.1 | 0.1 | | | | | | | |
| N | 10 | 8 | 10 | 10 | 8 | 9 | | | | | | | |
| Combined | | | | | | | | | | | | | |
| Mean | 1.1 | 1.0- | 0.6@# | 0.7@# | 1.1-- | 1.0-- | D | - | * | - | I | I | * |
| Std. Err. | 0.0 | 0.0 | 0.0 | 0.0 | 0.0 | 0.0 | | | | | | | |
| N | 20 | 18 | 20 | 20 | 18 | 19 | | | | | | | |
| *Prorubricyte (%)* | | | | | | | | | | | | | |
| Male | | | | | | | | | | | | | |
| Mean | 8.7 | 8.0- | 9.9@# | 9.4-# | 9.3-# | 9.0-# | | | | | | | |
| Std. Err. | 0.3 | 0.2 | 0.2 | 0.2 | 0.2 | 0.2 | | | | | | | |
| N | 10 | 10 | 10 | 10 | 10 | 10 | | | | | | | |
| Female | | | | | | | | | | | | | |
| Mean | 8.7 | 8.1- | 8.8-- | 10.7@# | 8.1-- | 8.8-- | | | | | | | |
| Std. Err. | 0.3 | 0.3 | 0.2 | 0.3 | 0.2 | 0.4 | | | | | | | |
| N | 10 | 8 | 10 | 10 | 8 | 9 | | | | | | | |
| Combined | | | | | | | | | | | | | |
| Mean | 8.7 | 8.0 | 9.3 | 10.0 | 8.7 | 8.9 | I | I | - | D | - | D | - |
| Std. Err. | 0.2 | 0.2 | 0.2 | 0.2 | 0.2 | 0.2 | | | | | | | |
| N | 20 | 18 | 20 | 20 | 18 | 19 | | | | | | | |
| *Rubricyte* | | | | | | | | | | | | | |
| Male | | | | | | | | | | | | | |
| Mean | 22.0 | 22.7- | 19.9@# | 20.2@# | 23.6@- | 22.8-- | D | - | * | - | I | I | * |
| Std. Err. | 0.3 | 0.2 | 0.1 | 0.3 | 0.2 | 0.2 | | | | | | | |
| N | 10 | 10 | 10 | 10 | 10 | 10 | | | | | | | |
| Female | | | | | | | | | | | | | |
| Mean | 23.4 | 22.2@ | 19.9@# | 20.0@# | 22.2@- | 21.6@- | D | - | * | D | I | I | * |
| Std. Err. | 0.2 | 0.4 | 0.2 | 0.1 | 0.3 | 0.3 | | | | | | | |
| N | 10 | 8 | 10 | 10 | 8 | 9 | | | | | | | |
| Combined | | | | | | | | | | | | | |
| Mean | 22.7 | 22.5 | 19.9 | 20.1 | 23.0 | 22.3 | | | | | | | |
| Std. Err. | 0.3 | 0.2 | 0.1 | 0.2 | 0.2 | 0.2 | | | | | | | |
| N | 20 | 18 | 20 | 20 | 18 | 19 | | | | | | | |
| *Total Proliferating (%)* | | | | | | | | | | | | | |
| Male | | | | | | | | | | | | | |
| Mean | 31.8 | 31.7- | 30.5@# | 30.3@# | 34.0@# | 32.8-# | | | | - | I | I | * |
| Std. Err. | 0.3 | 0.4 | 0.1 | 0.3 | 0.4 | 0.2 | | | | | | | |
| N | 10 | 10 | 10 | 10 | 10 | 10 | | | | | | | |
| Female | | | | | | | | | | | | | |
| Mean | 33.3 | 31.3@ | 29.2@# | 31.3@- | 31.3@- | 31.5@ | | | | D | I | - | * |
| Std. Err. | 0.5 | 0.3 | 0.2 | 0.2 | 0.2 | 0.2 | | | | | | | |
| N | 10 | 8 | 10 | 10 | 8 | 9 | | | | | | | |
| Combined | | | | | | | | | | | | | |
| Mean | 32.6 | 31.5 | 29.9 | 30.8 | 32.8 | 32.2 | D | - | * | | | | |
| Std. Err. | 0.3 | 0.2 | 0.2 | 0.2 | 0.4 | 0.2 | | | | | | | |
| N | 20 | 18 | 20 | 20 | 18 | 19 | | | | | | | |
| *Metarubricyte (%)* | | | | | | | | | | | | | |
| Male | | | | | | | | | | | | | |
| Mean | 4.5 | 4.0- | 1.0@# | 1.5@# | 1.0@# | 1.0@# | D | D | - | - | - | - | - |
| Std. Err. | 0.2 | 0.2 | 0.1 | 0.1 | 0.1 | 0.1 | | | | | | | |
| N | 10 | 10 | 10 | 10 | 10 | 10 | | | | | | | |
| Female | | | | | | | | | | | | | |
| Mean | 4.3 | 4.2- | 2.2@# | 1.2@# | 4.0-- | 3.8-- | D | - | * | - | I | I | * |
| Std. Err. | 0.3 | 0.2 | 0.2 | 0.1 | 0.2 | 0.2 | | | | | | | |
| N | 10 | 8 | 10 | 10 | 8 | 9 | | | | | | | |
| Combined | | | | | | | | | | | | | |
| Mean | 4.4 | 4.1 | 1.6 | 1.3 | 2.3 | 2.4 | | | | | | | |
| Std. Err. | 0.2 | 0.1 | 0.2 | 0.1 | 0.4 | 0.3 | | | | | | | |
| N | 20 | 18 | 20 | 20 | 18 | 19 | | | | | | | |
| *Total Erythroid (%)* | | | | | | | | | | | | | |
| Male | | | | | | | | | | | | | |
| Mean | 36.3 | 35.7- | 31.5@# | 31.8@# | 35.0@- | 33.9@# | | | | | | | |
| Std. Err. | 0.3 | 0.3 | 0.1 | 0.3 | 0.3 | 0.2 | | | | | | | |

TABLE 6-continued

Bone Marrow-Erythroid Series %
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| N | 10 | 10 | 10 | 10 | 10 | 10 | | | | | | | |
| Female | | | | | | | | | | | | | |
| Mean | 37.6 | 35.4@ | 31.4@# | 32.4@# | 35.2@- | 35.4@- | | | | | | | |
| Std. Err. | 0.3 | 0.1 | 0.3 | 0.2 | 0.2 | 0.2 | | | | | | | |
| N | 10 | 8 | 10 | 10 | 8 | 9 | | | | | | | |
| Combined | | | | | | | | | | | | | |
| Mean | 37.0 | 35.6 | 31.5 | 32.1 | 35.1 | 34.6 | D | - | * | D | I | I | * |
| Std. Err. | 0.3 | 0.2 | 0.2 | 0.2 | 0.2 | 0.2 | | | | | | | |
| N | 20 | 18 | 20 | 20 | 18 | 19 | | | | | | | |

@Indicates Difference From Group 1: 0 mg/kg AZT, 0.0% Procysteine
Indicates Difference From Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 Indicate Sexes Did Not Differ Therefore Tests Are Performed Across Sex

TABLE 6a

Bone Marrow-Erythroid Series/Femur × 10**6
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| Rubriblast (/Femur × 10**6) | | | | | | | | | | | | | |
| Male | | | | | | | | | | | | | |
| Mean | 0.13 | 0.14 | 0.08 | 0.08 | 0.14 | 0.10 | | | | | | | |
| Std. Err. | 0.01 | 0.01 | 0.01 | 0.01 | 0.01 | 0.01 | | | | | | | |
| N | 10 | 10 | 10 | 10 | 10 | 10 | | | | | | | |
| Female | | | | | | | | | | | | | |
| Mean | 0.13 | 0.12 | 0.05 | 0.05 | 0.11 | 0.10 | | | | | | | |
| Std. Err. | 0.01 | 0.01 | 0.00 | 0.00 | 0.01 | 0.01 | | | | | | | |
| N | 10 | 8 | 10 | 10 | 8 | 9 | | | | | | | |
| Combined | | | | | | | | | | | | | |
| Mean | 0.13 | 0.13- | 0.07@# | 0.06@# | 0.12-- | 0.10@# | D | D | * | - | I | I | * |
| Std. Err. | 0.01 | 0.01 | 0.01 | 0.01 | 0.01 | 0.00 | | | | | | | |
| N | 20 | 18 | 20 | 20 | 18 | 19 | | | | | | | |
| Prorubricyte (/Femur × 10**6) | | | | | | | | | | | | | |
| Male | | | | | | | | | | | | | |
| Mean | 1.03 | 1.01- | 1.16-- | 0.99-- | 1.17-- | 0.91-- | | | | | | | |
| Std. Err. | 0.06 | 0.03 | 0.04 | 0.05 | 0.07 | 0.04 | | | | | | | |
| N | 10 | 10 | 10 | 10 | 10 | 10 | | | | | | | |
| Female | | | | | | | | | | | | | |
| Mean | 0.99 | 0.96- | 0.87-- | 0.94-- | 0.84-- | 0.80-- | | | | | | | |
| Std. Err. | 0.05 | 0.07 | 0.05 | 0.04 | 0.06 | 0.06 | | | | | | | |
| N | 10 | 8 | 10 | 10 | 8 | 9 | | | | | | | |
| Combined | | | | | | | | | | | | | |
| Mean | 1.01 | 0.99 | 1.01 | 0.96 | 1.02 | 0.86 | - | - | - | - | - | - | - |
| Std. Err. | 0.04 | 0.04 | 0.05 | 0.03 | 0.06 | 0.04 | | | | | | | |
| N | 20 | 18 | 20 | 20 | 18 | 19 | | | | | | | |
| Rubricyte (/Femur × 10**6) | | | | | | | | | | | | | |
| Male | | | | | | | | | | | | | |
| Mean | 2.61 | 2.90 | 2.33 | 2.12 | 2.98 | 2.28 | | | | | | | |
| Std. Err. | 0.15 | 0.11 | 0.09 | 0.08 | 0.13 | 0.07 | | | | | | | |
| N | 10 | 10 | 10 | 10 | 10 | 10 | | | | | | | |
| Female | | | | | | | | | | | | | |
| Mean | 2.67 | 2.63 | 1.98 | 1.75 | 2.29 | 1.94 | | | | | | | |
| Std. Err. | 0.13 | 0.12 | 0.09 | 0.08 | 0.14 | 0.09 | | | | | | | |
| N | 10 | 8 | 10 | 10 | 8 | 9 | | | | | | | |
| Combined | | | | | | | | | | | | | |
| Mean | 2.64 | 2.78- | 2.15@# | 1.94@# | 2.67-- | 2.12@# | D | D | - | - | I | - | - |
| Std. Err. | 0.09 | 0.09 | 0.08 | 0.07 | 0.13 | 0.07 | | | | | | | |
| N | 20 | 18 | 20 | 20 | 18 | 19 | | | | | | | |
| Total Proliferating (/Femur × 10**6) | | | | | | | | | | | | | |
| Male | | | | | | | | | | | | | |
| Mean | 3.77 | 4.04 | 3.57 | 3.18 | 4.29 | 3.29 | | | | | | | |

TABLE 6a-continued

Bone Marrow-Erythroid Series/Femur × 10**6
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT<br>Procysteine | 0 mg/kg<br>0.0% | 0 mg/kg<br>1.0% | 50 mg/kg<br>0.0% | 500 mg/kg<br>0.0% | 50 mg/kg<br>1.0% | 500 mg/kg<br>1.0% | AZT DR at<br>% Procyst. | | | Procysteine DR at<br>mg/kg AZT | | | |
|---|---|---|---|---|---|---|---|---|---|---|---|---|---|
| | | | | | | | 0.0 | 1.0 | DIF | 0 | 50 | 500 | DIF |
| Std. Err. | 0.21 | 0.14 | 0.14 | 0.12 | 0.20 | 0.11 | | | | | | | |
| N | 10 | 10 | 10 | 10 | 10 | 10 | | | | | | | |
| Female | | | | | | | | | | | | | |
| Mean | 3.79 | 3.71 | 2.90 | 2.74 | 3.24 | 2.84 | | | | | | | |
| Std. Err. | 0.18 | 0.18 | 0.14 | 0.11 | 0.21 | 0.15 | | | | | | | |
| N | 10 | 8 | 10 | 10 | 8 | 9 | | | | | | | |
| Combined | | | | | | | | | | | | | |
| Mean | 3.78 | 3.89- | 3.24@# | 2.96@# | 3.82-- | 3.08@# | D | D | - | - | I | - | - |
| Std. Err. | 0.13 | 0.11 | 0.12 | 0.10 | 0.19 | 0.11 | | | | | | | |
| N | 20 | 18 | 20 | 20 | 18 | 19 | | | | | | | |
| | | | | Metarubricyte (/Femur × 10**6) | | | | | | | | | |
| Male | | | | | | | | | | | | | |
| Mean | 0.53 | 0.51- | 0.12@# | 0.15@# | 0.12@# | 0.10@# | D | D | - | - | - | - | - |
| Std. Err. | 0.03 | 0.03 | 0.01 | 0.01 | 0.01 | 0.01 | | | | | | | |
| N | 10 | 10 | 10 | 10 | 10 | 10 | | | | | | | |
| Female | | | | | | | | | | | | | |
| Mean | 0.49 | 0.50- | 0.22@# | 0.10@# | 0.41-- | 0.34@# | D | D | * | - | I | I | * |
| Std. Err. | 0.05 | 0.05 | 0.02 | 0.01 | 0.04 | 0.02 | | | | | | | |
| N | 10 | 8 | 10 | 10 | 8 | 9 | | | | | | | |
| Combined | | | | | | | | | | | | | |
| Mean | 0.51 | 0.50 | 0.17 | 0.13 | 0.25 | 0.22 | | | | | | | |
| Std. Err. | 0.03 | 0.03 | 0.01 | 0.01 | 0.04 | 0.03 | | | | | | | |
| N | 20 | 18 | 20 | 20 | 18 | 19 | | | | | | | |
| | | | | Total Erythroid (/Femur × 10**6) | | | | | | | | | |
| Male | | | | | | | | | | | | | |
| Mean | 4.30 | 4.55 | 3.69 | 3.34 | 4.41 | 3.39 | | | | | | | |
| Std. Err. | 0.23 | 0.15 | 0.15 | 0.12 | 0.20 | 0.11 | | | | | | | |
| N | 10 | 10 | 10 | 10 | 10 | 10 | | | | | | | |
| Female | | | | | | | | | | | | | |
| Mean | 4.29 | 4.21 | 3.12 | 2.84 | 3.65 | 3.18 | | | | | | | |
| Std. Err. | 0.20 | 0.22 | 0.15 | 0.12 | 0.25 | 0.17 | | | | | | | |
| N | 10 | 8 | 10 | 10 | 8 | 9 | | | | | | | |
| Combined | | | | | | | | | | | | | |
| Mean | 4.29 | 4.40- | 3.41@# | 3.09@# | 4.07-- | 3.29@# | D | D | - | - | I | - | - |
| Std. Err. | 0.15 | 0.13 | 0.12 | 0.10 | 0.18 | 0.10 | | | | | | | |
| N | 20 | 18 | 20 | 20 | 18 | 19 | | | | | | | |

@Indicates Difference From Group 1: 0 mg/kg AZT, 0.0% Procysteine
Indicates Difference From Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 Indicate Sexes Did Not Differ Therefore Tests Are Performed Across Sex

TABLE 7

Bone Marrow-Megakaryocytic Series %
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT<br>Procysteine | 0 mg/kg<br>0.0% | 0 mg/kg<br>1.0% | 50 mg/kg<br>0.0% | 500 mg/kg<br>0.0% | 50 mg/kg<br>1.0% | 500 mg/kg<br>1.0% | AZT DR at<br>% Procyst. | | | Procysteine DR at<br>mg/kg AZT | | | |
|---|---|---|---|---|---|---|---|---|---|---|---|---|---|
| | | | | | | | 0.0 | 1.0 | DIF | 0 | 50 | 500 | DIF |
| | | | | Megakaryoblast (%) | | | | | | | | | |
| Male | | | | | | | | | | | | | |
| Mean | 0.0 | 0.0 | 0.0 | 0.0 | 0.0 | 0.0 | | | | | | | |
| Std. Err. | 0.0 | 0.0 | 0.0 | 0.0 | 0.0 | 0.0 | | | | | | | |
| N | 10 | 10 | 10 | 10 | 10 | 10 | | | | | | | |
| Female | | | | | | | | | | | | | |
| Mean | 0.0 | 0.0 | 0.0 | 0.0 | 0.0 | 0.0 | | | | | | | |
| Std. Err. | 0.0 | 0.0 | 0.0 | 0.0 | 0.0 | 0.0 | | | | | | | |
| N | 10 | 8 | 10 | 10 | 8 | 9 | | | | | | | |
| Combined | | | | | | | | | | | | | |
| Mean | 0.0 | 0.0- | 0.0-- | 0.0-- | 0.0-- | 0.0-- | - | - | - | - | - | - | - |
| Std. Err. | 0.0 | 0.0 | 0.0 | 0.0 | 0.0 | 0.0 | | | | | | | |
| N | 20 | 18 | 20 | 20 | 18 | 19 | | | | | | | |
| | | | | Promegakaryocyte (%) | | | | | | | | | |
| Male | | | | | | | | | | | | | |

TABLE 7-continued

Bone Marrow-Megakaryocytic Series %
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| Mean | 0.0 | 0.0 | 0.0 | 0.0 | 0.0 | 0.0 | | | | | | | |
| Std. Err. | 0.0 | 0.0 | 0.0 | 0.0 | 0.0 | 0.0 | | | | | | | |
| N | 10 | 10 | 10 | 10 | 10 | 10 | | | | | | | |
| Female | | | | | | | | | | | | | |
| Mean | 0.0 | 0.0 | 0.0 | 0.0 | 0.0 | 0.0 | | | | | | | |
| Std. Err. | 0.0 | 0.0 | 0.0 | 0.0 | 0.0 | 0.0 | | | | | | | |
| N | 10 | 8 | 10 | 10 | 8 | 9 | | | | | | | |
| Combined | | | | | | | | | | | | | |
| Mean | 0.0 | 0.0- | 0.0-- | 0.0-- | 0.0-- | 0.0- | - | - | - | - | - | - | - |
| Std. Err. | 0.0 | 0.0 | 0.0 | 0.0 | 0.0 | 0.0 | | | | | | | |
| N | 20 | 18 | 20 | 20 | 18 | 19 | | | | | | | |
| Megakaryocyte (%) | | | | | | | | | | | | | |
| Male | | | | | | | | | | | | | |
| Mean | 0.0 | 0.1 | 0.0 | 0.0 | 0.1 | 0.0 | | | | | | | |
| Std. Err. | 0.0 | 0.0 | 0.0 | 0.0 | 0.0 | 0.0 | | | | | | | |
| N | 10 | 10 | 10 | 10 | 10 | 10 | | | | | | | |
| Female | | | | | | | | | | | | | |
| Mean | 0.1 | 0.1 | 0.1 | 0.1 | 0.1 | 0.1 | | | | | | | |
| Std. Err. | 0.0 | 0.0 | 0.0 | 0.0 | 0.0 | 0.0 | | | | | | | |
| N | 10 | 8 | 10 | 10 | 8 | 9 | | | | | | | |
| Combined | | | | | | | | | | | | | |
| Mean | 0.1 | 0.1- | 0.0-- | 0.1-- | 0.1-- | 0.0-- | - | - | - | - | - | - | - |
| Std. Err. | 0.0 | 0.0 | 0.0 | 0.0 | 0.0 | 0.0 | | | | | | | |
| N | 20 | 18 | 20 | 20 | 18 | 19 | | | | | | | |
| Megakaryoblast (/Femur × $10^{**}6$) | | | | | | | | | | | | | |
| Male | | | | | | | | | | | | | |
| Mean | 0.000 | 0.000 | 0.000 | 0.000 | 0.000 | 0.000 | | | | | | | |
| Std. Err. | 0.000 | 0.000 | 0.000 | 0.000 | 0.000 | 0.000 | | | | | | | |
| N | 10 | 10 | 10 | 10 | 10 | 10 | | | | | | | |
| Female | | | | | | | | | | | | | |
| Mean | 0.000 | 0.000 | 0.000 | 0.000 | 0.000 | 0.000 | | | | | | | |
| Std. Err. | 0.000 | 0.000 | 0.000 | 0.000 | 0.000 | 0.000 | | | | | | | |
| N | 10 | 8 | 10 | 10 | 8 | 9 | | | | | | | |
| Combined | | | | | | | | | | | | | |
| Mean | 0.000 | 0.000- | 0.000-- | 0.000-- | 0.000-- | 0.000-- | - | - | - | - | - | - | - |
| Std. Err. | 0.000 | 0.000 | 0.000 | 0.000 | 0.000 | 0.000 | | | | | | | |
| N | 20 | 18 | 20 | 20 | 18 | 19 | | | | | | | |

@Indicates Difference From Group 1: 0 mg/kg AZT, 0.0% Procysteine
Indicates Difference From Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 Indicate Sexes Did Not Differ Therefore Tests Are Performed Across Sex

TABLE 7a

Bone Marrow-Megakaryocytic Series/Femur × $10^{**}6$
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| Promegakaryocyte (/Femur × $10^{**}6$) | | | | | | | | | | | | | |
| Male | | | | | | | | | | | | | |
| Mean | 0.000 | 0.000 | 0.000 | 0.000 | 0.000 | 0.000 | | | | | | | |
| Std. Err. | 0.000 | 0.000 | 0.000 | 0.000 | 0.000 | 0.000 | | | | | | | |
| N | 10 | 10 | 10 | 10 | 10 | 10 | | | | | | | |
| Female | | | | | | | | | | | | | |
| Mean | 0.000 | 0.000 | 0.000 | 0.000 | 0.000 | 0.000 | | | | | | | |
| Std. Err. | 0.000 | 0.000 | 0.000 | 0.000 | 0.000 | 0.000 | | | | | | | |
| N | 10 | 8 | 10 | 10 | 8 | 9 | | | | | | | |
| Combined | | | | | | | | | | | | | |
| Mean | 0.000 | 0.000- | 0.000-- | 0.000-- | 0.000-- | 0.000-- | - | - | - | - | - | - | - |
| Std. Err. | 0.000 | 0.000 | 0.000 | 0.000 | 0.000 | 0.000 | | | | | | | |
| N | 20 | 18 | 20 | 20 | 18 | 19 | | | | | | | |
| Megakaryocyte (/Femur × $10^{**}6$) | | | | | | | | | | | | | |

TABLE 7a-continued

Bone Marrow-Megakaryocytic Series/Femur × 10**6
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| Male | | | | | | | | | | | | | |
| Mean | 0.002 | 0.010 | 0.002 | 0.004 | 0.007 | 0.002 | | | | | | | |
| Std. Err. | 0.002 | 0.004 | 0.002 | 0.003 | 0.004 | 0.002 | | | | | | | |
| N | 10 | 10 | 10 | 10 | 10 | 10 | | | | | | | |
| Female | | | | | | | | | | | | | |
| Mean | 0.010 | 0.009 | 0.007 | 0.006 | 0.004 | 0.006 | | | | | | | |
| Std. Err. | 0.004 | 0.005 | 0.003 | 0.003 | 0.003 | 0.003 | | | | | | | |
| N | 10 | 8 | 10 | 10 | 8 | 9 | | | | | | | |
| Combined | | | | | | | | | | | | | |
| Mean | 0.006 | 0.010- | 0.004-- | 0.005-- | 0.006-- | 0.004-- | - | - | - | - | - | - | - |
| Std. Err. | 0.002 | 0.003 | 0.002 | 0.002 | 0.002 | 0.002 | | | | | | | |
| N | 20 | 18 | 20 | 20 | 18 | 19 | | | | | | | |

@Indicates Difference From Group 1: 0 mg/kg AZT, 0.0% Procysteine
Indicates Difference From Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 Indicate Sexes Did Not Differ Therefore Tests Are Performed Across Sex

TABLE 8

Bone Marrow-Miscellaneous Cells %
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| Male | | | | | | | | | | | | | |
| Mean | 0.9 | 1.0- | 0.4@# | 0.2@# | 0.3@# | 0.2@# | | | | - | - | - | - |
| Std. Err. | 0.1 | 0.1 | 0.1 | 0.1 | 0.1 | 0.1 | | | | | | | |
| N | 10 | 10 | 10 | 10 | 10 | 10 | | | | | | | |
| Female | | | | | | | | | | | | | |
| Mean | 1.0 | 1.2- | 0.5@# | 0.2@# | 1.1-- | 0.8-- | | | | - | I | I | - |
| Std. Err. | 0.2 | 0.1 | 0.1 | 0.1 | 0.2 | 0.2 | | | | | | | |
| N | 10 | 8 | 10 | 10 | 8 | 9 | | | | | | | |
| Combined | | | | | | | | | | | | | |
| Mean | 1.0 | 1.1 | 0.4 | 0.2 | 0.7 | 0.5 | D | D | - | | | | |
| Std. Err. | 0.1 | 0.1 | 0.1 | 0.1 | 0.1 | 0.1 | | | | | | | |
| N | 20 | 18 | 20 | 20 | 18 | 19 | | | | | | | |
| Monocyte (%) | | | | | | | | | | | | | |
| Male | | | | | | | | | | | | | |
| Mean | 0.0 | 0.0 | 0.1 | 0.1 | 0.1 | 0.2 | | | | | | | |
| Std. Err. | 0.0 | 0.0 | 0.0 | 0.0 | 0.1 | 0.0 | | | | | | | |
| N | 10 | 10 | 10 | 10 | 10 | 10 | | | | | | | |
| Female | | | | | | | | | | | | | |
| Mean | 0.1 | 0.1 | 0.1 | 0.1 | 0.1 | 0.1 | | | | | | | |
| Std. Err. | 0.1 | 0.1 | 0.0 | 0.0 | 0.0 | 0.0 | | | | | | | |
| N | 10 | 8 | 10 | 10 | 8 | 9 | | | | | | | |
| Combined | | | | | | | | | | | | | |
| Mean | 0.1 | 0.0- | 0.1-- | 0.1-- | 0.1-- | 0.1-- | - | - | - | - | - | - | - |
| Std. Err. | 0.0 | 0.0 | 0.0 | 0.0 | 0.0 | 0.0 | | | | | | | |
| N | 20 | 18 | 20 | 20 | 18 | 19 | | | | | | | |
| Plasma Cell (%) | | | | | | | | | | | | | |
| Male | | | | | | | | | | | | | |
| Mean | 0.2 | 0.0- | 0.3-- | 0.4@# | 0.4-# | 0.4-# | | | | | | | |
| Std. Err. | 0.0 | 0.0 | 0.1 | 0.1 | 0.1 | 0.1 | | | | | | | |
| N | 10 | 10 | 10 | 10 | 10 | 10 | | | | | | | |
| Female | | | | | | | | | | | | | |
| Mean | 0.1 | 0.3- | 0.1-- | 0.1-- | 0.3-- | 0.3@- | | | | | | | |
| Std. Err. | 0.0 | 0.1 | 0.0 | 0.0 | 0.1 | 0.1 | | | | | | | |
| N | 10 | 8 | 10 | 10 | 8 | 9 | | | | | | | |
| Combined | | | | | | | | | | | | | |
| Mean | 0.1 | 0.1 | 0.2 | 0.3 | 0.3 | 0.3 | - | I | - | - | - | - | - |
| Std. Err. | 0.0 | 0.1 | 0.0 | 0.0 | 0.0 | 0.1 | | | | | | | |
| N | 20 | 18 | 20 | 20 | 18 | 19 | | | | | | | |
| Mast Cell (%) | | | | | | | | | | | | | |

TABLE 8-continued

Bone Marrow-Miscellaneous Cells %
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| Male | | | | | | | | | | | | | |
| Mean | 0.00 | 0.02 | 0.00 | 0.00 | 0.00 | 0.00 | | | | | | | |
| Std. Err. | 0.00 | 0.02 | 0.00 | 0.00 | 0.00 | 0.00 | | | | | | | |
| N | 10 | 10 | 10 | 10 | 10 | 10 | | | | | | | |
| Female | | | | | | | | | | | | | |
| Mean | 0.00 | 0.05 | 0.00 | 0.00 | 0.00 | 0.00 | | | | | | | |
| Std. Err. | 0.00 | 0.03 | 0.00 | 0.00 | 0.00 | 0.00 | | | | | | | |
| N | 10 | 8 | 10 | 10 | 8 | 9 | | | | | | | |
| Combined | | | | | | | | | | | | | |
| Mean | 0.00 | 0.03@ | 0.00-# | 0.00-# | 0.00-# | 0.00-# | - | D | * | I | - | - | - |
| Std. Err. | 0.00 | 0.02 | 0.00 | 0.00 | 0.00 | 0.00 | | | | | | | |
| N | 20 | 18 | 20 | 20 | 18 | 19 | | | | | | | |
| | | | | Reticulum Cell (%) | | | | | | | | | |
| Male | | | | | | | | | | | | | |
| Mean | 0.1 | 0.2- | 0.5-- | 0.4-- | 0.6@- | 0.5-- | | | | - | - | - | - |
| Std. Err. | 0.1 | 0.1 | 0.1 | 0.1 | 0.1 | 0.1 | | | | | | | |
| N | 10 | 10 | 10 | 10 | 10 | 10 | | | | | | | |
| Female | | | | | | | | | | | | | |
| Mean | 0.4 | 0.2- | 0.5-- | 0.8-# | 0.3-- | 0.1 | | | | - | - | D | - |
| Std. Err. | 0.2 | 0.1 | 0.1 | 0.1 | 0.1 | 0.0 | | | | | | | |
| N | 10 | 8 | 10 | 10 | 8 | 9 | | | | | | | |
| Combined | | | | | | | | | | | | | |
| Mean | 0.3 | 0.2 | 0.5 | 0.6 | 0.4 | 0.3 | I | - | - | | | | |
| Std. Err. | 0.1 | 0.1 | 0.1 | 0.1 | 0.1 | 0.1 | | | | | | | |
| N | 20 | 18 | 20 | 20 | 18 | 19 | | | | | | | |

@Indicates Difference From Group 1: 0 mg/kg AZT, 0.0% Procysteine
Indicates Difference From Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 Indicate Sexes Did Not Differ Therefore Tests Are Performed Across Sex

TABLE 8a

Bone Marrow-Miscellaneous Cells/Femur × 10**6
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| | | | Lymphocyte (/Femur × 106)** | | | | | | | | | | |
| Male | | | | | | | | | | | | | |
| Mean | 0.100 | 0.130 | 0.047 | 0.022 | 0.043 | 0.020 | | | | - | - | - | - |
| Std. Err. | 0.013 | 0.017 | 0.014 | 0.007 | 0.011 | 0.005 | | | | | | | |
| N | 10 | 10 | 10 | 10 | 10 | 10 | | | | | | | |
| Female | | | | | | | | | | | | | |
| Mean | 0.118 | 0.141 | 0.046 | 0.015 | 0.107 | 0.075 | | | | - | I | I | - |
| Std. Err. | 0.020 | 0.015 | 0.007 | 0.007 | 0.014 | 0.016 | | | | | | | |
| N | 10 | 8 | 10 | 10 | 8 | 9 | | | | | | | |
| Combined | | | | | | | | | | | | | |
| Mean | 0.109 | 0.135- | 0.047@# | 0.019@# | 0.072-# | 0.046@#D | D | - | | | | | |
| Std. Err. | 0.012 | 0.011 | 0.008 | 0.005 | 0.011 | 0.010 | | | | | | | |
| N | 20 | 18 | 20 | 20 | 18 | 19 | | | | | | | |
| | | | Monocyte (/Femur × 106)** | | | | | | | | | | |
| Male | | | | | | | | | | | | | |
| Mean | 0.005 | 0.003 | 0.011 | 0.008 | 0.018 | 0.016 | | | | | | | |
| Std. Err. | 0.003 | 0.003 | 0.004 | 0.003 | 0.009 | 0.005 | | | | | | | |
| N | 10 | 10 | 10 | 10 | 10 | 10 | | | | | | | |
| Female | | | | | | | | | | | | | |
| Mean | 0.008 | 0.006 | 0.006 | 0.008 | 0.009 | 0.006 | | | | | | | |
| Std. Err. | 0.005 | 0.006 | 0.003 | 0.005 | 0.004 | 0.003 | | | | | | | |
| N | 10 | 8 | 10 | 10 | 8 | 9 | | | | | | | |
| Combined | | | | | | | | | | | | | |
| Mean | 0.007 | 0.004- | 0.008-- | 0.008-- | 0.014-- | 0.012-- | - | - | - | - | - | - | - |
| Std. Err. | 0.003 | 0.003 | 0.002 | 0.003 | 0.005 | 0.003 | | | | | | | |
| N | 20 | 18 | 20 | 20 | 18 | 19 | | | | | | | |

TABLE 8a-continued

Bone Marrow-Miscellaneous Cells/Femur × 10**6
Listing of Means and Standard Errors; Comparison of Means to Group 1 and 2 Means
Descriptions and Comparisons of Dosage Response Effects
DR Indicates Dosage Response, i.e.. Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| *Plasma Cell (/Femur × 10**6)* | | | | | | | | | | | | | |
| Male | | | | | | | | | | | | | |
| Mean | 0.020 | 0.005- | 0.030-- | 0.045-# | 0.048@# | 0.037-# | | | | | | | |
| Std. Err. | 0.005 | 0.003 | 0.006 | 0.007 | 0.009 | 0.010 | | | | | | | |
| N | 10 | 10 | 10 | 10 | 10 | 10 | | | | | | | |
| Female | | | | | | | | | | | | | |
| Mean | 0.007 | 0.032- | 0.008-- | 0.013-- | 0.027-- | 0.029-- | | | | | | | |
| Std. Err. | 0.003 | 0.012 | 0.004 | 0.004 | 0.009 | 0.009 | | | | | | | |
| N | 10 | 8 | 10 | 10 | 8 | 9 | | | | | | | |
| Combined | | | | | | | | | | | | | |
| Mean | 0.013 | 0.017 | 0.019 | 0.029 | 0.038 | 0.033 | - | - | - | - | - | - | - |
| Std. Err. | 0.003 | 0.006 | 0.004 | 0.005 | 0.007 | 0.007 | | | | | | | |
| N | 20 | 18 | 20 | 20 | 18 | 19 | | | | | | | |
| *Mast Cell (/Femur × 10**6)* | | | | | | | | | | | | | |
| Male | | | | | | | | | | | | | |
| Mean | 0.000 | 0.003 | 0.000 | 0.000 | 0.000 | 0.000 | | | | | | | |
| Std. Err. | 0.000 | 0.003 | 0.000 | 0.000 | 0.000 | 0.000 | | | | | | | |
| N | 10 | 10 | 10 | 10 | 10 | 10 | | | | | | | |
| Female | | | | | | | | | | | | | |
| Mean | 0.000 | 0.006 | 0.000 | 0.000 | 0.000 | 0.000 | | | | | | | |
| Std. Err. | 0.000 | 0.004 | 0.000 | 0.000 | 0.000 | 0.000 | | | | | | | |
| N | 10 | 8 | 10 | 10 | 8 | 9 | | | | | | | |
| Combined | | | | | | | | | | | | | |
| Mean | 0.000 | 0.004@ | 0.000-# | 0.000-# | 0.000-# | 0.000-# | - | D | * | I | - | - | - |
| Std. Err. | 0.000 | 0.002 | 0.000 | 0.000 | 0.000 | 0.000 | | | | | | | |
| N | 20 | 18 | 20 | 20 | 18 | 19 | | | | | | | |
| *Reticulum Cell (/Femur × 10**6)* | | | | | | | | | | | | | |
| Male | | | | | | | | | | | | | |
| Mean | 0.012 | 0.021- | 0.062@- | 0.043-- | 0.068@# | 0.053-- | | | | - | - | - | - |
| Std. Err. | 0.007 | 0.010 | 0.017 | 0.014 | 0.008 | 0.015 | | | | | | | |
| N | 10 | 10 | 10 | 10 | 10 | 10 | | | | | | | |
| Female | | | | | | | | | | | | | |
| Mean | 0.043 | 0.017- | 0.056-- | 0.069-# | 0.022-- | 0.007-- | | | | - | - | D | - |
| Std. Err. | 0.018 | 0.009 | 0.015 | 0.012 | 0.011 | 0.005 | | | | | | | |
| N | 10 | 8 | 10 | 10 | 8 | 9 | | | | | | | |
| Combined | | | | | | | | | | | | | |
| Mean | 0.028 | 0.019 | 0.059 | 0.056 | 0.048 | 0.031 | - | - | - | | | | |
| Std. Err. | 0.010 | 0.007 | 0.011 | 0.009 | 0.009 | 0.010 | | | | | | | |
| N | 20 | 18 | 20 | 20 | 18 | 19 | | | | | | | |

@Indicates Difference From Group 1: 0 mg/kg AZT. 0.0% Procysteine
Indicates Difference From Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes. Blanks for DR and DIF or for Comparison to Group 1 or 2 Indicate Sexes Differ Therefore Tests Are Performed by Sex
For Each Sex, Blanks for DR and DIF or for Comparison to Group 1 or 2 Indicate Sexes Did Not Differ Therefore Tests Are Performed Across Sex

TABLE 9

Bone Marrow-Myeloid:Erythroid Ratio
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | Myeloid:Erythroid Ratio | | | | | | AZT DR at % Procyst. | | | Procysteine DR at mg/kg AZT | | | |
|---|---|---|---|---|---|---|---|---|---|---|---|---|---|
| | 0 mg/kg | 0 mg/kg | 50 mg/kg | 500 mg/kg | 50 mg/kg | 500 mg/kg | 0.0 | 1.0 | DIF | 0 | 50 | 500 | DIF |
| Procysteine | 0.0% | 1.0% | 0.0% | 0.0% | 1.0% | 1.0% | | | | | | | |
| Male | | | | | | | | | | | | | |
| Mean | 1.56 | 1.59- | 2.09@# | 2.01@# | 1.74@# | 1.77@# | I | I | * | - | D | D | * |
| Std. Err. | 0.02 | 0.02 | 0.02 | 0.02 | 0.01 | 0.02 | | | | | | | |
| N | 10 | 10 | 10 | 10 | 10 | 10 | | | | | | | |
| Female | | | | | | | | | | | | | |
| Mean | 1.58 | 1.58- | 2.01@# | 2.10@# | 1.59-- | 1.58-- | I | - | * | - | D | D | * |
| Std. Err. | 0.02 | 0.02 | 0.02 | 0.02 | 0.02 | 0.02 | | | | | | | |
| N | 10 | 8 | 10 | 10 | 8 | 9 | | | | | | | |
| Combined | | | | | | | | | | | | | |
| Mean | 1.57 | 1.59 | 2.05 | 2.06 | 1.67 | 1.68 | | | | | | | |
| Std. Err. | 0.01 | 0.01 | 0.02 | 0.02 | 0.02 | 0.03 | | | | | | | |

TABLE 9-continued

Bone Marrow-Myeloid:Erythroid Ratio
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | Myeloid:Erythroid Ratio | | | | | | AZT DR at % Procyst. | | | Procysteine DR at mg/kg AZT | | | |
|---|---|---|---|---|---|---|---|---|---|---|---|---|---|
| AZT | 0 mg/kg | 0 mg/kg | 50 mg/kg | 500 mg/kg | 50 mg/kg | 500 mg/kg | 0.0 | 1.0 | DIF | 0 | 50 | 500 | DIF |
| Procysteine | 0.0% | 1.0% | 0.0% | 0.0% | 1.0% | 1.0% | | | | | | | |
| N | 20 | 18 | 20 | 20 | 18 | 19 | | | | | | | |

@Indicates Difference From Group 1: 0 mg/kg AZT, 0.0% Procysteine
Indicates Difference from Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 indicate Sexes Did Not Differ Therefore Tests Are Performed Across Sex

TABLE 10

Bone Marrow Cells Before Plating
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | Nucleated Cells/Femur ($\times 10^{**}6$) | | | | | | AZT DR at % Procyst. | | | Procysteine DR at mg/kg AZT | | | |
|---|---|---|---|---|---|---|---|---|---|---|---|---|---|
| AZT | 0 mg/kg | 0 mg/kg | 50 mg/kg | 500 mg/kg | 50 mg/kg | 500 mg/kg | 0.0 | 1.0 | DIF | 0 | 50 | 500 | DIF |
| Procysteine | 0.0% | 1.0% | 0.0% | 0.0% | 1.0% | 1.0% | | | | | | | |
| Male | | | | | | | | | | | | | |
| Mean | 11.8 | 12.8 | 11.7 | 10.5 | 12.6 | 10.0 | | | | | | | |
| Std. Err. | 0.6 | 0.4 | 0.4 | 0.4 | 0.5 | 0.4 | | | | | | | |
| N | 10 | 10 | 10 | 10 | 10 | 10 | | | | | | | |
| Female | | | | | | | | | | | | | |
| Mean | 11.4 | 12.0 | 9.9 | 8.8 | 10.4 | 9.0 | | | | | | | |
| Std. Err. | 0.5 | 0.6 | 0.5 | 0.4 | 0.6 | 0.4 | | | | | | | |
| N | 10 | 9 | 10 | 10 | 9 | 10 | | | | | | | |
| Combined | | | | | | | | | | | | | |
| Mean | 11.6 | 12.4- | 10.8-# | 9.6@# | 11.5-- | 9.5@# | D | D | - | - | - | - | - |
| Std. Err. | 0.4 | 0.3 | 0.4 | 0.3 | 0.5 | 0.3 | | | | | | | |
| N | 20 | 19 | 20 | 20 | 19 | 20 | | | | | | | |

@Indicates Difference From Group 1: 0 mg/kg AZT, 0.0% Procysteine
Indicates Difference From Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 Indicate Sexes Did Not Differ Therefore Tests Are Performed Across Sex

TABLE 11

Colony Forming Units/$10^{**}4$ Cells Plated
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| | | | | | | | 0.0 | 1.0 | DIF | 0 | 50 | 500 | DIF |
| Procysteine | 0.0% | 1.0% | 0.0% | 0.0% | 1.0% | 1.0% | | | | | | | |
| Myeloid (No. of Colonies/$10^{**}4$ Cells Plated) | | | | | | | | | | | | | |
| Male | | | | | | | | | | | | | |
| Mean | 35.6 | 33.9 | 32.6 | 40.7 | 37.6 | 42.2 | | | | | | | |
| Std. Err. | 1.8 | 1.4 | 2.5 | 2.6 | 1.7 | 3.3 | | | | | | | |
| N | 10 | 10 | 10 | 10 | 10 | 10 | | | | | | | |
| Female | | | | | | | | | | | | | |
| Mean | 34.9 | 32.3 | 35.5 | 46.8 | 31.7 | 43.4 | | | | | | | |
| Std. Err. | 1.8 | 1.6 | 1.8 | 2.7 | 2.3 | 2.4 | | | | | | | |
| N | 10 | 9 | 10 | 10 | 9 | 10 | | | | | | | |
| Combined | | | | | | | | | | | | | |
| Mean | 35.2 | 33.1- | 34.0-- | 43.8@# | 34.8-- | 42.8@# | I | I | - | - | - | - | - |
| Std. Err. | 1.3 | 1.0 | 1.5 | 2.0 | 1.5 | 2.0 | | | | | | | |
| N | 20 | 19 | 20 | 20 | 19 | 20 | | | | | | | |
| Erythroid (No. of Colonies/$10^{**}4$ Cells Plated) | | | | | | | | | | | | | |
| Male | | | | | | | | | | | | | |
| Mean | 3.8 | 3.1 | 3.6 | 4.1 | 4.2 | 4.2 | | | | | | | |
| Std. Err. | 0.5 | 0.3 | 0.7 | 0.5 | 0.5 | 0.7 | | | | | | | |
| N | 10 | 10 | 10 | 10 | 10 | 10 | | | | | | | |

TABLE 11-continued

Colony Forming Units/10**4 Cells Plated
Listing of Means and Standard Errors; Comparison of Means to Group 1 and 2 Means
Descriptions and Comparisons of Dosage Response Effects
DR Indicates Dosage Response, i.e., Test of Slope; DIF Indicates Difference Between (Among) DR Effects

| | | | | | | | | | | | | | |
|---|---|---|---|---|---|---|---|---|---|---|---|---|---|
| Female | | | | | | | | | | | | | |
| Mean | 3.2 | 3.1 | 3.6 | 4.1 | 3.3 | 3.8 | | | | | | | |
| Std. Err. | 0.3 | 0.4 | 0.4 | 0.6 | 0.5 | 0.4 | | | | | | | |
| N | 10 | 9 | 10 | 10 | 9 | 10 | | | | | | | |
| Combined | | | | | | | | | | | | | |
| Mean | 3.5 | 3.1- | 3.6-- | 4.1-- | 3.8-- | 4.0-- | - | - | - | - | - | - | - |
| Std. Err. | 0.3 | 0.2 | 0.4 | 0.4 | 0.3 | 0.4 | | | | | | | |
| N | 20 | 19 | 20 | 20 | 19 | 20 | | | | | | | |
| Male | | | | | | | | | | | | | |
| Mean | 0.1 | 0.1 | 0.0 | 0.0 | 0.0 | 0.1 | | | | | | | |
| Std. Err. | 0.1 | 0.1 | 0.0 | 0.0 | 0.0 | 0.0 | | | | | | | |
| N | 10 | 10 | 10 | 10 | 10 | 10 | | | | | | | |
| Female | | | | | | | | | | | | | |
| Mean | 0.2 | 0.3 | 0.2 | 0.1 | 0.2 | 0.1 | | | | | | | |
| Std. Err. | 0.2 | 0.1 | 0.1 | 0.1 | 0.1 | 0.0 | | | | | | | |
| N | 10 | 9 | 10 | 10 | 9 | 10 | | | | | | | |
| Combined | | | | | | | | | | | | | |
| Mean | 0.2 | 0.2- | 0.1-- | 0.1-- | 0.1-- | 0.1-- | - | - | - | - | - | - | - |
| Std. Err. | 0.1 | 0.1 | 0.0 | 0.0 | 0.1 | 0.0 | | | | | | | |
| N | 20 | 19 | 20 | 20 | 19 | 20 | | | | | | | |
| | | | Total (No. of Colonies/10**4 Cells Plated) | | | | | | | | | | |
| Male | | | | | | | | | | | | | |
| Mean | 39.5 | 37.1 | 36.2 | 44.9 | 41.9 | 46.5 | | | | | | | |
| Std. Err. | 1.9 | 1.4 | 2.5 | 2.8 | 1.7 | 3.3 | | | | | | | |
| N | 10 | 10 | 10 | 10 | 10 | 10 | | | | | | | |
| Female | | | | | | | | | | | | | |
| Mean | 38.3 | 35.7 | 39.3 | 50.9 | 35.2 | 47.3 | | | | | | | |
| Std. Err. | 1.7 | 1.6 | 1.8 | 2.9 | 2.2 | 2.5 | | | | | | | |
| N | 10 | 9 | 10 | 10 | 9 | 10 | | | | | | | |
| Combined | | | | | | | | | | | | | |
| Mean | 38.9 | 36.4- | 37.7-- | 47.9@# | 38.7-- | 46.9@# | I | I | - | - | - | - | - |
| Std. Err. | 1.2 | 1.0 | 1.5 | 2.1 | 1.6 | 2.0 | | | | | | | |
| N | 20 | 19 | 20 | 20 | 19 | 20 | | | | | | | |

@Indicates Difference From Group 1: 0 mg/kg AZT, 0.0% Procysteine
Indicates Difference From Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 Indicate Sexes Did Not Differ Therefore Tests Are Performed Across Sex

TABLE 11a

Colony Forming Units/Femur
Listing of Means and Standard Errors; Comparison of Means to Group 1 and 2 Means
Descriptions and Comparisons of Dosage Response Effects
DR indicates Dosage Response, i.e., Test of Slope: DIF Indicates Difference Between (Among) DR Effects

| AZT | 0 mg/kg | 0 mg/kg | 50 mg/kg | 500 mg/kg | 50 mg/kg | 500 mg/kg | AZT DR at % Procyst. | | | Procysteine DR at mg/kg AZT | | | |
|---|---|---|---|---|---|---|---|---|---|---|---|---|---|
| Procysteine | 0.0% | 1.0% | 0.0% | 0.0% | 1.0% | 1.0% | 0.0 | 1.0 | DIF | 0 | 50 | 500 | DIF |
| | | | Myeloid (No. of Colonies/Femur) | | | | | | | | | | |
| Male | | | | | | | | | | | | | |
| Mean | 42307 | 43463 | 37791 | 42343 | 47641 | 41598 | | | | | | | |
| Std. Err. | 3507 | 2652 | 2909 | 2405 | 3163 | 2702 | | | | | | | |
| N | 10 | 10 | 10 | 10 | 10 | 10 | | | | | | | |
| Female | | | | | | | | | | | | | |
| Mean | 39939 | 38527 | 35617 | 40695 | 33137 | 39265 | | | | | | | |
| Std. Err. | 3104 | 2590 | 3126 | 2271 | 3373 | 3068 | | | | | | | |
| N | 10 | 9 | 10 | 10 | 9 | 10 | | | | | | | |
| Combined | | | | | | | | | | | | | |
| Mean | 41123 | 41125- | 36704-- | 41519-- | 40771-- | 40432-- | - | - | - | - | - | - | - |
| Std. Err. | 2295 | 1898 | 2093 | 1621 | 2818 | 2008 | | | | | | | |
| N | 20 | 19 | 20 | 20 | 19 | 20 | | | | | | | |
| | | | Erythroid (No. of Colonies/Femur) | | | | | | | | | | |
| Male | | | | | | | | | | | | | |
| Mean | 4705 | 3937 | 4034 | 4414 | 5414 | 4253 | | | | | | | |
| Std. Err. | 746 | 405 | 792 | 564 | 654 | 747 | | | | | | | |
| N | 10 | 10 | 10 | 10 | 10 | 10 | | | | | | | |
| Female | | | | | | | | | | | | | |
| Mean | 3672 | 3701 | 3570 | 3443 | 3460 | 3490 | | | | | | | |
| Std. Err. | 369 | 447 | 385 | 536 | 633 | 506 | | | | | | | |

TABLE 11a-continued

| | | | | | | |
|---|---|---|---|---|---|---|
| N Combined | 10 | 9 | 10 | 10 | 9 | 10 |
| Mean | 4189 | 3825- | 3802-- | 3929-- | 4488-- | 3872-- - - - - - - - |
| Std. Err. | 422 | 293 | 432 | 395 | 500 | 448 |
| N | 20 | 19 | 20 | 20 | 19 | 20 |
| | | | Mixed (No. of Colonies/Femur) | | | |
| Male | | | | | | |
| Mean | 170 | 125 | 0 | 40 | 50 | 63 |
| Std. Err. | 125 | 64 | 0 | 40 | 50 | 42 |
| N | 10 | 10 | 10 | 10 | 10 | 10 |
| Female | | | | | | |
| Mean | 317 | 317 | 182 | 91 | 202 | 52 |
| Std. Err. | 228 | 180 | 83 | 47 | 121 | 34 |
| N | 10 | 9 | 10 | 10 | 9 | 10 |
| Combined | | | | | | |
| Mean | 243 | 216- | 91-- | 66-- | 122-- | 58-- - - - - - - - |
| Std. Err. | 128 | 92 | 45 | 31 | 64 | 27 |
| N | 20 | 19 | 20 | 20 | 19 | 20 |
| | | | Total (No. of Colonies/Femur) | | | |
| Male | | | | | | |
| Mean | 47182 | 47525 | 41824 | 46797 | 53105 | 45914 |
| Std. Err. | 3976 | 2790 | 2753 | 2774 | 3471 | 2662 |
| N | 10 | 10 | 10 | 10 | 10 | 10 |
| Female | | | | | | |
| Mean | 43928 | 42544 | 39369 | 44229 | 36799 | 42807 |
| Std. Err. | 3254 | 2638 | 3298 | 2291 | 3536 | 3378 |
| N | 10 | 9 | 10 | 10 | 9 | 10 |
| Combined | | | | | | |
| Mean | 45555 | 45166- | 40596-- | 45513-- | 45361-- | 44361-- - - - - - - - |
| Std. Err. | 2528 | 1964 | 2109 | 1775 | 3080 | 2123 |
| N | 20 | 19 | 20 | 20 | 19 | 20 |

@Indicates Difference From Group 1: 0 mg/kg AZT, 0.0% Procysteine
Indicates Difference From Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 Indicate Sexes Did Not Differ Therefore Tests Are Performed Across Sex

TABLE 12

Gross Liver Findings
Listing of Counts for Animals in Blocks 2-5; Comparison of Counts to Group 1 and 2 Counts
Description and Comparisons of Dosage Response Effects
DR Indicates Dosage Response, i.e., Test of Slope; DIF Indicates Difference Between (Among) DR Effects

| | Lesion Incidence | | | | | | AZT DR at % Procyst. | | | Procysteine DR at mg/kg AZT | | | |
|---|---|---|---|---|---|---|---|---|---|---|---|---|---|
| AZT | 0 mg/kg | 0 mg/kg | 50 mg/kg | 500 mg/kg | 50 mg/kg | 500 mg/kg | 0.0 | 1.0 | DIF | 0 | 50 | 500 | DIF |
| Procysteine | 0.0% | 1.0% | 0.0% | 0.0% | 1.0% | 1.0% | | | | | | | |
| Male | | | | | | | | | | | | | |
| Count | 4 | 5 | 2 | 4 | 2 | 5 | | | | | | | |
| N | 8 | 8 | 8 | 8 | 8 | 8 | | | | | | | |
| Female | | | | | | | | | | | | | |
| Count | 0 | 2 | 0 | 5 | 3 | 3 | | | | | | | |
| N | 8 | 7 | 8 | 8 | 7 | 8 | | | | | | | |
| Combined | | | | | | | | | | | | | |
| Count | 4 | 7- | 2-- | 9-- | 5-- | 8-- | - | - | - | - | - | - | - |
| N | 16 | 15 | 16 | 16 | 15 | 16 | | | | | | | |

@Indicates Difference From Group 1: 0 mg/kg AZT, 0.0% Procysteine
Indicates Difference From Group 2: 0 mg/kg AZT, 1.0% Procysteine
-Indicates Not Significant DR, DIF or Comparison to Group 1 or 2
D Indicates Decreasing DR
I Indicates Increasing DR
*Indicates Significant DIF at Alpha = 0.01
For Combined Sexes, Blanks for DR and DIF or for Comparison to Group 1 or 2 Indicate Sexes Differ Therefore Tests Are Performed by Sex
For Each Sex, Blanks for DR and DIF or for Comparison to Group 1 or 2 Indicate Sexes Did Not Differ Therefore Tests Are Performed Across Sex

Results and Analysis

Terminal blood was evaluated for hematological effects, and bone marrow smears and aspirates were counted and $10^4$ nucleated cells of the aspirate were cultured 14 days to assess hematopoietic progenitor cells. Anemia, evidenced by significant ($p<0.01$) decreases in total hemoglobin concentration, hematocrit and erythrocyte counts, and increases in mean corpuscular volume, mean corpuscular hemoglobin and the incidence of polychromasia, anisocytosis, macrocytes and Howell-Jolly bodies, was similarly observed across both sexes for AZT and AZT/Procysteine®-treated groups.

Bone marrow aspirates exhibited a significant reduction in nucleated cells for AZT and high-dose AZT/Procysteine®-treated groups compared to controls. No group differences were noted in burst forming units-erythroid for marrow cultures, however, a significant induction was observed in total colonies and colony forming units-granulocyte/macrophage for AZT and AZT/Procysteine ® groups.

Microscopic analysis of the bone marrow smears was conducted by evaluating 500 cells for the differential analysis and 500 cells for the myeloid: erythroid ratio.

Bone marrow smears of AZT-treated mice had a reduced total count of erythroid series cells due to a marked reduction of metarubricytes (nonproliferating) and a mild reduction of rubriblasts. AZT/Procysteine®-treated mice had a significantly less severe decrease in erythroid counts than did the AZT-only treated animals, with the rubriblast, rubricyte and metarubricyte (female) counts being similar to control values.

AZT significantly increased the proliferating compartment of the myeloid series, with a reduction in the nonproliferating compartment. The AZT/Procysteine ® treated mice had a less severe increase in the proliferating myeloid compartment compared to the AZT-only treated mice. The myeloid:erythroid ratios for AZT groups were significantly increased whereas those for AZT/Procysteine ® groups were at control level.

In conclusion, these results indicate that the coadministration of Procysteine ® with AZT should reduce at least some indices of AZT-induced hematotoxicity.

EXAMPLE NO. 2

An eight week evaluation of the potential for oral Procysteine ® to modulate AZT-induced hematologic toxicity in mice was conducted. As noted above, AZT-related bone marrow toxicity, and resultant bone marrow hypoplasia, limits the utility of this drug. The objective of this study was to evaluate the hematologic response (peripheral blood and bone marrow) of mice treated by gavage twice daily for 56 days with 3'-azido-3'-deoxythymidine (AZT) while being administered L-2-oxothiazolidine-4-carboxylate (Procysteine®) orally in the feed.

Test and Control Articles

The test article, L-2-oxothiazolidine-4-carboxylate (Procysteine®), was provided by Clintec Technologies, Inc., Deerfield, Ill. Diet (MEAL) containing 1.0% (wt/wt) Procysteine®. The control diet consisted of MEAL containing no Procysteine®. Purina Mills, Inc., St. Louis, Mo., provided MEAL (used as the control diet and used to formulate the Procysteinee-containing diet). The positive control article, 3'-azido-3'-deoxythymidine (AZT), CAS: 30516-87-1, lot #91/0037-023-B, was obtained from Burroughs Wellcome Co., Research Triangle Park, N.C. AZT was formulated at 2.5 and 25 mg/ml in 0.5% (wt/vol) aqueous methylcellulose and dispensed into amber glass bottles. Methylcellulose, CAS: 9004-67-5, lot #50H0210, obtained from Sigma Chemical Co., St. Louis, Mo., 0.5% (wt/vol) in sterile water, was used as the vehicle control.

The control diet and diet containing Procysteine® were stored at room temperature in sealed containers in either a room adjacent to the study room or in the feed storage area. A fume hood was used during: 1) dispensing of diet into feeders, 2) daily weighing of clean feeders containing fresh feed and used feeders containing left over feed, and 3) weighing, formulating and dispensing of AZT into bottles. The vehicle control solution and AZT formulations were stored refrigerated at 5±3° C. At each gavage dosing period, one bottle of each type of dosing article was removed from the refrigerator approximately 30–60 minutes before dosing and maintained at room temperature with stirring until the completion of dosing (AZT) or the initiation of dosing (methylcellulose). Starting on study day 3, a fume hood was used during twice daily treatment of mice by gavage.

Experimental Design 60 male and 60 female mice obtained from Charles River Laboratories, Portage, Mich. were used for the study. The mice were approximately 7–8 weeks old at the start of the study and the weight ranged from 20–24 g for males and 18–21 g for females.

The experimental design for treating animals is shown in Table 1. On study days 0–58, mice were fed either control diet (groups 1, 3, and 4) or diet containing 1.0% (wt/wt) Procysteine ® (groups 2, 5, and Mice were treated by gavage twice daily (morning and afternoon) on study days 3–58. Mice in groups 1 and 2 were treated with a vehicle control (0.5% aqueous methylcellulose); mice in groups 3 and 5 were treated with AZT at 50 mg/kg body weight/day; mice in groups 4 and 6 were treated with AZT at 500 mg/kg body weight/day. Mice were weighed before the first treatment every day to calculate dosage. Mice were generally treated starting at approximately 9 a.m. and 3 p.m., receiving ½ of the daily dose at each treatment. Mice were treated at each time point using a volume of approximately 10 ml/kg body weight. Animals were weighed (not fasted) on study day 59 and euthanized, and specimens were collected as described.

TABLE 1

Experimental Design for Treating Mice with AZT and Procysteine ®

| Group No. | AZT Daily Dosage[a] (mg/kg) (starting day 3) | Procysteine ® (% of Diet) (starting Day 0) | No. Mice/Group (male/female) |
|---|---|---|---|
| 1 | 0 | 0 | 10/10 |
| 2 | 0 | 1.0 | 10/10 |
| 3 | 50 | 0 | 10/10 |
| 4 | 500 | 0 | 10/10 |
| 5 | 50 | 1.0 | 10/10 |
| 6 | 500 | 1.0 | 10/10 |

[a]AZT was administered by gavage at ½ the daily dosage, twice daily for 56 days in a volume of approximately 10 ml/kg body weight. AZT was formulated at 2.5 and 25 mg/ml for the 50 and 500 mg/kg body weight treatments, respectively. Feeding of Procysteine ® diet was initiated 3 days prior to the start of AZT dosing.

Only mice showing no signs of clinical illness were used in this study. The mice were derived from a colony which was barrier raised and free of adventitious pathogens.

Animals scheduled for termination were anesthetized with methoxyflurane. After blood collection, mice were euthanized by exsanguination followed by cervical dislocation.

Mice were housed individually in suspended stainless-steel cages. Mice received Certified Rodent Diet—MEAL (Ralston Purina Co., St. Louis, Mo.). Three days prior to the initiation of AZT treatment, mice in groups 2, 5, and 6 were placed on diet containing 1.0% (wt/wt) Procysteine ®. Diet was put into dishes placed in each cage. Feed consumption was monitored on a daily basis for all animals; monitoring consumption was monitored on a daily basis for all animals; monitoring was initiated for a block of mice upon commencement of Procysteine ® feeding to animals within that block. Drinking water was provided ad libitum through demand-controlled valves in each cage.

To accommodate the necropsy procedure, animals were assigned to 1 of 5 blocks with initiation of treatment occurring on 5 consecutive days (i.e., study day 0 for block 2 was one day after study day 0 for block 1, and so on). Male mice were numbered from 1 through 60, female mice from 61 through 120, according to their initial body weight at the time of selection. For a given sex of animal, the heavier the animal, the smaller the number assigned.

Mice were treated according to block, in ascending group order; per block, males were treated first, followed by females. For example, Procysteine ® treatment started for block 1 on study day 0; the next day was study day 1 for block 1 and study day 0 for block 2, and so on. At any given gavage period (a.m. or p.m.), all males and females of a given block were treated before mice from the next block were started.

At approximately 3 p.m. on study day 0, animals were placed on a measured amount of diet (at least approximately 11 g/day) containing 0 or 1% (wt/wt) Procysteine ®, as appropriate. At approximately 7 a.m. on each of the succeeding days, the feed containers were removed, weighed, cleaned, and fresh diet added. Containers were returned to the cages at approximately 3 p.m. each day except study day 59. Starting at approximately 9 a.m. and 3 p.m. on study days 3–58, mice were treated by gavage with approximately 10 ml/kg body weight for vehicle control or positive control (AZT formulated at 2.5 and 25 mg/ml for the 50 and 500 mg/kg body weight treatments, respectively).

On study day 59, surviving mice were deeply anesthetized with methoxyflurane in a bell jar. While the mice were deeply anesthetized, blood for hematological analysis was obtained via cardiac puncture using needles/syringes coated with $K_3EDTA$. While deeply anesthetized, the mice were then euthanized by exsanguination followed by cervical dislocation. Then, bone marrow smears and aspirates were prepared and liver and kidneys were collected as subsequently described in this report.

One femur from each mouse was removed and transversely halved. One half was preserved in 10% neutral buffered formalin, then submitted to a histology department for further preparation. The other half of the femur was used to prepare bone marrow smears. A small quantity of bone marrow was extracted from the femur using a small brush previously dipped in mouse serum, then brushed onto 3 slides. The bone marrow slides were dipped (five times for approximately one second each time) into Diff-Quik ® fixative and allowed to air dry. Prepared slides for bone sections and bone marrow smears were stained (Diff-Quik ®) and the smears and sections were evaluated microscopically.

The following hematology assays were conducted:
Leukocyte count (WBC)
Erythrocyte count (RBC)
Total hemoglobin concentration (HGB)
Hematocrit (HCT)
Mean corpuscular volume (MCV)
Mean corpuscular hemoglobin (MCH)
Mean corpuscular hemoglobin concentration (MCHC)
Platelet count (Plat)
Reticulocyte count (Retic)
Differential leukocyte count GSH concentrations in blood, liver, and kidney were assayed using a method based upon reverse-phase HPLC with electrochemical detection. Blood and tissues were rapidly processed by methods that minimized oxidation of GSH. An aliquot ($\approx 20$–$50$ $\mu$l) of blood was transferred to a tube, deproteinized with 5% metaphosphoric acid, and centrifuged. Liver and kidneys were removed from the mice, weighed, homogenized (20% w/v) in 5% metaphosphoric acid, and aliquots were centrifuged. Tissue and whole blood supernatants were stored frozen at approximately $-70°$ C. until analyzed using HPLC.

Bone marrow colony-forming cells were evaluated. During necropsy, one femur per mouse was cut at the distal and proximal ends. Using a syringe and 25 G needle, 5 ml of Iscove's Modified Dulbecco's Media (IMDM) was flushed through the femur into a collection tube (2.5 ml flushed into one end, then 2.5 ml into the other end). The tube was washed using IMDM containing 20% fetal bovine serum and the cell concentration was adjusted to the desired count for the colony assay. In triplicate, the marrow cells were put into a mixture of methylcellulose, stem cell factor, interleukin-3, granulocyte macrophage—colony stimulating factor, and erythropoietin, and plated into 35 mm diameter dishes. The dishes were incubated 10 days (37° C., 5% $CO_2$, 100% relative humidity) then manually scored under a light microscope for myeloid (white), erythroid (red), and mixed colonies.

Statistical tests were performed at $\alpha \approx 0.01$. Listings of the individual data were provided. Summary statistics by sex (mean, standard error and sample size) were provided for the responses for each group and for the differences between groups 1 and 2, between groups 3 and 5 and between groups 4 and 6. The average across weekly intervals for body weight change from study day 3 was analyzed. The average across weekly intervals for food consumption starting with the interval between days 3–4 were analyzed. The model included factors for block, sex and group effects and the group by sex interaction. the interactions with block effect were assumed negligible. Data for both sexes were included in one model to get an overall estimate of the residual standard deviation used in the statistical comparisons.

The interaction of Procysteine ® and AZT was evaluated as follows: the difference between the means for group 1 and group 2 was considered a control delta. The difference between the means for groups 3 and 5 and the difference between the means for groups 4 and 6 were compared to the control delta. The significance of the two individual comparisons is designated in the summary statistics listing. Pairwise comparisons of the mean response for group 2 to group 1, group 3 to group 1, group 4 to group 1, group 5 to group 2, and group 6 to group 2 were also performed. The significance of these five comparisons was designated in the summary statistics listing. In total, the significance of seven statistical comparisons (two on the mean differences and five on the mean responses) are indicated in the summary statistics listing.

TABLE 2

| | \multicolumn{9}{c}{Hematology Results from Mice Treated with AZT/Procysteine ®} |
|---|---|---|---|---|---|---|---|---|---|
| Sex | WBC (10³/μl) | RBC (10⁶/μl) | HGB (g/dl) | HCT (%) | MCV (fl) | MCH (pg) | MCHC (g/dl) | Plate. (10³/μl) | Retic (%) |

| Sex | WBC (10³/μl) | RBC (10⁶/μl) | HGB (g/dl) | HCT (%) | MCV (fl) | MCH (pg) | MCHC (g/dl) | Plate. (10³/μl) | Retic (%) |
|---|---|---|---|---|---|---|---|---|---|
| Vehicle | | | | | | | | | |
| *Male* | | | | | | | | | |
| Mean | 1.8 | 7.87 | 13.6 | 39.6 | 52 | 17.3 | 34.3 | 882 | 1.3 |
| S.E. | 0.1 | 0.06 | 0.2 | 0.5 | 1 | 0.2 | 0.3 | 58 | 0.1 |
| n | 10 | 10 | 10 | 10 | 10 | 10 | 10 | 10 | 10 |
| *Female* | | | | | | | | | |
| Mean | 2.2 | 7.76 | 13.7 | 39.1 | 52 | 17.7 | 35.1 | 820 | 1.4 |
| S.E. | 0.2 | 0.12 | 0.2 | 0.7 | 1 | 0.3 | 0.4 | 36 | 0.1 |
| n | 10 | 10 | 10 | 10 | 10 | 10 | 10 | 10 | 10 |
| Vehicle + Procysteine ® | | | | | | | | | |
| *Male* | | | | | | | | | |
| Mean | 2.1 | 7.95 | 13.9 | 39.6 | 51 | 17.5 | 35.0 | 930 | 1.4 |
| S.E. | 0.1 | 0.06 | 0.1 | 0.4 | 0 | 0.2 | 0.3 | 46 | 0.1 |
| n | 10 | 10 | 10 | 10 | 10 | 10 | 10 | 10 | 10 |
| *Female* | | | | | | | | | |
| Mean | 2.1 | 7.98 | 13.8 | 39.6 | 51 | 17.4 | 34.9 | 918 | 1.4 |
| S.E. | 0.2 | 0.15 | 0.2 | 0.7 | 1 | 0.3 | 0.5 | 39 | 0.1 |
| n | 9 | 9 | 9 | 9 | 9 | 9 | 9 | 9 | 9 |
| 50 mg/kg AZT | | | | | | | | | |
| *Male* | | | | | | | | | |
| Mean | 2.0- | 7.08@ | 13.0@ | 38.1- | 55@ | 18.4@ | 34.3- | 990- | 1.5- |
| S.E. | 0.1 | 0.09 | 0.2 | 0.6 | 1 | 0.1 | 0.3 | 42 | 0.1 |
| n | 10 | 10 | 10 | 10 | 10 | 10 | 10 | 10 | 10 |
| *Female* | | | | | | | | | |
| Mean | 1.8- | 6.74@ | 13.0@ | 37.7@ | 57@ | 19.3@ | 34.5- | 1066@ | 1.3- |
| S.E. | 0.1 | 0.06 | 0.1 | 0.4 | 1 | 0.3 | 0.3 | 70 | 0.1 |
| n | 10 | 10 | 10 | 10 | 10 | 10 | 10 | 10 | 10 |
| 500 mg/kg AZT | | | | | | | | | |
| *Male* | | | | | | | | | |
| Mean | 1.8- | 5.45@ | 11.8@ | 35.1@ | 66@ | 21.8@ | 33.8- | 1108- | 1.4- |
| S.E. | 0.2 | 0.07 | 0.1 | 0.7 | 1 | 0.2 | 0.4 | 67 | 0.1 |
| n | 9 | 9 | 9 | 9 | 9 | 9 | 9 | 9 | 9 |
| *Female* | | | | | | | | | |
| Mean | 1.7- | 5.21@ | 11.6@ | 34.5@ | 67@ | 22.3@ | 33.7- | 1143@ | 1.6- |
| S.E. | 0.1 | 0.08 | 0.1 | 0.6 | 1 | 0.3 | 0.4 | 104 | 0.1 |
| n | 10 | 10 | 10 | 10 | 10 | 10 | 10 | 10 | 10 |
| 50 mg/kg AZT + Procysteine ® | | | | | | | | | |
| *Male* | | | | | | | | | |
| Mean | 1.8- | 6.96# | 13.0# | 37.8# | 55# | 18.8# | 34.5- | 996- | 1.3- |
| S.E. | 0.1 | 0.10 | 0.1 | 0.5 | 1 | 0.3 | 0.4 | 56 | 0.1 |
| n | 9 | 9 | 9 | 9 | 9 | 9 | 9 | 9 | 9 |
| *Female* | | | | | | | | | |
| Mean | 1.6- | 6.82# | 13.0# | 38.0- | 57# | 19.1# | 34.2- | 916- | 1.2- |
| S.E. | 0.1 | 0.08 | 0.2 | 0.7 | 1 | 0.2 | 0.3 | 66 | 0.1 |
| n | 8 | 8 | 8 | 8 | 8 | 8 | 8 | 8 | 8 |
| 500 mg/kg AZT + Procysteine ® | | | | | | | | | |
| *Male* | | | | | | | | | |
| Mean | 1.8- | 5.36# | 11.5# | 34.7# | 66# | 21.6# | 33.3# | 1234# | 1.6- |
| S.E. | 0.2 | 0.11 | 0.1 | 0.6 | 1 | 0.2 | 0.4 | 99 | 0.1 |
| n | 10 | 10 | 10 | 10 | 10 | 10 | 10 | 10 | 10 |
| *Female* | | | | | | | | | |
| Mean | 1.5- | 5.14# | 11.5# | 33.4# | 66# | 22.4# | 34.5- | 1101- | 1.5- |
| S.E. | 0.1 | 0.07 | 0.1 | 0.5 | 1 | 0.2 | 0.5 | 114 | 0.1 |
| n | 10 | 10 | 10 | 10 | 10 | 10 | 10 | 10 | 10 |

@Difference ($p < 0.01$) in pairwise comparison to vehicle group (group 1)
Difference ($p < 0.01$) in pairwise comparison to vehicle + Procysteine @ group (group 2)
-Not significantly different than matched control ($p \geq 0.01$)

Significant decreases were observed in RBC and HGB for all AZT-treated groups compared to controls, regardless of whether Procysteine ® was coadministered.

A significant decrease in HCT was observed for the high dose AZT-treated groups compared to controls, regardless of whether Procysteine ® was coadministered. Compared to their respective control groups, a significant decrease in HCT was observed for the low dose AZT-treated females, and the low dose AZT/- Procysteine ® treated males.

Significant increases in MCV and MCH were observed for all AZT-treated groups compared to controls, regardless of whether Procysteine ® was coadministered. Although the MCV and MCH were significantly increased for all AZT-treated groups, the only significant group difference observed in MCHC was a decrease for the high dose AZT/Procysteinee-treated males compared to the respective control mice.

Compared to controls, significant increases in platelets were observed for females of AZT-only-treated groups and for males of AZT/Procysteinee-treated groups.

Compared to controls, no significant differences in reticulocyte or WBC counts were observed.

Statistical analysis of bone marrow data included an analysis of the results from bone marrow smears (differential count and M:E ratio), analysis of the histopathologic characterization data for bone marrow cellularity, analysis of the bone marrow cellularity on the day of necropsy, analysis of the results of the hematopoietic colony forming assays (based on $10^4$ mononuclear bone marrow (cells/dish), and analysis of the number of colony forming units represented per femur (cellularity data multiplied by colony forming data).

The conclusion with respect to bone marrow is as follows: Under the conditions of this study, the male and female mice treated by gavage twice daily for 56 days with 3'-azido-3'-deoxythymidine (AZT) while being administered L-2-oxothiazolidine-4-carboxylate (Procysteine ®) orally in the feed showed a treatmentrelated increase in the erythroid compartment in the femoral bone marrow over that of the AZT only treated animals. In addition, the AZT/Procysteine ® treated animals had a reduction in myeloid cell count alterations as compared to AZT only treated animals. There did not appear to be a strong relationship between AZT and dose when used in combination with the Procysteine ® and the degree of response. Procysteine ®-treated female mice had only a mild decrease in erythroid series cells and no meaningful alterations in myeloid series cells. Procysteine ®-treated male mice had normal bone marrows. The AZT/Procysteine ® combination had less of an affect on the bone marrow components of male and female mice than did AZT alone.

Bone Marrow Histology

Data are summarized in Table 3.

Bone marrow histopathology revealed erythroid or general bone-marrow-hypoplasia (36/39 mice) at both doses for AZT-only treated mice. In contrast, bone marrow histology was normal in 16/20 male and 7/18 female mice cotreated with AZT/Procysteine ®. Slight, minimal or mild erythroid hypoplasia was observed in 19/20 female and 14/19 male AZT-only treated mice. In contrast, only 2/18 female and 2/20 male AZT/Procysteine ®-cotreated mice exhibited erythroid hypoplasia. The bizarre mitotic figures observed in the AZT/±Procysteine ®-treated groups were likely related to unsynchronized nuclear and cytoplasmic maturation secondary to a slightly macrocytic, AZT-induced anemia.

The biological relevance of the presence of slight quantities of hemosiderin pigment in some of the slides is not clear; this is a common, if not expected, finding during anemia. Given the type of histological stain used, the presence of any other types of iron or iron storage forms was not capable of being visualized. Although there was a significant increase in the incidence of hemosiderin for females in the low dose AZT/Procysteine ®-treated groups compared to controls, only slight amounts of hemosiderin were present in some of the slides. Since hemosiderin can be phagocytized, the lack of its presence does not rule out its prior presence. Additionally, reducing compounds such as cysteine and GSH can affect release of iron from storage forms, and Procysteine ®-treatment, by altering the dynamics of iron storage, may have actually made more iron available for erythropoiesis.

Quantitation of cells in bone marrow smears reflected the histologic changes, with a significant reduction in erythroid cells for AZT-treated mice, and marked im-

TABLE 3

Histopathological Summary of Femoral Bone Marrow Sections from Mice Treated with AZT and/or Procysteine ® for 8 Weeks

| AZT* (mb/kg/day) | Procysteine (%) | N | Normal | General Hypoplasia | Erythroid Hypoplasia | Bizarre Mitotic Figures | Hemosiderin |
|---|---|---|---|---|---|---|---|
| Females |||||||| 
| 0 | 0 | 10 | 10 | 0 | 0 | 0 | 0 |
| 0 | 1 | 9 | 9 | 0 | 0 | 0 | 0 |
| 50 | 0 | 10 | 0 | 1 | 10 | 0 | 0 |
| 50 | 1 | 8 | 2 | 0 | 0 | 0 | 6 |
| 500 | 0 | 10 | 1 | 1 | 9 | 0 | 4 |
| 500 | 1 | 10 | 5 | 0 | 2 | 3 | 4 |
| Males ||||||||
| 0 | 0 | 10 | 10 | 0 | 0 | 0 | 0 |
| 0 | 1 | 10 | 10 | 0 | 0 | 0 | 0 |
| 50 | 0 | 10 | 4 | 1 | 6 | 0 | 0 |
| 50 | 1 | 10 | 9 | 0 | 1 | 0 | 0 |
| 500 | 0 | 9 | 0 | 0 | 8 | 1 | 2 |
| 500 | 1 | 10 | 7 | 2 | 1 | 1 | 2 |

*Administered twice daily ($\simeq$ 9 a.m. and 3 p.m.) by gavage at half the daily dosage.
Administered in the feed.

Figure 2:
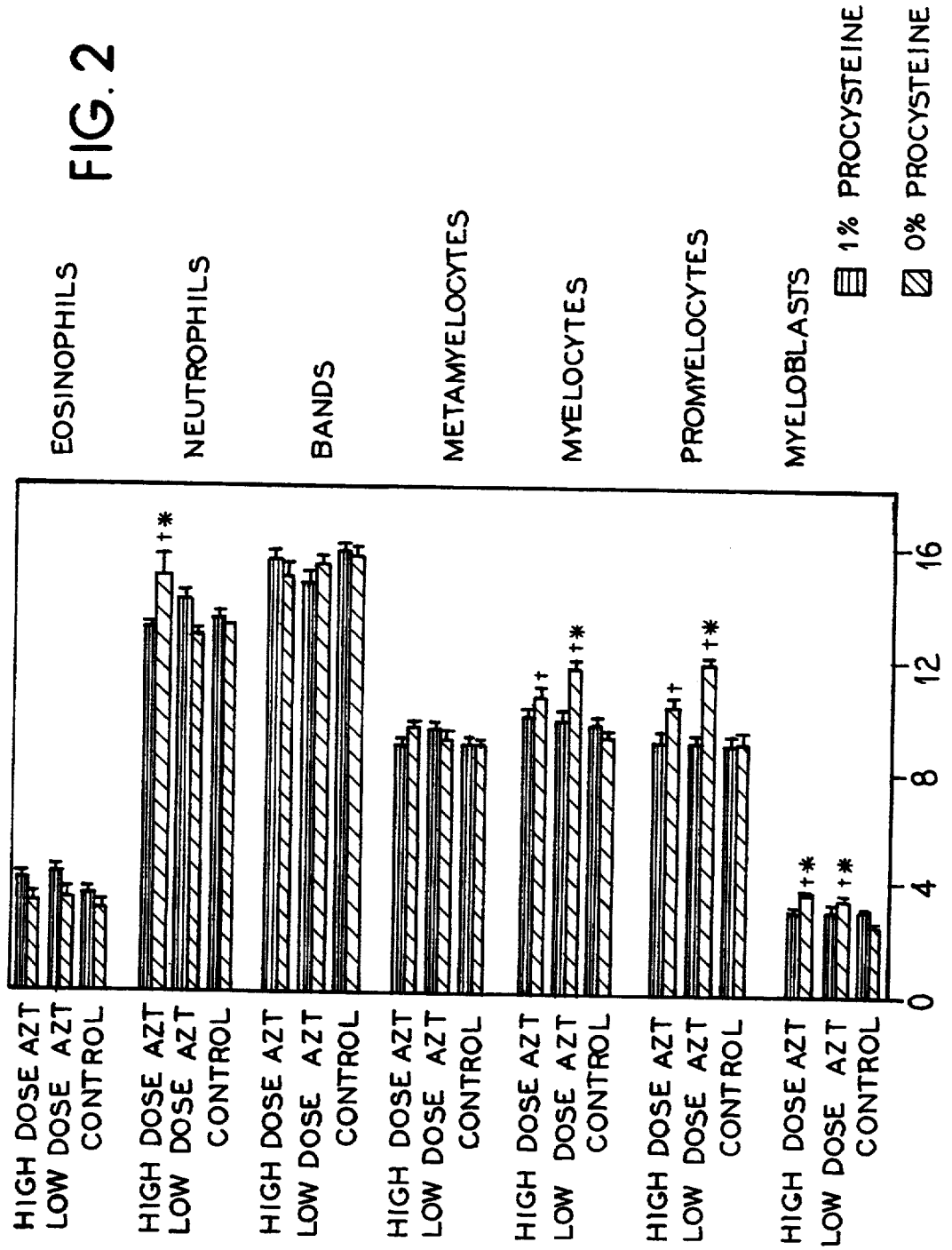
Figure 3:
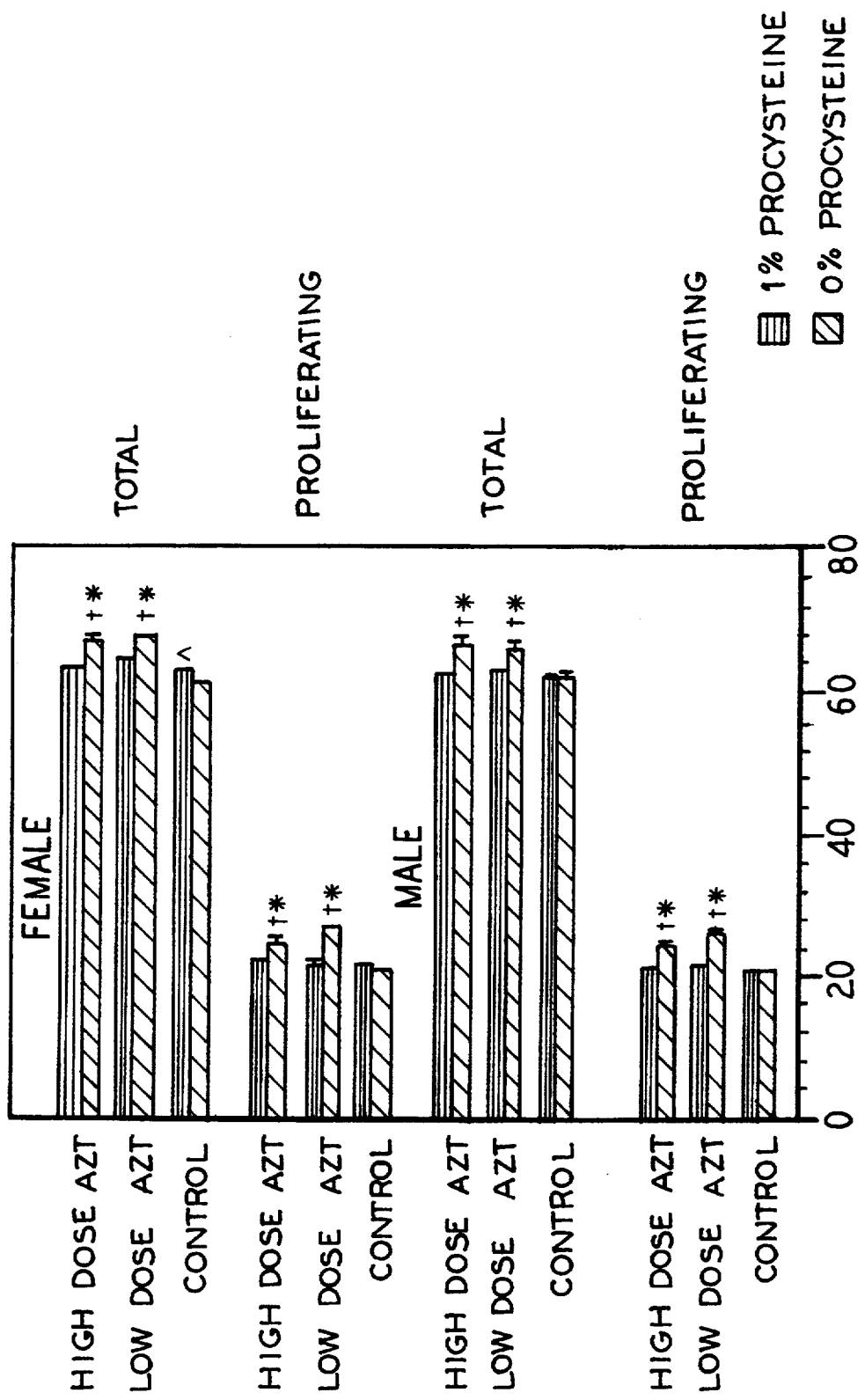

The data from the bone marrow differential are summarized in FIGS. 1-7.

Discussion

AZT is a primary treatment for AIDS. However, AZT causes a poorly regenerative, macrocytic-type anemia, neutropenia and generalized bone marrow failure that becomes dose-limiting in many humans after long term therapy. The study demonstrated that Procysteine ® significantly ameliorated AZT-induced bone marrow pathology after eight weeks of drug coadministration to mice.

provement or near normal counts for AZT/Procysteine ®-cotreated mice. Bone marrow smears of male and female AZT-only treated mice had a significantly reduced total count of erythroid series cells due to significantly reduced metarubricytes (nonproliferating) and rubriblasts. AZT/Procysteine ®-treated male and female mice had a significantly less severe decrease in total erythroid counts than did the AZT-only treated animals due to significant interaction effects on metarubricytes (high dose AZT) and rubricytes (low and high AZT doses). A significant interaction between Procysteine ® and AZT was responsible for a significantly less severe affect of AZT/Procysteine ® cotreatment than AZT-only treatment on total proliferating erythroid series cells at both AZT doses for females and at the low dose for males.

Whereas male and female AZT-only treated groups exhibited significantly increased total proliferating myeloid and total myeloid cells, AZT/Procysteine ® cotreated groups did not. A significant interaction between Procysteine ® and AZT was responsible for significantly less severe affect of AZT/Procysteine ® cotreatment than AZT-only treatment on total proliferating myeloid cells and total myeloid cells at both AZT doses for male and females. M:E ratios were significantly increased for males and females in AZT-only treated groups, but were not significantly different than controls for AZT/Procysteine ®-treated groups. At both doses of AZT, there was a significant interaction between procysteine ® and AZT on the M:E ratio for males and females.

Although AZT-treated groups demonstrated significant increases in the incidence of Howell Jolly Bodies, this effect was not consistent across sex or Procysteine ® cotreatment. The significant influence of Procysteine ® on AZT-induced bone marrow effects suggests that AZT induced changes in blood hematology would likely improve given longer Procysteine ® cotreatment.

Numbers of nucleated cells/femur (Coulter counts of aspirates) were significantly decreased compared to controls for males and females in high dose AZT/±-procysteine ® groups, and for females in low dose AZT/1% procysteine ®-treated group. Additionally, the significant decrease in nucleated cells per femur observed for females at the high dose of AZT/1% procysteine ®-treated group resulted in a significant interaction between Procysteine ® and AZT. The cause for this observation is not clear.

Although there were no significant differences compared to controls in the number of erythroid colonies, there were more erythroid colonies for the low dose AZT/1% Procysteine ®-treated groups compared to the AZT only treated groups, and a significant interaction between Procysteine ® and AZT were observed at this dose. Additionally, significant increases in the total number of colonies were noted for both high dose AZT groups. When the cellularity data (nucleated cells per femur) and colony forming data were normalized to give the total number of colony forming cells per femur, there were no significant group differences. This suggests that treatment with high dose AZT for 8 weeks, by reducing the number of precursor or mature cells, enriched the concentration of colony forming cells in the bone marrow.

There were no significant group differences in liver or kidney GSH. Blood GSH significantly decreased with increasing AZT dose. However, at the 0, 50, and 500 mg/kg/day AZT dosages, blood GSH concentrations were higher for Procysteine ®-cotreated groups than for AZT-only treated groups.

Histopathology of adrenal and skin revealed no abnormalities. However, analysis of tail revealed an AZT-induced accumulation of epidermal melanin-like pigment that was not as severe in Procysteine ® /AZT-cotreated groups.

In conclusion, AZT-induced bone marrow hypoplasia was ameliorated by cotreatment with Procysteine ®.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for reducing or preventing bone marrow hypoplasia in a patient at risk of same comprising the step of administering to a patient at risk of bone marrow hypoplasia because the patient is receiving AZT a therapeutically effective amount of a composition comprising L-2-oxothiazolidine-4-carboxylate.

2. The method of claim 1 wherein the composition is administered parenterally.

3. The method of claim 1 wherein the composition is administered enterally.

4. A method for treating bone marrow hypoplasia comprising the step of administering to a patient having bone marrow hypoplasia because the patient is receiving AZT a composition comprising L-2-oxothiazolidine-4-carboxylate in an amount sufficient to reduce the bone marrow hypoplasia of the patient.

5. The method of claim 4 wherein the composition is administered parenterally.

6. The method of claim 4 wherein the composition is administered enterally.

7. The method of claim 1 wherein the composition is administered contemporaneously with the AZT.

8. The method of claim 1 wherein the composition is administered on the same day the AZT is administered.

9. The method of claim 4 wherein the composition is administered contemporaneously with the AZT.

10. The method of claim 4 wherein the composition is administered on the same day the AZT is administered.

11. A method for reducing or preventing bone marrow hypoplasia in a patient at risk of same comprising the step of administering to an HIV positive patient at risk of bone marrow hypoplasia because the patient is receiving AZT a therapeutically effective amount of a composition comprising L-2-oxothiazolidine-4-carboxylate.

12. The method of claim 11 wherein the composition is administered parenterally.

13. The method of claim 11 wherein the composition is administered enterally.

14. The method of claim 11 wherein the composition is administered contemporaneously with the AZT.

15. The method of claim 11 wherein the composition is administered on the same day the AZT is administered.

16. A method for treating bone marrow hypoplasia comprising the step of administering to an HIV positive patient having bone marrow hypoplasia because the patient is receiving AZT a composition comprising L-2-oxothiazolidine-4-carboxylate in an amount sufficient to reduce the bone marrow hypoplasia of the patient.

17. The method of claim 16 wherein the composition is administered parenterally.

18. The method of claim 16 wherein the composition is administered enterally.

19. The method of claim 16 wherein the composition is administered contemporaneously with the AZT.

20. The method of claim 16 wherein the composition is administered on the same day the AZT is administered.

* * * * *